(12) United States Patent
Jin et al.

(10) Patent No.: US 9,567,589 B2
(45) Date of Patent: Feb. 14, 2017

(54) NGF APTAMER AND APPLICATION THEREOF

(71) Applicant: RIBOMIC INC., Tokyo (JP)

(72) Inventors: Ling Jin, Tokyo (JP); Hisanao Hiramatsu, Toyonaka (JP)

(73) Assignees: RIBOMIC INC., Tokyo (JP); FUJIMOTO PHARMACEUTICAL CORPORATION, Osaka (JP)

( * ) Notice: Subject to any disclaimer, the term of this patent is extended or adjusted under 35 U.S.C. 154(b) by 65 days.

(21) Appl. No.: 14/347,738

(22) PCT Filed: Sep. 28, 2012

(86) PCT No.: PCT/JP2012/075252
§ 371 (c)(1),
(2) Date: Mar. 27, 2014

(87) PCT Pub. No.: WO2013/047844
PCT Pub. Date: Apr. 4, 2013

(65) Prior Publication Data
US 2014/0235701 A1  Aug. 21, 2014

(30) Foreign Application Priority Data
Sep. 28, 2011 (JP) ................................. 2011-213585

(51) Int. Cl.
*C12N 15/11* (2006.01)
*A61K 48/00* (2006.01)
(Continued)

(52) U.S. Cl.
CPC ......... *C12N 15/115* (2013.01); *C12N 2310/16* (2013.01); *C12N 2310/317* (2013.01);
(Continued)

(58) Field of Classification Search
USPC .......................................... 536/24.5; 514/44
See application file for complete search history.

(56) References Cited

U.S. PATENT DOCUMENTS

| 2011/0251266 A1 | 10/2011 | Jin et al. |
| 2012/0165401 A1 | 6/2012 | Nakamura et al. |
| 2013/0052176 A1 | 2/2013 | Nakamura et al. |

FOREIGN PATENT DOCUMENTS

| WO | WO 91/19813 A1 | 12/1991 |
| WO | WO 94/08050 A1 | 4/1994 |

(Continued)

OTHER PUBLICATIONS

Binkley et al., "RNA Ligands to Human Nerve Growth Factor", Nucleic Acids Research, 1995, pp. 3198-3205, vol. 23, No. 16.
(Continued)

*Primary Examiner* — Terra C Gibbs
(74) *Attorney, Agent, or Firm* — Birch, Stewart, Kolasch & Birch, LLP

(57) ABSTRACT

The present invention provides an aptamer binding to NGF and capable of forming a potential secondary structure represented by the formula (I):

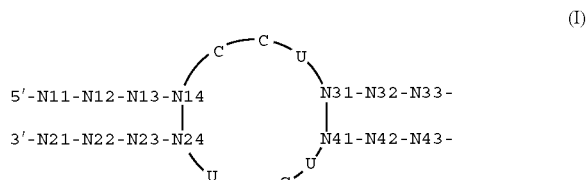

(Continued)

SEQ ID NO:3

-continued

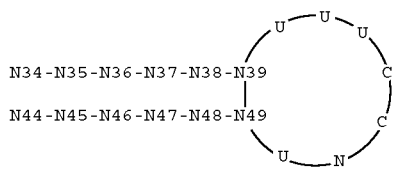

wherein N is one nucleotide selected from the group consisting of A, G, C, U and T, N11-N13, N21-N23, N32-N38 and N42-N48 are the same or different and each is a bond or 1 or 2 nucleotides selected from the group consisting of A, G, C, U and T, N14, N24, N31, N41, N39 and N49 are the same or different and each is one nucleotide selected from the group consisting of A, G, C, U and T, N14 and N24, N31 and N41, and N39 and N49 each form a Watson-Crick base pair, N11-N12-N13-N14 and N21-N22-N23-N24 are nucleotide sequences capable of forming a stem structure in combination, and N31-N32-N33-N34-N35-N36-N37-N38-N39 and N41-N42-N43-N44-N45-N46-N47-N48-N49 are nucleotide sequences capable of forming a stem structure in combination.

21 Claims, 4 Drawing Sheets

(51) Int. Cl.
C07H 21/02 (2006.01)
C07H 21/04 (2006.01)
C12N 15/115 (2010.01)

(52) U.S. Cl.
CPC .. *C12N 2310/344* (2013.01); *C12N 2310/351* (2013.01); *C12N 2320/30* (2013.01)

(56) References Cited

FOREIGN PATENT DOCUMENTS

| WO | WO 95/07364 A1 | 3/1995 |
| WO | WO 02/077262 A2 | 10/2002 |
| WO | WO 03/070984 A1 | 8/2003 |
| WO | WO 2010/035725 A1 | 4/2010 |
| WO | WO 2010/143714 A1 | 12/2010 |
| WO | WO 2011/118682 A1 | 9/2011 |

OTHER PUBLICATIONS

European Patent Office Search Report dated May 22, 2015 for EP Application No. 12835044.4.
International Search Report mailed Nov. 20, 2012 for PCT/JP2012/075252.
Thayer et al., "Separation of Oligonucleotide Phosphorothioate Diasteroisomers by Pellicular Anion-Exchange Chromatography", Journal of Chromatography A, 2011, pp. 802-808, vol. 1218, No. 6.
Ulrich et al., "DNA and RNA Aptamers: From Tools for Basic Research Towards Therapeutic Applications", Combinatorial Chemistry and High Throughput Screening, 2006, pp. 619-632, vol. 9, No. 8.

SEQ ID NO:3

SEQUENCE LISTING

```
<160> NUMBER OF SEQ ID NOS: 168

<210> SEQ ID NO 1
<211> LENGTH: 83
<212> TYPE: DNA
<213> ORGANISM: Artificial
<220> FEATURE:
<223> OTHER INFORMATION: Aptamer to NGF

<400> SEQUENCE: 1
gggagaacuu cgaccagaag uugacgacca acucgucucu uauggauuua cgugaacccg    60
uaugugcgca uacauggauc cuc                                           83

<210> SEQ ID NO 2
<211> LENGTH: 82
<212> TYPE: DNA
<213> ORGANISM: Artificial
<220> FEATURE:
<223> OTHER INFORMATION: Aptamer to NGF

<400> SEQUENCE: 2
gggagaacuu cgaccagaag uccaaacggg acuuuauacc ucugagucgc cuacgcuccu    60
augugcgcau acauggaucc uc                                            82

<210> SEQ ID NO 3
<211> LENGTH: 83
<212> TYPE: DNA
<213> ORGANISM: Artificial
<220> FEATURE:
<223> OTHER INFORMATION: Aptamer to NGF

<400> SEQUENCE: 3
gggagaacuu cgaccagaag uuggcacauc cugcugcgua guuuccgucu ccguggcugu    60
uaugugcgca uacauggauc cuc                                           83

<210> SEQ ID NO 4
<211> LENGTH: 91
```

```
<212> TYPE: DNA
<213> ORGANISM: Artificial
<220> FEATURE:
<223> OTHER INFORMATION: Aptamer to NGF

<400> SEQUENCE: 4
gggagaacuu cgaccagaag uacguuagua cguuugcaua uguacaaccu ugcauacgau     60
acguagauua ugugcgcaua cauggauccu c                                   91

<210> SEQ ID NO 5
<211> LENGTH: 83
<212> TYPE: DNA
<213> ORGANISM: Artificial
<220> FEATURE:
<223> OTHER INFORMATION: Aptamer to NGF

<400> SEQUENCE: 5
gggagaacuu cgaccagaag uuagaagagg acuaguugcu aaugcccugg uucgucgcua     60
uaugugcgca uacauggauc cuc                                            83

<210> SEQ ID NO 6
<211> LENGTH: 83
<212> TYPE: DNA
<213> ORGANISM: Artificial
<220> FEATURE:
<223> OTHER INFORMATION: Aptamer to NGF

<400> SEQUENCE: 6
gggagaacuu cgaccagaag ugcaauacuu ucgcggcaua ugucaaaccu ugccacgac     60 uaugugcgca uacauggauc cuc                                            83

<210> SEQ ID NO 7
<211> LENGTH: 81
<212> TYPE: DNA
<213> ORGANISM: Artificial
<220> FEATURE:
<223> OTHER INFORMATION: Aptamer to NGF

<400> SEQUENCE: 7
gggagaacuu cgaccagaag acgcaccucu uaucacacau gcgucagccu ugugauacua     60
ugugcgcaua cauggauccu c                                              81

<210> SEQ ID NO 8
<211> LENGTH: 83
<212> TYPE: DNA
<213> ORGANISM: Artificial
<220> FEATURE:
<223> OTHER INFORMATION: Aptamer to NGF

<400> SEQUENCE: 8
gggagaacuu cgaccagaag auccacuggu acuacgugac cccgcauagg caauccugcu     60
uaugugcgca uacauggauc cuc                                            83

<210> SEQ ID NO 9
<211> LENGTH: 73
<212> TYPE: DNA
<213> ORGANISM: Artificial
<220> FEATURE:
<223> OTHER INFORMATION: Aptamer to NGF

<400> SEQUENCE: 9
gggagaacuu cgaccagaag uuggcacauc cugcugcgua guuccgucu ccguggcugu      60
```

```
uaugugcgca uac                                                            73

<210> SEQ ID NO 10
<211> LENGTH: 68
<212> TYPE: DNA
<213> ORGANISM: Artificial
<220> FEATURE:
<223> OTHER INFORMATION: Aptamer to NGF

<400> SEQUENCE: 10
gggagaacuu cgaccagaag uuggcacauc cugcugcgua guuccgucu ccguggcugu          60 uaugugcg                                                                  68

<210> SEQ ID NO 11
<211> LENGTH: 46
<212> TYPE: DNA
<213> ORGANISM: Artificial
<220> FEATURE:
<223> OTHER INFORMATION: Aptamer to NGF

<400> SEQUENCE: 11
gggcacaucc ugcugcguag uuccgucuc cguggcuguu augugc                        46

<210> SEQ ID NO 12
<211> LENGTH: 40
<212> TYPE: DNA
<213> ORGANISM: Artificial
<220> FEATURE:
<223> OTHER INFORMATION: Aptamer to NGF

<400> SEQUENCE: 12
ggguccugcu gcguaguuuc cgucccgug gcuguuaccc                               40

<210> SEQ ID NO 13
<211> LENGTH: 42
<212> TYPE: DNA
<213> ORGANISM: Artificial
<220> FEATURE:
<223> OTHER INFORMATION: Aptamer to NGF

<400> SEQUENCE: 13
gggguccugc ugcguaguuu ccgucuccgu ggcuguuacc cc                           42

<210> SEQ ID NO 14
<211> LENGTH: 78
<212> TYPE: DNA
<213> ORGANISM: Artificial
<220> FEATURE:
<223> OTHER INFORMATION: Aptamer to NGF

<400> SEQUENCE: 14
gggagaacuu cgaccagaag ugcaauacuu ucgcggcaua ugugcaaacc uugccacgac        60
uaugugcgca uacaugga                                                       78

<210> SEQ ID NO 15
<211> LENGTH: 73
<212> TYPE: DNA
<213> ORGANISM: Artificial
<220> FEATURE:
<223> OTHER INFORMATION: Aptamer to NGF

<400> SEQUENCE: 15
gggagaacuu cgaccagaag ugcaauacuu ucgcggcaua ugugcaaacc uugccacgac        60
uaugugcgca uac                                                            73
```

<210> SEQ ID NO 16
<211> LENGTH: 63
<212> TYPE: DNA
<213> ORGANISM: Artificial
<220> FEATURE:
<223> OTHER INFORMATION: Aptamer to NGF

<400> SEQUENCE: 16
cgaccagaag ugcaauacuu ucgcggcaua ugugcaaacc uugccacgac uaugugcgca    60
uac                                                                 63

<210> SEQ ID NO 17
<211> LENGTH: 58
<212> TYPE: DNA
<213> ORGANISM: Artificial
<220> FEATURE:
<223> OTHER INFORMATION: Aptamer to NGF

<400> SEQUENCE: 17
agaagugcaa uacuuucgcg gcauaugugc aaaccuugcc acgacuaugu gcgcauac     58

<210> SEQ ID NO 18
<211> LENGTH: 48
<212> TYPE: DNA
<213> ORGANISM: Artificial
<220> FEATURE:
<223> OTHER INFORMATION: Aptamer to NGF

<400> SEQUENCE: 18
ugcaauacuu ucgcggcaua ugugcaaacc uugccacgac uaugugcg                48

<210> SEQ ID NO 19
<211> LENGTH: 46
<212> TYPE: DNA
<213> ORGANISM: Artificial
<220> FEATURE:
<223> OTHER INFORMATION: Aptamer to NGF

<400> SEQUENCE: 19
gcaauacuuu cgcggcauau gugcaaaccu ugccacgacu augugc                  46

<210> SEQ ID NO 20
<211> LENGTH: 50
<212> TYPE: DNA
<213> ORGANISM: Artificial
<220> FEATURE:
<223> OTHER INFORMATION: Aptamer to NGF

<400> SEQUENCE: 20
gugcaauacu uucgcggcau augugcaaac cuugccacga cuaugugcgc              50

<210> SEQ ID NO 21
<211> LENGTH: 48
<212> TYPE: DNA
<213> ORGANISM: Artificial
<220> FEATURE:
<223> OTHER INFORMATION: Aptamer to NGF

<400> SEQUENCE: 21
gggaauacuu ucgcggcaua ugugcaaacc uugccacgac uauguccc                48

<210> SEQ ID NO 22
<211> LENGTH: 83
<212> TYPE: DNA

```
<213> ORGANISM: Artificial
<220> FEATURE:
<223> OTHER INFORMATION: Aptamer to NGF

<400> SEQUENCE: 22
gggagaacuu cgaccagaag uuggcacauc cugcugcgua guuccgucu ucguggcugu      60 uaugugcgca uacauggauc cuc                                             83

<210> SEQ ID NO 23
<211> LENGTH: 82
<212> TYPE: DNA
<213> ORGANISM: Artificial
<220> FEATURE:
<223> OTHER INFORMATION: Aptamer to NGF

<400> SEQUENCE: 23
gggagaacuu cgaccagaag uggcacaucc ugcugcguag uuccgucug cguggcuguu      60 augugcgcau acauggaucc uc                                              82

<210> SEQ ID NO 24
<211> LENGTH: 83
<212> TYPE: DNA
<213> ORGANISM: Artificial
<220> FEATURE:
<223> OTHER INFORMATION: Aptamer to NGF

<400> SEQUENCE: 24
gggagaacuu cgaccagaag uuggcacauc cugcugcgaa guuccgucu ccguggcugu      60 uaugugcgca uacauggauc cuc                                             83

<210> SEQ ID NO 25
<211> LENGTH: 83
<212> TYPE: DNA
<213> ORGANISM: Artificial
<220> FEATURE:
<223> OTHER INFORMATION: Aptamer to NGF

<400> SEQUENCE: 25
gggagaacuu cgaccagaag uuggcacauc cugcugcgca guuccgucu acguggcugu      60 uaugugcgca uacauggauc cuc                                             83

<210> SEQ ID NO 26
<211> LENGTH: 82
<212> TYPE: DNA
<213> ORGANISM: Artificial
<220> FEATURE:
<223> OTHER INFORMATION: Aptamer to NGF

<400> SEQUENCE: 26
gggagaacuu cgaccagaag uggcacaucc ugcugcguag uuccgucuu cgcggcuguu      60 augugcgcau acauggaucc uc                                              82

<210> SEQ ID NO 27
<211> LENGTH: 83
<212> TYPE: DNA
<213> ORGANISM: Artificial
<220> FEATURE:
<223> OTHER INFORMATION: Aptamer to NGF

<400> SEQUENCE: 27
gggagaacuu cgaccagaag uuggcacauc cugcugcgca guuccgucu gcguggcugu      60 uaugugcgca uacauggauc cuc                                             83
```

<210> SEQ ID NO 28
<211> LENGTH: 83
<212> TYPE: DNA
<213> ORGANISM: Artificial
<220> FEATURE:
<223> OTHER INFORMATION: Aptamer to NGF

<400> SEQUENCE: 28
gggagaacuu cgaccagaag uuggcacauc cugcugcgua guuuccaucu gcguggcugu    60
uaugugcgca uacauggauc cuc                                           83

<210> SEQ ID NO 29
<211> LENGTH: 81
<212> TYPE: DNA
<213> ORGANISM: Artificial
<220> FEATURE:
<223> OTHER INFORMATION: Aptamer to NGF

<400> SEQUENCE: 29
gggagaacuu cgaccagaag uucacauccu gcugcgaagu uccuucuuc guggcuguua    60 ugugcgcaua cauggauccu c                                             81

<210> SEQ ID NO 30
<211> LENGTH: 85
<212> TYPE: DNA
<213> ORGANISM: Artificial
<220> FEATURE:
<223> OTHER INFORMATION: Aptamer to NGF

<400> SEQUENCE: 30
gggagaacuu cgaccagaag uuggcacauc cugcugcgaa gguuccgucu ucguggcugu    60
acuaugugcg cauacaugga uccuc                                         85

<210> SEQ ID NO 31
<211> LENGTH: 83
<212> TYPE: DNA
<213> ORGANISM: Artificial
<220> FEATURE:
<223> OTHER INFORMATION: Aptamer to NGF

<400> SEQUENCE: 31
gggagaacuu cgaccagaag uuggcacauc cugcugcgca guuucccucu gcguggcugu    60
uaugugcgca uacauggauc cuc                                           83

<210> SEQ ID NO 32
<211> LENGTH: 83
<212> TYPE: DNA
<213> ORGANISM: Artificial
<220> FEATURE:
<223> OTHER INFORMATION: Aptamer to NGF

<400> SEQUENCE: 32
gggagaacuu cgaccagaag uuggcacauc cugcugcgga guuccuucu ucguggcugu    60 uaugugcgca uacauggauc cuc                                           83

<210> SEQ ID NO 33
<211> LENGTH: 83
<212> TYPE: DNA
<213> ORGANISM: Artificial
<220> FEATURE:
<223> OTHER INFORMATION: Aptamer to NGF

```
<400> SEQUENCE: 33
gggagaacuu cgaccagaag uuggcacauc cugccgcgua guuucaaucu gguggcgug      60 uaugugcgca uacauggauc cuc                                            83

<210> SEQ ID NO 34
<211> LENGTH: 83
<212> TYPE: DNA
<213> ORGANISM: Artificial
<220> FEATURE:
<223> OTHER INFORMATION: Aptamer to NGF

<400> SEQUENCE: 34
gggagaacuu cgaccagaag uuggcacauc cugccgcgua guuccgucu gcguggcugu      60 uaugugcgca uacauggauc cuc                                            83

<210> SEQ ID NO 35
<211> LENGTH: 83
<212> TYPE: DNA
<213> ORGANISM: Artificial
<220> FEATURE:
<223> OTHER INFORMATION: Aptamer to NGF

<400> SEQUENCE: 35
gggagaacuu cgaccagaag uuggcacauc cuguugcgua guuccuucu acguggcugu      60 uaugucgca uacauggauc cuc                                             83

<210> SEQ ID NO 36
<211> LENGTH: 92
<212> TYPE: DNA
<213> ORGANISM: Artificial
<220> FEATURE:
<223> OTHER INFORMATION: Aptamer to NGF

<400> SEQUENCE: 36
gggagaacuu cgaccagaag guacguuagu acguuugcau auguacaacc uugcauacga     60
uacguagguu augugcgcau acauggaucc uc                                  92

<210> SEQ ID NO 37
<211> LENGTH: 83
<212> TYPE: DNA
<213> ORGANISM: Artificial
<220> FEATURE:
<223> OTHER INFORMATION: Aptamer to NGF

<400> SEQUENCE: 37
gggagaacuu cgaccagaag uuggcacauc cugcuacgua guuccuucu ucguggcugu      60 uaugugcgca uacauggauc cuc                                            83

<210> SEQ ID NO 38
<211> LENGTH: 40
<212> TYPE: DNA
<213> ORGANISM: Artificial
<220> FEATURE:
<223> OTHER INFORMATION: Aptamer to NGF

<400> SEQUENCE: 38
ggguccugcu gcguaguuuc cgucuucgcg gcguuaccc                            40

<210> SEQ ID NO 39
<211> LENGTH: 40
<212> TYPE: DNA
<213> ORGANISM: Artificial
```

-continued

```
<220> FEATURE:
<223> OTHER INFORMATION: Aptamer to NGF

<400> SEQUENCE: 39
ggguccugcu gcgcaguuuc cgucugcgug gcuguuaccc                                 40

<210> SEQ ID NO 40
<211> LENGTH: 40
<212> TYPE: DNA
<213> ORGANISM: Artificial
<220> FEATURE:
<223> OTHER INFORMATION: Aptamer to NGF

<400> SEQUENCE: 40
ggguccugcu gcguaguuuc caucugcgug gcuguuaccc                                 40

<210> SEQ ID NO 41
<211> LENGTH: 40
<212> TYPE: DNA
<213> ORGANISM: Artificial
<220> FEATURE:
<223> OTHER INFORMATION: Aptamer to NGF

<400> SEQUENCE: 41
ggguccugcu gcgaaguuuc cuucuucgug gcuguuaccc                                 40

<210> SEQ ID NO 42
<211> LENGTH: 40
<212> TYPE: DNA
<213> ORGANISM: Artificial
<220> FEATURE:
<223> OTHER INFORMATION: Aptamer to NGF

<400> SEQUENCE: 42
ggguccugcu gcgcaguuuc ccucugcgug gcuguuaccc                                 40

<210> SEQ ID NO 43
<211> LENGTH: 40
<212> TYPE: DNA
<213> ORGANISM: Artificial
<220> FEATURE:
<223> OTHER INFORMATION: Aptamer to NGF

<400> SEQUENCE: 43
ggguccugcu gcggaguuuc cuucuucgug gcuguuaccc                                 40

<210> SEQ ID NO 44
<211> LENGTH: 40
<212> TYPE: DNA
<213> ORGANISM: Artificial
<220> FEATURE:
<223> OTHER INFORMATION: Aptamer to NGF

<400> SEQUENCE: 44
ggguccugcc gcguaguuuc cgucugcgug gcuguuaccc                                 40

<210> SEQ ID NO 45
<211> LENGTH: 40
<212> TYPE: DNA
<213> ORGANISM: Artificial
<220> FEATURE:
<223> OTHER INFORMATION: Aptamer to NGF

<400> SEQUENCE: 45
ggguccuguu gcguaguuuc cuucuacgug gcuguuaccc                                 40
```

```
<210> SEQ ID NO 46
<211> LENGTH: 40
<212> TYPE: DNA
<213> ORGANISM: Artificial
<220> FEATURE:
<223> OTHER INFORMATION: Aptamer to NGF

<400> SEQUENCE: 46
ggguccugcu gcgcaguuuc cgucuacgug gcuguuaccc                                40

<210> SEQ ID NO 47
<211> LENGTH: 40
<212> TYPE: DNA
<213> ORGANISM: Artificial
<220> FEATURE:
<223> OTHER INFORMATION: Aptamer to NGF

<400> SEQUENCE: 47
ggguccugcu gcguaguuuc cgucuucgcg gcuguuaccc                                40

<210> SEQ ID NO 48
<211> LENGTH: 83
<212> TYPE: DNA
<213> ORGANISM: Artificial
<220> FEATURE:
<223> OTHER INFORMATION: Aptamer to NGF

<400> SEQUENCE: 48
gggagaacuu cgaccagaag uuggcacauc cugcugcgga guuccgucu cgguggcugu           60 uaugugcgca uacauggauc cuc                                                  83

<210> SEQ ID NO 49
<211> LENGTH: 83
<212> TYPE: DNA
<213> ORGANISM: Artificial
<220> FEATURE:
<223> OTHER INFORMATION: Aptamer to NGF

<400> SEQUENCE: 49
gggagaacuu cgaccagaag uuugcacauc cugcugcgua guuccgucu acguggcugu           60 uaugugcgca uacauggauc cuc                                                  83

<210> SEQ ID NO 50
<211> LENGTH: 83
<212> TYPE: DNA
<213> ORGANISM: Artificial
<220> FEATURE:
<223> OTHER INFORMATION: Aptamer to NGF

<400> SEQUENCE: 50
gggagaacuu cgaccagaag cuggcacauc cuguugcgua guuccgucu acgugacugu           60 uaugugcgca uacauggauc cuc                                                  83

<210> SEQ ID NO 51
<211> LENGTH: 83
<212> TYPE: DNA
<213> ORGANISM: Artificial
<220> FEATURE:
<223> OTHER INFORMATION: Aptamer to NGF

<400> SEQUENCE: 51
gggagaacuu cgaccagaag uuggcacacc cugcuacgga guuccgucu cgguggcugu           60 uaugugcgca uacauggauc cuc                                                  83
```

<210> SEQ ID NO 52
<211> LENGTH: 83
<212> TYPE: DNA
<213> ORGANISM: Artificial
<220> FEATURE:
<223> OTHER INFORMATION: Aptamer to NGF

<400> SEQUENCE: 52
gggagaacuu cgaccagaag uuggcacauc cugcugcaua guuccgucu uuguggcugu        60 uaugugcgca uacauggauc cuc                                              83

<210> SEQ ID NO 53
<211> LENGTH: 83
<212> TYPE: DNA
<213> ORGANISM: Artificial
<220> FEATURE:
<223> OTHER INFORMATION: Aptamer to NGF

<400> SEQUENCE: 53
gggagaacuu cgaccagaag uuugcacauc cugcugcgca guuccgucu acguggcugu        60 uaugugcgca uacauggauc cuc                                              83

<210> SEQ ID NO 54
<211> LENGTH: 83
<212> TYPE: DNA
<213> ORGANISM: Artificial
<220> FEATURE:
<223> OTHER INFORMATION: Aptamer to NGF

<400> SEQUENCE: 54
gggagaacuu cgaccagaag uuggcacauc cugaugcgua guuccgucu gcgugucugu        60 uaugugcgca uacauggauc cuc                                              83

<210> SEQ ID NO 55
<211> LENGTH: 83
<212> TYPE: DNA
<213> ORGANISM: Artificial
<220> FEATURE:
<223> OTHER INFORMATION: Aptamer to NGF

<400> SEQUENCE: 55
gggagaacuu cgaccagaag uuggcacauc cuguugcgua guuccgucu gcguggcugu        60 uaugugcgca uacauggauc cuc                                              83

<210> SEQ ID NO 56
<211> LENGTH: 82
<212> TYPE: DNA
<213> ORGANISM: Artificial
<220> FEATURE:
<223> OTHER INFORMATION: Aptamer to NGF

<400> SEQUENCE: 56
gggagaacuu cgaccagaag uugcacaucc ugcuguguag uuccgucug cagguugu          60 augugcgcau acauggaucc uc                                               82

<210> SEQ ID NO 57
<211> LENGTH: 83
<212> TYPE: DNA
<213> ORGANISM: Artificial
<220> FEATURE:
<223> OTHER INFORMATION: Aptamer to NGF

<400> SEQUENCE: 57
gggagaacuu cgaccagaag uaggcacguc cugcugcaua guuccgucu guguggcugu    60 uaugugcgca uacauggauc cuc    83

<210> SEQ ID NO 58
<211> LENGTH: 83
<212> TYPE: DNA
<213> ORGANISM: Artificial
<220> FEATURE:
<223> OTHER INFORMATION: Aptamer to NGF

<400> SEQUENCE: 58
gggagaacuu cgaccagaag uugacacauc cugcugcgua guuccgucu gcgugguugu    60 uaugugcgca uacauggauc cuc    83

<210> SEQ ID NO 59
<211> LENGTH: 83
<212> TYPE: DNA
<213> ORGANISM: Artificial
<220> FEATURE:
<223> OTHER INFORMATION: Aptamer to NGF

<400> SEQUENCE: 59
gggagaacuu cgaccagaag uuugcacauc cugcugcgua guuccuucu gcgugguugu    60 uaugugcgca uacauggauc cuc    83

<210> SEQ ID NO 60
<211> LENGTH: 83
<212> TYPE: DNA
<213> ORGANISM: Artificial
<220> FEATURE:
<223> OTHER INFORMATION: Aptamer to NGF

<400> SEQUENCE: 60
gggagaacuu cgaccagaag uuggcacauc cugcugcaga guuccgucu cgguggcugu    60 uaugugcgca uacauggauc cuc    83

<210> SEQ ID NO 61
<211> LENGTH: 83
<212> TYPE: DNA
<213> ORGANISM: Artificial
<220> FEATURE:
<223> OTHER INFORMATION: Aptamer to NGF

<400> SEQUENCE: 61
gggagaacuu cgaccagaag uuagcacauc cugcugcgua guuccgucu ucgcgguugu    60 uaugugcgca uacauggauc cuc    83

<210> SEQ ID NO 62
<211> LENGTH: 40
<212> TYPE: DNA
<213> ORGANISM: Artificial
<220> FEATURE:
<223> OTHER INFORMATION: Aptamer to NGF

<400> SEQUENCE: 62
ggguccugcu gcggaguuuc cgucucggug gcuguuaccc    40

<210> SEQ ID NO 63
<211> LENGTH: 40
<212> TYPE: DNA
<213> ORGANISM: Artificial

```
<220> FEATURE:
<223> OTHER INFORMATION: Aptamer to NGF

<400> SEQUENCE: 63 gguccugcu gcguaguuuc cgucuacgug gcuguuaccc                    40

<210> SEQ ID NO 64
<211> LENGTH: 40
<212> TYPE: DNA
<213> ORGANISM: Artificial
<220> FEATURE:
<223> OTHER INFORMATION: Aptamer to NGF

<400> SEQUENCE: 64
ggguccuguu gcguaguuuc cgucuacgug acuguuaccc                    40

<210> SEQ ID NO 65
<211> LENGTH: 40
<212> TYPE: DNA
<213> ORGANISM: Artificial
<220> FEATURE:
<223> OTHER INFORMATION: Aptamer to NGF

<400> SEQUENCE: 65
ggguccugcu acggaguuuc cgucucggug gcuguuaccc                    40

<210> SEQ ID NO 66
<211> LENGTH: 40
<212> TYPE: DNA
<213> ORGANISM: Artificial
<220> FEATURE:
<223> OTHER INFORMATION: Aptamer to NGF

<400> SEQUENCE: 66
ggguccugcu gcauaguuuc cgucuuugug gcuguuaccc                    40

<210> SEQ ID NO 67
<211> LENGTH: 40
<212> TYPE: DNA
<213> ORGANISM: Artificial
<220> FEATURE:
<223> OTHER INFORMATION: Aptamer to NGF

<400> SEQUENCE: 67
ggguccugcu gcgcaguuuc cgucuacgug gcuguuaccc                    40

<210> SEQ ID NO 68
<211> LENGTH: 40
<212> TYPE: DNA
<213> ORGANISM: Artificial
<220> FEATURE:
<223> OTHER INFORMATION: Aptamer to NGF

<400> SEQUENCE: 68
ggguccugau gcguaguuuc cgucugcgug ucuguuaccc                    40

<210> SEQ ID NO 69
<211> LENGTH: 40
<212> TYPE: DNA
<213> ORGANISM: Artificial
<220> FEATURE:
<223> OTHER INFORMATION: Aptamer to NGF

<400> SEQUENCE: 69
ggguccuguu gcguaguuuc cgucugcgug gcuguuaccc                    40
```

<210> SEQ ID NO 70
<211> LENGTH: 40
<212> TYPE: DNA
<213> ORGANISM: Artificial
<220> FEATURE:
<223> OTHER INFORMATION: Aptamer to NGF

<400> SEQUENCE: 70 gguccugcu guguaguuuc cgucugcaug guuguuaccc                    40

<210> SEQ ID NO 71
<211> LENGTH: 40
<212> TYPE: DNA
<213> ORGANISM: Artificial
<220> FEATURE:
<223> OTHER INFORMATION: Aptamer to NGF

<400> SEQUENCE: 71
ggguccugcu gcauaguuuc cgucugugug gcuguuaccc                   40

<210> SEQ ID NO 72
<211> LENGTH: 40
<212> TYPE: DNA
<213> ORGANISM: Artificial
<220> FEATURE:
<223> OTHER INFORMATION: Aptamer to NGF

<400> SEQUENCE: 72
ggguccugcu gcguaguuuc cgucugcgug guuguuaccc                   40

<210> SEQ ID NO 73
<211> LENGTH: 40
<212> TYPE: DNA
<213> ORGANISM: Artificial
<220> FEATURE:
<223> OTHER INFORMATION: Aptamer to NGF

<400> SEQUENCE: 73
ggguccugcu gcguaguuuc cuucugcgug guuguuaccc                   40

<210> SEQ ID NO 74
<211> LENGTH: 40
<212> TYPE: DNA
<213> ORGANISM: Artificial
<220> FEATURE:
<223> OTHER INFORMATION: Aptamer to NGF

<400> SEQUENCE: 74
ggguccugcu gcagaguuuc cgucucggug gcuguuaccc                   40

<210> SEQ ID NO 75
<211> LENGTH: 40
<212> TYPE: DNA
<213> ORGANISM: Artificial
<220> FEATURE:
<223> OTHER INFORMATION: Aptamer to NGF

<400> SEQUENCE: 75
ggguccugcu gcguaguuuc cgucuucgcg guuguuaccc                   40

<210> SEQ ID NO 76
<211> LENGTH: 40
<212> TYPE: DNA
<213> ORGANISM: Artificial
<220> FEATURE:
<223> OTHER INFORMATION: Aptamer to NGF

```
<400> SEQUENCE: 76 gguccugau uaagaguuuc cgucucguaa ucuguuaccc                              40

<210> SEQ ID NO 77
<211> LENGTH: 40
<212> TYPE: DNA
<213> ORGANISM: Artificial
<220> FEATURE:
<223> OTHER INFORMATION: Aptamer to NGF

<400> SEQUENCE: 77
ggguccugac uaagaguuuc cgucucguag ucuguuaccc                              40

<210> SEQ ID NO 78
<211> LENGTH: 40
<212> TYPE: DNA
<213> ORGANISM: Artificial
<220> FEATURE:
<223> OTHER INFORMATION: Aptamer to NGF

<400> SEQUENCE: 78
ggguccuggc caagaguuuc cgucucgugg ucuguuaccc                              40

<210> SEQ ID NO 79
<211> LENGTH: 40
<212> TYPE: DNA
<213> ORGANISM: Artificial
<220> FEATURE:
<223> OTHER INFORMATION: Aptamer to NGF

<400> SEQUENCE: 79
ggguccuggu uaagaguuuc cgucucguaa ccuguuaccc                              40

<210> SEQ ID NO 80
<211> LENGTH: 40
<212> TYPE: DNA
<213> ORGANISM: Artificial
<220> FEATURE:
<223> OTHER INFORMATION: Aptamer to NGF

<400> SEQUENCE: 80
ggguccuggc uaagaguuuc cgucucguag ucuguuaccc                              40

<210> SEQ ID NO 81
<211> LENGTH: 40
<212> TYPE: DNA
<213> ORGANISM: Artificial
<220> FEATURE:
<223> OTHER INFORMATION: Aptamer to NGF

<400> SEQUENCE: 81
ggguccuggu gauaaguuuc cgucuuauca ccuguuaccc                              40

<210> SEQ ID NO 82
<211> LENGTH: 40
<212> TYPE: DNA
<213> ORGANISM: Artificial
<220> FEATURE:
<223> OTHER INFORMATION: Aptamer to NGF

<400> SEQUENCE: 82
ggguccugga uaagaguuuc cgucucguau ccuguuaccc                              40

<210> SEQ ID NO 83
```

```
<211> LENGTH: 40
<212> TYPE: DNA
<213> ORGANISM: Artificial
<220> FEATURE:
<223> OTHER INFORMATION: Aptamer to NGF

<400> SEQUENCE: 83 gguccugua caagaguuuc cgucucgugu acuguuaccc                              40

<210> SEQ ID NO 84
<211> LENGTH: 40
<212> TYPE: DNA
<213> ORGANISM: Artificial
<220> FEATURE:
<223> OTHER INFORMATION: Aptamer to NGF

<400> SEQUENCE: 84
ggguccuguc gcuaaguuuc cgucuuugcg gcuguuaccc                              40

<210> SEQ ID NO 85
<211> LENGTH: 40
<212> TYPE: DNA
<213> ORGANISM: Artificial
<220> FEATURE:
<223> OTHER INFORMATION: Aptamer to NGF

<400> SEQUENCE: 85
ggguccugag uaagaguuuc cgucucauac ucuguuaccc                              40

<210> SEQ ID NO 86
<211> LENGTH: 40
<212> TYPE: DNA
<213> ORGANISM: Artificial
<220> FEATURE:
<223> OTHER INFORMATION: Aptamer to NGF

<400> SEQUENCE: 86
ggguccugcu gcguaguuuc cuucugcgug guuguuaccc                              40

<210> SEQ ID NO 87
<211> LENGTH: 40
<212> TYPE: DNA
<213> ORGANISM: Artificial
<220> FEATURE:
<223> OTHER INFORMATION: Aptamer to NGF

<400> SEQUENCE: 87
ggguccugcu caagaguuuc cgucucgugg gcuguuaccc                              40

<210> SEQ ID NO 88
<211> LENGTH: 40
<212> TYPE: DNA
<213> ORGANISM: Artificial
<220> FEATURE:
<223> OTHER INFORMATION: Aptamer to NGF

<400> SEQUENCE: 88
ggguccuguu caagaguuuc cgucucguga acuguuaccc                              40

<210> SEQ ID NO 89
<211> LENGTH: 40
<212> TYPE: DNA
<213> ORGANISM: Artificial
<220> FEATURE:
<223> OTHER INFORMATION: Aptamer to NGF

<400> SEQUENCE: 89
```
ggguccugug gaagaguuuc cgucucgucc acuguuaccc        40

<210> SEQ ID NO 90
<211> LENGTH: 40
<212> TYPE: DNA
<213> ORGANISM: Artificial
<220> FEATURE:
<223> OTHER INFORMATION: Aptamer to NGF

<400> SEQUENCE: 90
ggguccugcg uaagaguuuc cgucucguau gcuguuaccc        40

<210> SEQ ID NO 91
<211> LENGTH: 40
<212> TYPE: DNA
<213> ORGANISM: Artificial
<220> FEATURE:
<223> OTHER INFORMATION: Aptamer to NGF

<400> SEQUENCE: 91
ggguccugcc uaagaguuuc cgucucguag gcuguuaccc        40

<210> SEQ ID NO 92
<211> LENGTH: 39
<212> TYPE: DNA
<213> ORGANISM: Artificial
<220> FEATURE:
<223> OTHER INFORMATION: Aptamer to NGF

<400> SEQUENCE: 92
ggguccugac caagaguuuc cgucucgugg ucguaccc         39

<210> SEQ ID NO 93
<211> LENGTH: 40
<212> TYPE: DNA
<213> ORGANISM: Artificial
<220> FEATURE:
<223> OTHER INFORMATION: Aptamer to NGF

<400> SEQUENCE: 93
ggguccugcc gcguaguuuc cgucuucgcg guuguuaccc       40

<210> SEQ ID NO 94
<211> LENGTH: 40
<212> TYPE: DNA
<213> ORGANISM: Artificial
<220> FEATURE:
<223> OTHER INFORMATION: Aptamer to NGF

<400> SEQUENCE: 94
ggguccugcu gcguaguuuc cgucugcgga gcuguuaccc       40

<210> SEQ ID NO 95
<211> LENGTH: 40
<212> TYPE: DNA
<213> ORGANISM: Artificial
<220> FEATURE:
<223> OTHER INFORMATION: Aptamer to NGF

<400> SEQUENCE: 95
ggguccugcu gcguaguuuc caucuucgug gcuguuaccc       40

<210> SEQ ID NO 96
<211> LENGTH: 40
<212> TYPE: DNA

<213> ORGANISM: Artificial
<220> FEATURE:
<223> OTHER INFORMATION: Aptamer to NGF

<400> SEQUENCE: 96
ggguccugcu gcguaguuuc cgucuaugug gcuguuaccc    40

<210> SEQ ID NO 97
<211> LENGTH: 40
<212> TYPE: DNA
<213> ORGANISM: Artificial
<220> FEATURE:
<223> OTHER INFORMATION: Aptamer to NGF

<400> SEQUENCE: 97
ggguccugcu acguaguuuc cgucugcgug gcuguuaccc    40

<210> SEQ ID NO 98
<211> LENGTH: 40
<212> TYPE: DNA
<213> ORGANISM: Artificial
<220> FEATURE:
<223> OTHER INFORMATION: Aptamer to NGF

<400> SEQUENCE: 98
ggguccugcu acguaguuuc cgucuacgug gcuguuaccc    40

<210> SEQ ID NO 99
<211> LENGTH: 82
<212> TYPE: DNA
<213> ORGANISM: Artificial
<220> FEATURE:
<223> OTHER INFORMATION: Aptamer to NGF

<400> SEQUENCE: 99
gggagaacuu cgaccagaag uccaaacggg acuuuauacc ucgagucgc cuuugcuccu    60 augugcgcau acauggaucc uc    82

<210> SEQ ID NO 100
<211> LENGTH: 81
<212> TYPE: DNA
<213> ORGANISM: Artificial
<220> FEATURE:
<223> OTHER INFORMATION: Aptamer to NGF

<400> SEQUENCE: 100
gggagaacuu cgaccagaag accaaacgga cuuuauaccu cgagucgcc uaugcuccua    60 ugugcgcaua cauggauccu c    81

<210> SEQ ID NO 101
<211> LENGTH: 40
<212> TYPE: DNA
<213> ORGANISM: Artificial
<220> FEATURE:
<223> OTHER INFORMATION: Aptamer to NGF

<400> SEQUENCE: 101
ggguccugac guauaguuuc cgucuguaug ucuguuaccc    40

<210> SEQ ID NO 102
<211> LENGTH: 40
<212> TYPE: DNA
<213> ORGANISM: Artificial
<220> FEATURE:
<223> OTHER INFORMATION: Aptamer to NGF

```
<400> SEQUENCE: 102 gguccugag caagaguuuc cgucucaugc ucuguuaccc                              40

<210> SEQ ID NO 103
<211> LENGTH: 40
<212> TYPE: DNA
<213> ORGANISM: Artificial
<220> FEATURE:
<223> OTHER INFORMATION: Aptamer to NGF

<400> SEQUENCE: 103
ggguccugcu gcguaguuuc cgucugcgug guuguuaccc                             40

<210> SEQ ID NO 104
<211> LENGTH: 40
<212> TYPE: DNA
<213> ORGANISM: Artificial
<220> FEATURE:
<223> OTHER INFORMATION: Aptamer to NGF

<400> SEQUENCE: 104
ggguccugau gucaaguuuc cgucuugaug ucuguuaccc                             40

<210> SEQ ID NO 105
<211> LENGTH: 40
<212> TYPE: DNA
<213> ORGANISM: Artificial
<220> FEATURE:
<223> OTHER INFORMATION: Aptamer to NGF

<400> SEQUENCE: 105
ggguccuguu gcuaaguuuc cgucuuagug acuguuaccc                             40

<210> SEQ ID NO 106
<211> LENGTH: 40
<212> TYPE: DNA
<213> ORGANISM: Artificial
<220> FEATURE:
<223> OTHER INFORMATION: Aptamer to NGF

<400> SEQUENCE: 106
ggguccugcu gcguaguuuc cgucugcgua gcuguuaccc                             40

<210> SEQ ID NO 107
<211> LENGTH: 40
<212> TYPE: DNA
<213> ORGANISM: Artificial
<220> FEATURE:
<223> OTHER INFORMATION: Aptamer to NGF

<400> SEQUENCE: 107
ggguccugcu gcgaaguuuc cgucuucgug gcuguuaccc                             40

<210> SEQ ID NO 108
<211> LENGTH: 40
<212> TYPE: DNA
<213> ORGANISM: Artificial
<220> FEATURE:
<223> OTHER INFORMATION: Aptamer to NGF

<400> SEQUENCE: 108
ggguccuguu gcguaguuuc cgucugcgug acuguuaccc                             40

<210> SEQ ID NO 109
```

```
<211> LENGTH: 40
<212> TYPE: DNA
<213> ORGANISM: Artificial
<220> FEATURE:
<223> OTHER INFORMATION: Aptamer to NGF

<400> SEQUENCE: 109
ggguccugcu gcguaguuuc cuucugcgug gcuguuaccc                                40

<210> SEQ ID NO 110
<211> LENGTH: 40
<212> TYPE: DNA
<213> ORGANISM: Artificial
<220> FEATURE:
<223> OTHER INFORMATION: Aptamer to NGF

<400> SEQUENCE: 110
ggguccugcc gcguaguuuc cgucugcgug gcuguuaccc                                40

<210> SEQ ID NO 111
<211> LENGTH: 40
<212> TYPE: DNA
<213> ORGANISM: Artificial
<220> FEATURE:
<223> OTHER INFORMATION: Aptamer to NGF

<400> SEQUENCE: 111
ggguccuguc uaagaguuuc cgucucguag acuguuaccc                                40

<210> SEQ ID NO 112
<211> LENGTH: 40
<212> TYPE: DNA
<213> ORGANISM: Artificial
<220> FEATURE:
<223> OTHER INFORMATION: Aptamer to NGF

<400> SEQUENCE: 112
ggguccuguu caagaguuuc cgucucgugg acuguuaccc                                40

<210> SEQ ID NO 113
<211> LENGTH: 40
<212> TYPE: DNA
<213> ORGANISM: Artificial
<220> FEATURE:
<223> OTHER INFORMATION: Aptamer to NGF

<400> SEQUENCE: 113
ggguccugcu guguaguuuc cgucugcaug guuguuaccc                                40

<210> SEQ ID NO 114
<211> LENGTH: 40
<212> TYPE: DNA
<213> ORGANISM: Artificial
<220> FEATURE:
<223> OTHER INFORMATION: Aptamer to NGF

<400> SEQUENCE: 114
ggguccugac aaagaguuuc cgucucguug ucuguuaccc                                40

<210> SEQ ID NO 115
<211> LENGTH: 40
<212> TYPE: DNA
<213> ORGANISM: Artificial
<220> FEATURE:
<223> OTHER INFORMATION: Aptamer to NGF

<400> SEQUENCE: 115
```
ggguccuguc uaagaguuuc cgucucguag acuguuaccc    40

<210> SEQ ID NO 116
<211> LENGTH: 40
<212> TYPE: DNA
<213> ORGANISM: Artificial
<220> FEATURE:
<223> OTHER INFORMATION: Aptamer to NGF

<400> SEQUENCE: 116
ggguccuguu caagaguuuc cgucucguga acuguuaccc    40

<210> SEQ ID NO 117
<211> LENGTH: 40
<212> TYPE: DNA
<213> ORGANISM: Artificial
<220> FEATURE:
<223> OTHER INFORMATION: Aptamer to NGF

<400> SEQUENCE: 117
ggguccuguu gaagaguuuc cgucucguca acuguuaccc    40

<210> SEQ ID NO 118
<211> LENGTH: 83
<212> TYPE: DNA
<213> ORGANISM: Artificial
<220> FEATURE:
<223> OTHER INFORMATION: DNA template
<220> FEATURE:
<221> NAME/KEY: misc_feature
<222> LOCATION: (24)..(63)
<223> OTHER INFORMATION: n is a, c, g, or t

<400> SEQUENCE: 118
gaggatccat gtatgcgcac atannnnnnn nnnnnnnnnn nnnnnnnnnn nnnnnnnnnn    60
nnncttctgg tcgaagttct ccc    83

<210> SEQ ID NO 119
<211> LENGTH: 45
<212> TYPE: DNA
<213> ORGANISM: Artificial
<220> FEATURE:
<223> OTHER INFORMATION: primer

<400> SEQUENCE: 119
cggaattcta atacgactca ctatagggag aacttcgacc agaag    45

<210> SEQ ID NO 120
<211> LENGTH: 23
<212> TYPE: DNA
<213> ORGANISM: Artificial
<220> FEATURE:
<223> OTHER INFORMATION: primer

<400> SEQUENCE: 120
gaggatccat gtatgcgcac ata    23

<210> SEQ ID NO 121
<211> LENGTH: 44
<212> TYPE: DNA
<213> ORGANISM: Artificial
<220> FEATURE:
<223> OTHER INFORMATION: Aptamer to NGF

<400> SEQUENCE: 121
gggcacaucc ugcgcguagu uuccgucucc gugcuguuau gugc         44

<210> SEQ ID NO 122
<211> LENGTH: 44
<212> TYPE: DNA
<213> ORGANISM: Artificial
<220> FEATURE:
<223> OTHER INFORMATION: Aptamer to NGF

<400> SEQUENCE: 122
gggcacaucc ugcugcgagu uuccgucucg uggcuguuau gugc         44

<210> SEQ ID NO 123
<211> LENGTH: 44
<212> TYPE: DNA
<213> ORGANISM: Artificial
<220> FEATURE:
<223> OTHER INFORMATION: Aptamer to NGF

<400> SEQUENCE: 123
gggcacaucc ugugcguagu uuccgucucc gugcuguuau gugc         44

<210> SEQ ID NO 124
<211> LENGTH: 44
<212> TYPE: DNA
<213> ORGANISM: Artificial
<220> FEATURE:
<223> OTHER INFORMATION: Aptamer to NGF

<400> SEQUENCE: 124
gggcacaucc ugcugguagu uuccgucucc uggcuguuau gugc         44

<210> SEQ ID NO 125
<211> LENGTH: 44
<212> TYPE: DNA
<213> ORGANISM: Artificial
<220> FEATURE:
<223> OTHER INFORMATION: Aptamer to NGF

<400> SEQUENCE: 125
gggcacaucc ugcugcuagu uuccgucucg uggcuguuau gugc         44

<210> SEQ ID NO 126
<211> LENGTH: 44
<212> TYPE: DNA
<213> ORGANISM: Artificial
<220> FEATURE:
<223> OTHER INFORMATION: Aptamer to NGF

<400> SEQUENCE: 126
gggcacaucc ugcugcgugu uuccgucccg uggcuguuau gugc         44

<210> SEQ ID NO 127
<211> LENGTH: 40
<212> TYPE: DNA
<213> ORGANISM: Artificial
<220> FEATURE:
<223> OTHER INFORMATION: Aptamer to NGF

<400> SEQUENCE: 127
gggguccucu gcguaguuuc cgucccgug guguuacccc               40

<210> SEQ ID NO 128
<211> LENGTH: 40
<212> TYPE: DNA
<213> ORGANISM: Artificial

```
<220> FEATURE:
<223> OTHER INFORMATION: Aptamer to NGF

<400> SEQUENCE: 128
gggguccugc ugcguauuuc cguuccgugg cuguuacccc                          40

<210> SEQ ID NO 129
<211> LENGTH: 40
<212> TYPE: DNA
<213> ORGANISM: Artificial
<220> FEATURE:
<223> OTHER INFORMATION: Aptamer to NGF

<400> SEQUENCE: 129
ggggccugcu gcguaguuuc cgucccgug gcuguuccc                            40

<210> SEQ ID NO 130
<211> LENGTH: 45
<212> TYPE: DNA
<213> ORGANISM: Artificial
<220> FEATURE:
<223> OTHER INFORMATION: Aptamer to NGF

<400> SEQUENCE: 130
gggcacaucc ugcugcguag uuccgucucc guggcuguua ugugc                    45

<210> SEQ ID NO 131
<211> LENGTH: 44
<212> TYPE: DNA
<213> ORGANISM: Artificial
<220> FEATURE:
<223> OTHER INFORMATION: Aptamer to NGF

<400> SEQUENCE: 131
gggcacaucc ugcugcguag uuugucuccg uggcuguuau gugc                     44

<210> SEQ ID NO 132
<211> LENGTH: 45
<212> TYPE: DNA
<213> ORGANISM: Artificial
<220> FEATURE:
<223> OTHER INFORMATION: Aptamer to NGF

<400> SEQUENCE: 132
gggcacaucc ugcugcguag uuccucucc guggcuguua ugugc                     45

<210> SEQ ID NO 133
<211> LENGTH: 41
<212> TYPE: DNA
<213> ORGANISM: Artificial
<220> FEATURE:
<223> OTHER INFORMATION: Aptamer to NGF

<400> SEQUENCE: 133
gggguccugc ugcguaguuu ccgcuccgug gcuguuaccc c                        41

<210> SEQ ID NO 134
<211> LENGTH: 45
<212> TYPE: DNA
<213> ORGANISM: Artificial
<220> FEATURE:
<223> OTHER INFORMATION: Aptamer to NGF

<400> SEQUENCE: 134
gggcacaucc ugcugcguag uuuccgucuc cguggcugua ugugc                    45
```

```
<210> SEQ ID NO 135
<211> LENGTH: 41
<212> TYPE: DNA
<213> ORGANISM: Artificial
<220> FEATURE:
<223> OTHER INFORMATION: Aptamer to NGF

<400> SEQUENCE: 135
ggggucugcu gcguaguuuc cgucuccgug gcuguuaccc c                           41

<210> SEQ ID NO 136
<211> LENGTH: 41
<212> TYPE: DNA
<213> ORGANISM: Artificial
<220> FEATURE:
<223> OTHER INFORMATION: Aptamer to NGF

<400> SEQUENCE: 136
gggguccgcu gcguaguuuc cgucuccgug gcuguuaccc c                           41

<210> SEQ ID NO 137
<211> LENGTH: 40
<212> TYPE: DNA
<213> ORGANISM: Artificial
<220> FEATURE:
<223> OTHER INFORMATION: Aptamer to NGF

<400> SEQUENCE: 137
ggggucugcu gcguaguuuc cgucuccgug gcuguacccc                             40

<210> SEQ ID NO 138
<211> LENGTH: 40
<212> TYPE: DNA
<213> ORGANISM: Artificial
<220> FEATURE:
<223> OTHER INFORMATION: Aptamer to NGF

<400> SEQUENCE: 138
ggggucugcu gcguaguuuc cgucuccgug gcuuuacccc                             40

<210> SEQ ID NO 139
<211> LENGTH: 40
<212> TYPE: DNA
<213> ORGANISM: Artificial
<220> FEATURE:
<223> OTHER INFORMATION: Aptamer to NGF

<400> SEQUENCE: 139
gggguccgcu gcguaguuuc cgucuccgug gcguuacccc                             40

<210> SEQ ID NO 140
<211> LENGTH: 40
<212> TYPE: DNA
<213> ORGANISM: Artificial
<220> FEATURE:
<223> OTHER INFORMATION: Aptamer to NGF

<400> SEQUENCE: 140
gggguccgcu gcguaguuuc cgucuccgug gcuuuacccc                             40

<210> SEQ ID NO 141
<211> LENGTH: 40
<212> TYPE: DNA
<213> ORGANISM: Artificial
<220> FEATURE:
<223> OTHER INFORMATION: Aptamer to NGF
```

```
-continued

<400> SEQUENCE: 141
gggguccgcu gcguaguuuc cgucuccgug gcuguacccc                         40

<210> SEQ ID NO 142
<211> LENGTH: 79
<212> TYPE: DNA
<213> ORGANISM: Artificial
<220> FEATURE:
<223> OTHER INFORMATION: DNA template
<220> FEATURE:
<221> NAME/KEY: misc_feature
<222> LOCATION: (21)..(60)
<223> OTHER INFORMATION: n is a, c, g, or t

<400> SEQUENCE: 142
ccagttgttg gtgacaatgc nnnnnnnnnn nnnnnnnnnn nnnnnnnnnn nnnnnnnnnn   60
gcagctccac aggcttccc                                                79

<210> SEQ ID NO 143
<211> LENGTH: 36
<212> TYPE: DNA
<213> ORGANISM: Artificial
<220> FEATURE:
<223> OTHER INFORMATION: primer

<400> SEQUENCE: 143
taatacgact cactataggg aagcctgtgg agctgc                             36

<210> SEQ ID NO 144
<211> LENGTH: 20
<212> TYPE: DNA
<213> ORGANISM: Artificial
<220> FEATURE:
<223> OTHER INFORMATION: primer

<400> SEQUENCE: 144
gcattgtcac caacaactgg                                               20

<210> SEQ ID NO 145
<211> LENGTH: 83
<212> TYPE: DNA
<213> ORGANISM: Artificial
<220> FEATURE:
<223> OTHER INFORMATION: DNA template

<400> SEQUENCE: 145
gaggatccat gtatgcgcac ataacagcca cggagacgga aactacgcag caggatgtgc   60
caacttctgg tcgaagttct ccc                                           83

<210> SEQ ID NO 146
<211> LENGTH: 22
<212> TYPE: DNA
<213> ORGANISM: Artificial
<220> FEATURE:
<223> OTHER INFORMATION: oligo DNA

<400> SEQUENCE: 146
agacggaaac tacgcagcag ga                                            22

<210> SEQ ID NO 147
<211> LENGTH: 83
<212> TYPE: DNA
<213> ORGANISM: Artificial
<220> FEATURE:
```

```
<223> OTHER INFORMATION: DNA template
<220> FEATURE:
<221> NAME/KEY: misc_feature
<222> LOCATION: (28)..(34)
<223> OTHER INFORMATION: n is a, c, g, or t
<220> FEATURE:
<221> NAME/KEY: misc_feature
<222> LOCATION: (44)..(50)
<223> OTHER INFORMATION: n is a, c, g, or t

<400> SEQUENCE: 147
gaggatccat gtatgcgcac ataacagnnn nnnngacgga aacnnnnnnn caggatgtgc    60
caacttctgg tcgaagttct ccc                                           83

<210> SEQ ID NO 148
<211> LENGTH: 83
<212> TYPE: DNA
<213> ORGANISM: Artificial
<220> FEATURE:
<223> OTHER INFORMATION: DNA template
<220> FEATURE:
<221> NAME/KEY: misc_feature
<222> LOCATION: (23)..(26)
<223> OTHER INFORMATION: n is a, c, g, or t
<220> FEATURE:
<221> NAME/KEY: misc_feature
<222> LOCATION: (36)..(42)
<223> OTHER INFORMATION: n is a, c, g, or t
<220> FEATURE:
<221> NAME/KEY: misc_feature
<222> LOCATION: (52)..(54)
<223> OTHER INFORMATION: n is a, c, g, or t

<400> SEQUENCE: 148
gaggatccat gtatgcgcac atnnnnggat acgagnnnnn nnctcttatc cnnnatgtgc    60
caacttctgg tcgaagttct ccc                                           83

<210> SEQ ID NO 149
<211> LENGTH: 45
<212> TYPE: DNA
<213> ORGANISM: Artificial
<220> FEATURE:
<223> OTHER INFORMATION: primer

<400> SEQUENCE: 149
taatacgact cactataggg agaacttcga ccagaagttg gcaca                   45

<210> SEQ ID NO 150
<211> LENGTH: 21
<212> TYPE: DNA
<213> ORGANISM: Artificial
<220> FEATURE:
<223> OTHER INFORMATION: primer

<400> SEQUENCE: 150
gaggatccat gtatgcgcac a                                             21

<210> SEQ ID NO 151
<211> LENGTH: 40
<212> TYPE: DNA
<213> ORGANISM: Artificial
<220> FEATURE:
<223> OTHER INFORMATION: Aptamer to NGF

<400> SEQUENCE: 151
ggguccugcu gcguaguuuc cgucugcgug gcguuaccc                          40
```

```
<210> SEQ ID NO 152
<211> LENGTH: 40
<212> TYPE: DNA
<213> ORGANISM: Artificial
<220> FEATURE:
<223> OTHER INFORMATION: Aptamer to NGF

<400> SEQUENCE: 152
ggguccugcu gcguaguuuc cgucugcgug gcuguuaccc                    40

<210> SEQ ID NO 153
<211> LENGTH: 40
<212> TYPE: DNA
<213> ORGANISM: Artificial
<220> FEATURE:
<223> OTHER INFORMATION: Aptamer to NGF

<400> SEQUENCE: 153
ggguccugcu gcguaguuuc cgucugcgug gcuguuaccc                    40

<210> SEQ ID NO 154
<211> LENGTH: 40
<212> TYPE: DNA
<213> ORGANISM: Artificial
<220> FEATURE:
<223> OTHER INFORMATION: Aptamer to NGF

<400> SEQUENCE: 154
ggguccugcu gcguaguuuc cgucugcgug gcuguuaccc                    40

<210> SEQ ID NO 155
<211> LENGTH: 40
<212> TYPE: DNA
<213> ORGANISM: Artificial
<220> FEATURE:
<223> OTHER INFORMATION: Aptamer to NGF

<400> SEQUENCE: 155
ggguccugcu gcgcaguuuc cgucuacgug gcuguuaccc                    40

<210> SEQ ID NO 156
<211> LENGTH: 40
<212> TYPE: DNA
<213> ORGANISM: Artificial
<220> FEATURE:
<223> OTHER INFORMATION: Aptamer to NGF

<400> SEQUENCE: 156
ggguccugga uaagagtuuc cgucucguau ccuguuaccc                    40

<210> SEQ ID NO 157
<211> LENGTH: 40
<212> TYPE: DNA
<213> ORGANISM: Artificial
<220> FEATURE:
<223> OTHER INFORMATION: Aptamer to NGF

<400> SEQUENCE: 157
ggguccugga uaagagutuc cgucucguau ccuguuaccc                    40

<210> SEQ ID NO 158
<211> LENGTH: 40
<212> TYPE: DNA
<213> ORGANISM: Artificial
<220> FEATURE:
<223> OTHER INFORMATION: Aptamer to NGF
```

```
<400> SEQUENCE: 158 gguccugga uaagaguuuc cgucucguau cctguuaccc                  40

<210> SEQ ID NO 159
<211> LENGTH: 40
<212> TYPE: DNA
<213> ORGANISM: Artificial
<220> FEATURE:
<223> OTHER INFORMATION: Aptamer to NGF

<400> SEQUENCE: 159
ggguccugga uaagaguuuc cgucucguau ccugtuaccc                 40

<210> SEQ ID NO 160
<211> LENGTH: 40
<212> TYPE: DNA
<213> ORGANISM: Artificial
<220> FEATURE:
<223> OTHER INFORMATION: Aptamer to NGF

<400> SEQUENCE: 160
ggguccugga uaagagtuuc cgucucguau ccuguuaccc                 40

<210> SEQ ID NO 161
<211> LENGTH: 40
<212> TYPE: DNA
<213> ORGANISM: Artificial
<220> FEATURE:
<223> OTHER INFORMATION: Aptamer to NGF

<400> SEQUENCE: 161
ggguccugga uaagaguuuc cgucucguau cctguuaccc                 40

<210> SEQ ID NO 162
<211> LENGTH: 40
<212> TYPE: DNA
<213> ORGANISM: Artificial
<220> FEATURE:
<223> OTHER INFORMATION: Aptamer to NGF

<400> SEQUENCE: 162
ggguccugga uaagagtuuc cgucucguau cctguuaccc                 40

<210> SEQ ID NO 163
<211> LENGTH: 40
<212> TYPE: DNA
<213> ORGANISM: Artificial
<220> FEATURE:
<223> OTHER INFORMATION: Aptamer to NGF

<400> SEQUENCE: 163
ggguccugga uaagagtuuc cgucucguau cctguuaccc                 40

<210> SEQ ID NO 164
<211> LENGTH: 40
<212> TYPE: DNA
<213> ORGANISM: Artificial
<220> FEATURE:
<223> OTHER INFORMATION: Aptamer to NGF

<400> SEQUENCE: 164
ggguccugga uaagagtuuc cgucucguau cctguuaccc                 40

<210> SEQ ID NO 165
<211> LENGTH: 40
```

```
<212> TYPE: DNA
<213> ORGANISM: Artificial
<220> FEATURE:
<223> OTHER INFORMATION: Aptamer to NGF

<400> SEQUENCE: 165
ggguccugga uaagagtuuc cgucucguau cctguuaccc                          40

<210> SEQ ID NO 166
<211> LENGTH: 40
<212> TYPE: DNA
<213> ORGANISM: Artificial
<220> FEATURE:
<223> OTHER INFORMATION: Aptamer to NGF

<400> SEQUENCE: 166
ggguccugga uaagagtuuc cgucucguau cctguuaccc                          40

<210> SEQ ID NO 167
<211> LENGTH: 40
<212> TYPE: DNA
<213> ORGANISM: Artificial
<220> FEATURE:
<223> OTHER INFORMATION: Aptamer to NGF

<400> SEQUENCE: 167
ggguccugga uaagagtuuc cgucucguau cctguuaccc                          40

<210> SEQ ID NO 168
<211> LENGTH: 40
<212> TYPE: DNA
<213> ORGANISM: Artificial
<220> FEATURE:
<223> OTHER INFORMATION: Aptamer to NGF

<400> SEQUENCE: 168
ggguccugga uaagagtuuc cgucucguau cctguuaccc                          40
```

NGF APTAMER AND APPLICATION THEREOF

TECHNICAL FIELD

The present invention relates to an aptamer for NGF, and use thereof.

BACKGROUND ART

Nerve growth factor (NGF) is the first neurotrophin identified in 1951, and is an important secretory protein involved in the development and survival of peripheral and central neurons. It consists of 118 amino acids, has a molecular weight of 13 kDa, and has S—S bonds at 3 positions in a molecule.

As NGF receptors, tyrosine kinase-type receptor TrkA with high affinity and p75 with low affinity which belongs to a tumor necrosis factor receptor superfamily are known. These receptors act as a homodimer or heterodimer and are deeply involved in the development and maintenance of the nervous system. TrkA is a single-pass transmembrane receptor and has a tyrosine kinase structure in the intracellular domain. When NGF is bound, tyrosine phosphorylation occurs, the signal is transmitted to the downstream, and promotion of differentiation and survival maintenance of the cell occur.

As family receptors of TrkA, TrkB and TrkC are known. TrkB is bound to BDNF and NT-4/5, and TrkC is bound to NT-3. p75 shows lower ligand specificity as compared to TrkA and is also bound to BDNF, NT-3 and NT-4/5 besides NGF. While p75 is a single-pass transmembrane receptor, it does not have a tyrosine kinase domain on the cytoplasmic side. Like TrkA, it is expressed not only in nerve cells but also in non-nerve cells. This receptor is known to be involved in the promotion of differentiation and survival maintenance of the cell, as well as related to the induction of apoptosis and cell migration. The results of crystal structure analysis have suggested that an NGF homodimer binds to TrkA at 2:2 and to p75 at 2:1. An NGF homodimer sometimes binds to a heterodimer of TrkA and p75.

It is well known that NGF plays a key role in the nervous system. It has been clarified that NGF has an action to maintain survival of cholinergic neuron and is considered to be related in some way to Alzheimer's disease. In addition, since intracerebral administration of NGF improves memory disorders of old rats, it is also expected as a therapeutic drug for senile dementia.

NGF is also related to inflammation, and increased expression of NGF has been observed in patients with inflammatory diseases and inflammatory animal models. Systemic lupus erythematosus, multiple sclerosis, psoriasis, arthritis, interstitial cystitis, asthma and the like are the examples thereof. It has been reported that the synovial fluid of patients with rheumatoid arthritis shows higher NGF concentration. In addition, increased NGF expression in rheumatoid arthritis model rats, and increase in mast cells and increased NGF expression in arthritis model mouse have been reported.

NGF is deeply involved in pain. When NGF is subcutaneously administered to human, a deep pain such as muscular pain continues for several days, and hyperalgesia of the injection site occurs. NGF knockout mouse and TrkA knockout mouse lacks unmyelinated nerve and do not feel pain. When NGF is intraperitoneally administered at 1 mg/kg to a mature rat, hyperalgesia against noxious heat and mechanical stimuli occurs. NGF transgenic mouse shows hyperalgesia unaccompanied by inflammatory conditions. In addition, it is known that the TrkA gene of patients with congenital insensitivity to pain with anhidrosis (CIPA) has abnormality, and pain sensation decreases when NGF gene has abnormality.

From the above, it is appreciated that an NGF inhibitor can be used as a therapeutic drug for pain such as nociceptive pain, inflammatory pain, neuropathic pain, carcinomatous pain, fibromyalgia pain and the like.

In recent years, applications of RNA aptamers to medicaments, diagnostic agents, and test drugs have been drawing attention; some RNA aptamers have already been in clinical study stage or in practical use. In December 2004, the world's first RNA aptamer drug, Macugen, was approved as a therapeutic drug for age-related macular degeneration in the US. An RNA aptamer refers to an RNA that binds specifically to a target substance such as a protein, and can be prepared using the SELEX (Systematic Evolution of Ligands by Exponential Enrichment) method (Patent references 1-3). In the SELEX, an RNA that binds specifically to a target substance is selected from an RNA pool with about $10^{14}$ different nucleotide sequences. The RNA structure used has a random sequence of about 40 residues, which is flanked by primer sequences. This RNA pool is allowed to be assembled with a target substance, and only the RNA that has bound to the target substance is collected using a filter and the like. The RNA collected is amplified by RT-PCR, and this is used as a template for the next round. By repeating this operation about 10 times, an RNA aptamer that binds specifically to the target substance can be acquired.

Aptamer drugs, like antibody drugs, can target extracellular factors. With reference to many scientific papers and other reference materials in the public domain, aptamer drugs are judged to potentially surpass antibody drugs in some aspects. For example, aptamers often show higher binding force and higher specificity than do antibodies. Aptamers are unlikely to undergo immune elimination, and adverse reactions characteristic of antibodies, such as antibody-dependent cell-mediated cytotoxicity (ADCC) and complement-dependent cytotoxicity (CDC), do not occur with the use of aptamers. From the aspect of delivery, since aptamers are about 1/10 of antibody in size, delivery of a drug to the object site is easier. Since aptamers are produced by chemical synthesis, various modifications can be made easily, reduction of cost by large-scale production is possible. Meanwhile, the blood half-lives of aptamers are generally shorter than those of antibodies; however, this property is sometimes advantageous in view of toxicity. These facts lead to the conclusion that even when the same molecule is targeted, aptamer drugs potentially surpass antibody drugs.

The present inventors have produced an aptamer which binds to NGF and inhibits binding of NGF and an NGF receptor, and found that the aptamer inhibits a neurite outgrowth activity of NGF (patent document 4). Patent document 5 describes an aptamer to NGF, which is obtained by automated SELEX, and patent document 6 describes an altered product and a modified product of the aptamer obtained in patent document 4.

DOCUMENT LIST

Patent Documents patent document 1: WO91/19813
patent document 2: WO94/08050 patent document 3: WO95/07364
patent document 4: WO2010/035725
patent document 5: WO02/077262
patent document 6: WO03/070984

SUMMARY OF THE INVENTION

Problems to be Solved by the Invention

The present invention aims to provide an aptamer for NGF, a method of utilizing the same, and the like. Particularly, the present invention aims to provide an NGF aptamer suitable for use as a pharmaceutical product, namely, an aptamer having a short chain length, a high NGF activity (neurite outgrowth activity, TF-1 cell proliferation activity) inhibitory activity, and high specificity for NGF.

Means of Solving the Problems

The present inventors have conducted intensive studies in an attempt to solve the aforementioned problems and succeeded in producing a higher quality NGF aptamer showing an $IC_{50}$ value of 1 nM or below as to neurite outgrowth inhibition, and a remarkably high neurite outgrowth inhibitory activity as compared to conventionally-known NGF aptamers, which resulted in the completion of the present invention.

Accordingly, the present invention provides the following.

[1] An aptamer binding to NGF and capable of forming a potential secondary structure represented by the formula (I):

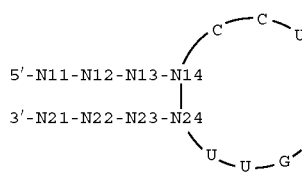 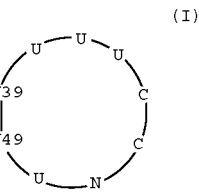

(I)

wherein N is one nucleotide selected from the group consisting of A, G, C, U and T, N11-N13, N21-N23, N32-N38 and N42-N48 are the same or different and each is a bond or 1 or 2 nucleotides selected from the group consisting of A, G, C, U and T, N14, N24, N31, N41, N39 and N49 are the same or different and each is one nucleotide selected from the group consisting of A, G, C, U and T, N14 and N24, N31 and N41, and N39 and N49 each form a Watson-Crick base pair, N11-N12-N13-N14 and N21-N22-N23-N24 are nucleotide sequences capable of forming a stem structure in combination, and N31-N32-N33-N34-N35-N36-N37-N38-N39 and N41-N42-N43-N44-N45-N46-N47-N48-N49 are nucleotide sequences capable of forming a stem structure in combination.

[2] The aptamer according to the above-mentioned [1], wherein N11-N13, N21-N23, N32-N38 and N42-N48 are the same or different and each is one nucleotide selected from the group consisting of A, G, C, U and T.

[3] The aptamer according to the above-mentioned [1] or [2], wherein N14 is U, N24 is A, N31 is G, N41 is C, N39 is G, and N49 is C.

[4] The aptamer according to any of the above-mentioned [1] to [3], wherein not less than 4 Watson-Crick base pairs are formed between N32-N33-N34-N35-N36-N37-N38 and N42-N43-N44-N45-N46-N47-N48.

[5] The aptamer according to the above-mentioned [1], which is the following (a) or (b):

(a) a nucleic acid consisting of a nucleotide sequence selected from SEQ ID NO: 3, SEQ ID NOs: 9-13, SEQ ID NOs: 22-117 and SEQ ID NOs: 152-168 (wherein uracil may be thymine);

(b) a nucleic acid binding to NGF and consisting of the nucleotide sequence of the above-mentioned (a), wherein 1 to several nucleotides are substituted, deleted, inserted or added.

[6] The aptamer according to any of the above-mentioned [1] to [5], which has a base length of not more than 50.

[7] The aptamer according to any of the above-mentioned [1] to [6], wherein at least one nucleotide is modified.

[8] The aptamer according to the above-mentioned [7], which is modified with inverted dT or polyethylene glycol.

[9] The aptamer according to the above-mentioned [8], wherein the inverted dT or polyethylene glycol is bound to the 5' end or 3' end of the aptamer.

[10] The aptamer according to any of the above mentioned [7] to [9], wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group.

[11] The aptamer according to any of the above-mentioned [7] to [9], wherein the hydroxyl groups at the 2'-position of a ribose of respective purine nucleotides are the same or different and unreplaced or replaced by an atom or group selected from the group consisting of a hydrogen atom, a fluorine atom and a methoxy group.

[12] The aptamer according to any of the above-mentioned [1] to [11], which inhibits neurite outgrowth activity and/or cell proliferation activity of NGF.

[13] A pharmaceutical composition comprising the aptamer according to any of the above-mentioned [1] to [12].

[14] An anti-pain agent comprising the aptamer according to any of the above-mentioned [1] to [12].

[15] An anti-inflammatory agent comprising the aptamer according to any of the above-mentioned [1] to [12].

[16] A method of treating or preventing a disease accompanying a pain or inflammation, comprising administering the aptamer according to any of the above-mentioned [1] to [12] to a subject in need thereof.

[17] The aptamer according to any of the above-mentioned [1] to [12] for the prophylaxis or treatment of a disease accompanying a pain or inflammation.

Effect of the Invention

Since the aptamer or nucleic acid of the present invention shows a superior NGF inhibitory activity, particularly a high neurite outgrowth inhibitory activity, due to the above-mentioned constitution, it can be useful as a medicament for diseases such as algia, inflammatory disease and the like.

DESCRIPTION OF EMBODIMENTS

Figure 1:
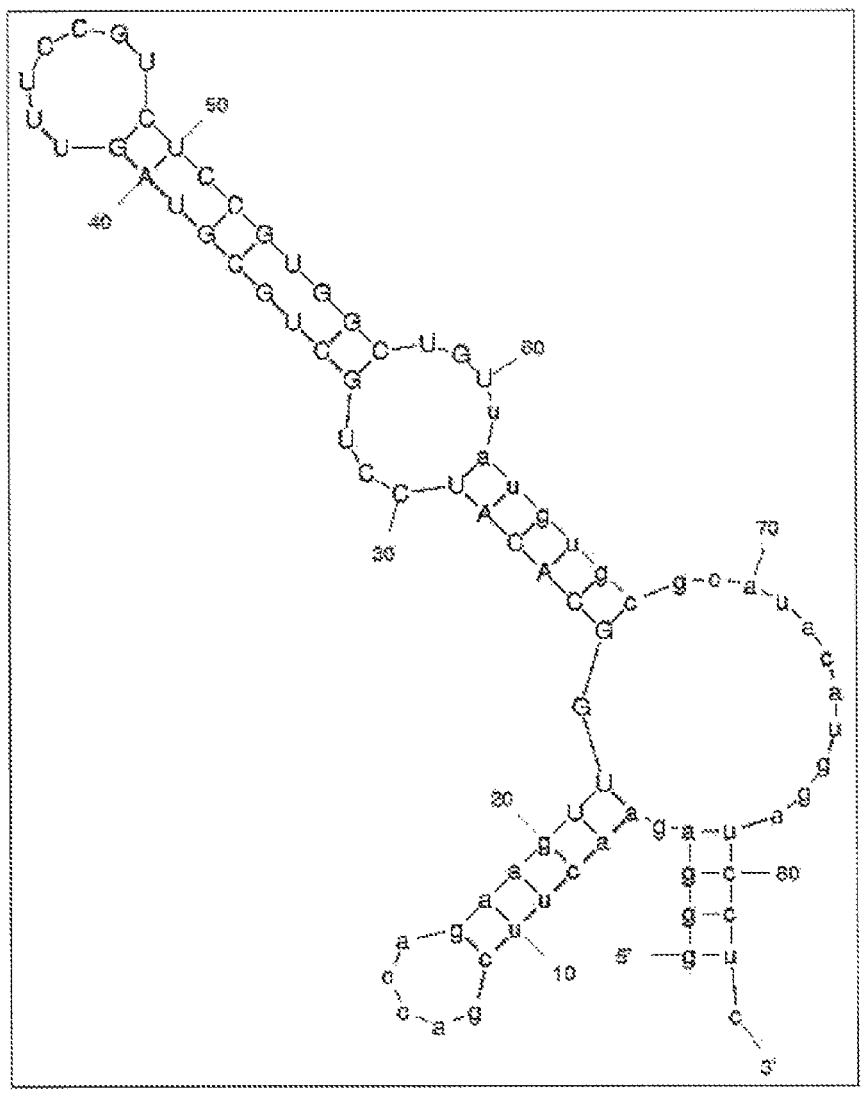
FIG. 1 is a schematic diagram of a predictable secondary structure of the NGF aptamer shown by SEQ ID NO: 3, wherein the stem-loop structure on the upper left side corresponds to a consensus secondary structure 1.

The present invention provides an aptamer binding to NGF and capable of forming a potential secondary structure represented by the formula (I):

aptamer of the present invention is an aptamer having a binding activity to NGF. According to preferable embodiment, the aptamer of the present invention can inhibit the activity of NGF by binding to NGF and inhibiting the binding of NGF and NGF receptor.

The aptamer of the present invention can be a nucleic acid such as an RNA, a DNA, a modified nucleic acid or a mixture thereof. Accordingly, the aptamer of the present invention may be indicated as "the nucleic acid of the present invention" in the following.

The single-stranded nucleic acid can have various secondary structures. The "potential secondary structure" means a secondary structure that a certain single-stranded nucleic acid can take thermodynamically in view of its primary structure. Particularly, the potential secondary structure of the aptamer of the present invention is a secondary structure predictable using the MFOLD program described in Example 5. Accordingly, even a nucleic acid not currently having a secondary structure represented by the above-mentioned formula (I) is encompassed in the aptamer of the present invention, as long as it has a primary structure capable of forming said secondary structure.

Therefore, preferably, the aptamer of the present invention is a nucleic acid molecule capable of having a secondary structure represented by the above-mentioned formula (I) thermodynamically stably in view of the primary structure thereof. In this sense, the aptamer of the present invention is an aptamer capable of forming a potential secondary structure represented by the formula (I).

The potential secondary structure represented by the formula (I) is what is called a "stem-loop structure", which

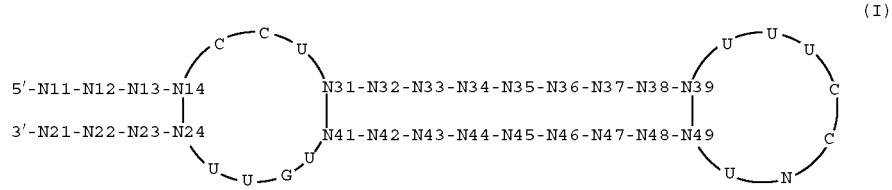

(I)

wherein N is one nucleotide selected from the group consisting of A, G, C, U and T, N11-N13, N21-N23, N32-N38 and N42-N48 are the same or different and each is a bond or 1 or 2 nucleotides selected from the group consisting of A, G, C, U and T, N14, N24, N31, N41, N39 and N49 are the same or different and each is one nucleotide selected from the group consisting of A, G, C, U and T, N14 and N24, N31 and N41, and N39 and N49 each form a Watson-Crick base pair, N11-N12-N13-N14 and N21-N22-N23-N24 are nucleotide sequences capable of forming a stem structure in combination, and N31-N32-N33-N34-N35-N36-N37-N38-N39 and N41-N42-N43-N44-N45-N46-N47-N48-N49 are nucleotide sequences capable of forming a stem structure in combination (hereinafter to be described as "the aptamer of the present invention"). The above-mentioned nucleotide sequence is optionally modified as mentioned below.

An aptamer refers to a nucleic acid molecule having a binding activity for a particular target molecule. The aptamer can inhibit the activity of a particular target molecule by binding to the particular target molecule. The is particularly a structure having a loop structure (to be described as "internal loop 1" in the present Description) between the stem structure that can be formed by a combination of N11-N12-N13-N14 and N21-N22-N23-N24, and the stem structure that can be formed by a combination of N31-N32-N33-N34-N35-N36-N37-N38-N39 and N41-N42-N43-N44-N45-N46-N47-N48-N49, and further, a loop structure between N39 and N49 (to be described as "loop 2" in the present Description).

The "stem structure" is a structure wherein partial nucleotide sequences having complementarity in a nucleic acid molecule form Watson-Crick base pairs (G-C or A-U/T). In the present Description, N11-N12-N13-N14 and N21-N22-N23-N24, and N31-N32-N33-N34-N35-N36-N37-N38-N39 and N41-N42-N43-N44-N45-N46-N47-N48-N49 do not need to be completely complementary, and mismatch and/or wobbling of G-U/T are/is permitted. That is, as long as the nucleotides on the both ends of a partial nucleotide sequence forming a stem structure form Watson-Crick base pairs, all other nucleotides are not necessarily required to form Watson-Crick base pairs.

In the formula (I), "N" positioned in the loop 2 section is one nucleotide selected from the group consisting of A, G, C, U and T. In a preferable embodiment, "N" can be G.

In the formula (I), N11-N13, N21-N23, N32-N38 and N42-N48 are the same or different and each is a bond or 1 or 2 nucleotides selected from the group consisting of A, G, C, U and T. When Ni (i is an integer selected from 11-13, 21-23, 32-38, 42-48) shows "two nucleotides", said two nucleotides may be the same or different. When Ni shows "two nucleotides" or "a bond", it is preferably contained in each partial sequence of N11-N13, N21-N23, N32-N38 and N42-N48 in the number of not more than 2, more preferably not more than 1. Therefore, each of N11-N14 and N21-N24 forming one stem structure preferably has a nucleotide length of 2-6, more preferably 3-5, and each of N31-N39 and N41-N49 forming the other stem structure preferably has a nucleotide length of preferably 7-11, more preferably 8-10.

The above-mentioned "bond" means a single bond, and when any Ni in the formula (I) is "a bond", it means that the nucleotides adjacent to the nucleotide are linked to each other via a phosphodiester bond.

Particularly preferably, N11-N13, N21-N23, N32-N38 and N42-N48 are the same or different and each is one nucleotide selected from the group consisting of A, G, C, U and T. Therefore, the stem structure including the both ends of the part forming the secondary structure has a stem length of preferably not more than 4 nucleotides, and the internal stem structure sandwiched between two loops has a stem length of preferably 9 nucleotides.

In the formula (I), N14, N24, N31, N41, N39 and N49 are the same or different and each is one nucleotide selected from the group consisting of A, G, C, U and T, and N14 and N24, N31 and N41, and N39 and N49 each form a Watson-Crick base pair (G-C or A-U/T). Therefore, a stem structure containing the both ends of the part forming the secondary structure forms a base pair at least at the end on the side of the internal loop 1 section, and the internal stem structure sandwiched between the two loops forms base pairs at the both ends thereof. More preferably, N14 is U, N24 is A, N31 is G, N41 is C, N39 is G, and N49 is C.

On the other hand, as defined above, N11-N12-N13 and N21-N22-N23, and N32-N33-N34-N35-N36-N37-N38 and N42-N43-N44-N45-N46-N47-N48 in the "stem structure" do not need to be completely complementary (formation of Watson-Crick base pairs by all of them is not necessary). However, complementarity of the level enabling formation of a stem structure (loop (bubble) is not formed in the stem) is necessary. To be specific, since a loop can be formed when 3 continuous mismatches or wobblings of G-U/T are contained in each stem structure, each stem structure is desirably free of 3 continuous mismatches or wobblings of G-U/T. It is also desirable that not less than 50%, preferably not less than 60%, more preferably not less than 70%, of each of N11-N12-N13 and N21-N22-N23, and N32-N33-N34-N35-N36-N37-N38 and N42-N43-N44-N45-N46-N47-N48 be nucleotides that form Watson-Crick base pairs.

The present invention also provides a nucleic acid consisting of the nucleotide sequence of the following (a) or (b):
(a) a nucleotide sequence selected from SEQ ID NO: 3, SEQ ID NOs: 9-13, SEQ ID NOs: 22-117 and SEQ ID NOs: 152-168 (wherein uracil may be thymine);
(b) the nucleotide sequence of the above-mentioned (a) and binding to NGF, wherein 1 to several nucleotides are substituted, deleted, inserted or added.

Such nucleic acids can form a potential secondary structure represented by the above-mentioned formula (I).

While any uracil on any sequence can be replaced by thymine, the uracil to be replaced can be preferably one in a part other than the internal loop 1 section and loop 2 section in the aforementioned potential secondary structure, so that the activity of the aptamer of the present invention can be maintained.

In the present Description, a sequence specified by "SEQ ID NO" means a nucleotide sequence of each aptamer or nucleic acid and, for example, "a nucleic acid comprising the sequence shown by SEQ ID NO: 1" means a natural nucleic acid or modified nucleic acid comprising the sequence shown by SEQ ID NO: 1 or a nucleic acid constituted with the both. The base sequence of SEQ ID NO of each aptamer is described in the Sequence Listing.

In the above-mentioned (b), the number of the nucleotides substituted, deleted, inserted or added is, for example, about 1-10, preferably 1-6, more preferably 1-5, further preferably 1-3, most preferably 1 or 2.

In the above-mentioned (b), while the position of the nucleotide to be substituted, deleted, inserted or added is not particularly limited, the nucleotide can be preferably in a part other than the internal loop 1 section and loop 2 section in the aforementioned potential secondary structure, so that the activity of the aptamer of the present invention can be maintained.

While the nucleotide length of the aptamer or nucleic acid of the present invention is not particularly limited, it is generally 34—about 200 nucleotides, preferably 34—about 100 nucleotides, more preferably 36-60 nucleotides, further preferably 38-44 nucleotides. The base length of the aptamer or nucleic acid of the present invention is preferably not more than 50, more preferably not more than 44. The chemical syntheses and mass-production of the aptamer become easier by reducing the total number of nucleotides to fall within the range permitting formation of the potential secondary structure represented by above-mentioned formula (I), and there is a major advantage in terms of cost. Such aptamer is also considered to permit easy chemical modification, high stability in the body, and low toxicity.

The aptamer of the present invention can also be a conjugate selected from the group consisting of a conjugate of a plurality of nucleic acids consisting of the nucleotide sequence of the above-mentioned (a), a conjugate of a plurality of nucleic acids consisting of the nucleotide sequence of the above-mentioned (b), and a conjugate of a plurality of nucleic acids consisting of the nucleotide sequence of the above-mentioned (a) and nucleic acids consisting of the nucleotide sequence of the above-mentioned (b).

These conjugates can also bind to NGF and/or inhibit the activity of NGF (NGF receptor binding activity etc.).

Conjugation herein can be achieved by tandem binding. In the conjugation, a linker may be utilized. As the linker, nucleotide chains (e.g., 1 to about 20 nucleotides) and non-nucleotide chains (e.g., —(CH$_2$)$_n$— linker, —(CH$_2$CH$_2$O)$_n$— linker, hexaethylene glycol linker, TEG linker, peptide-containing linker, —S—S— bond-containing linker, —CONH— bond-containing linker, —OPO$_3$— bond-containing linker) can be mentioned. The plurality as mentioned in the above-described conjugate of a plurality thereof is not particularly limited, as long as it is two or more, and the plurality can be, for example, 2, 3 or 4.

Each nucleotide contained in the aptamer of the present invention is the same or different and can be a nucleotide comprising a hydroxyl group at the 2'-position of ribose (e.g., ribose of pyrimidine nucleotide, ribose of purine nucleotide) (i.e., unsubstituted nucleotide) or a nucleotide wherein a hydroxyl group is replaced by any atom or group at the 2'-position of ribose. As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH₂ group) can be mentioned. In the following cases, the hydroxyl group is replaced by a hydrogen atom, a fluorine atom or —O-Me group, respectively, at the 2'-position of ribose.

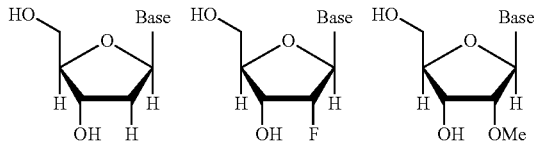

The aptamer of the present invention can also be the nucleotide wherein at least one kind (e.g., 1, 2, 3 or 4 kinds) of nucleotide comprises a hydroxyl group, or the above-described any atom or group, for example, at least two kinds (e.g., 2, 3 or 4 kinds) of groups selected from the group consisting of a hydrogen atom, a fluorine atom, a hydroxyl group and a —O-Me group, at the 2'-position of ribose.

Also, in the aptamer of the present invention, all pyrimidine nucleotides are the same or different and each can be a nucleotide substituted by a fluorine atom, or a nucleotide substituted by any atom or group mentioned above, preferably an atom or group selected from the group consisting of a hydrogen atom, a hydroxyl group and a methoxy group at the 2'-position of ribose.

In the aptamers of the present invention, moreover, all purine nucleotides are the same or different and each can be a nucleotide substituted by a hydroxyl group, or a nucleotide substituted by any atom or group mentioned above, preferably an atom or a group selected from the group consisting of a hydrogen atom, a methoxy group, and a fluorine atom at the 2'-position of ribose.

In the aptamers of the present invention, moreover, all nucleotides can comprise a hydroxyl group, or any atom or group mentioned above, for example, the identical group selected by the group consisting of a hydrogen atom, a fluorine atom, a hydroxyl group and a —O-Me group at the 2'-position of ribose.

In this Description, the nucleotides constituting the aptamer are assumed to be RNAs (i.e., the sugar groups are assumed to be ribose) in describing how the sugar groups are modified in the nucleotides. However, this does not mean that DNA is exempted from the aptamer-constituting nucleotides, and a modification of RNA should read as a modification of DNA as appropriate. When the nucleotide constituting the aptamer is DNA, for example, replacement of the hydroxyl group at the 2'-position of ribose by X should read as a replacement of one hydrogen atom at the 2'-position of deoxyribose by X.

When uracil is substituted with thymine in the aptamer of the present invention, NGF-binding activity, NGF-NGF receptor binding inhibitory activity, NGF neurite outgrowth inhibitory activity, NGF cell proliferation inhibitory activity, stability, drug deliverability and stability in blood of the aptamer and the like can be increased.

The aptamer of the present invention binds to NGF, which is a known neurotrophin, and is an important secretory protein involved in the development and survival of peripheral and central neurons. In the present invention, NGF particularly means a β type NGF. The amino acid sequences of human β-NGF are those shown by Accession Numbers NP002497, P01138, AAI26151, AAI26149 and CAB75625, which may also be one with mutation, its functional domain or peptide fragment. It may be not only a monomer but also a dimer or multimer. Furthermore, it includes NGF derived from non-human mammals, for example, primates (e.g., monkey), rodents (e.g., mouse, rat, guinea pig), and companion animals, domestic animals and working animals (e.g., dog, cat, horse, bovine, goat, sheep, swine).

The aptamer of the present invention inhibits the activity of NGF by binding to NGF and inhibiting the binding of NGF and NGF receptor. The aptamer of the present invention may bind to any part of NGF as long as the binding of NGF and NGF receptor can be inhibited.

In the present Description, the "inhibitory activity against NGF" means an inhibitory ability on any activity NGF has. For example, it means an activity to inhibit NGF from binding to NGF receptor, inhibition of signal transduction in the downstream of NGF receptor (Ras-MAP kinase pathway, PI3 kinase pathway), inhibition of increased expression of TRPV1, SP, BDNF and the like, inhibitory activity of expression of HA, BK, PG, NGF and other cytokine released from mast cells and the like, which result from the binding of NGF to NGF receptor, further, inhibition of differentiation, survival, neurite outgrowth of nerve cell induced by NGF, increase of blood vessel permeability, enhancement of immune response of T cells and B cells, differentiation of lymphocytes, growth and the like of various cells such as mast cells, erythroleukemic cells, cancer cells and the like, relief of pain, hyperalgesia and the like, induced by NGF, can be mentioned.

Preferable "inhibitory activity against NGF" that the aptamer of the present invention has is an activity to inhibit the binding of NGF to NGF receptor, an activity to inhibit neurite outgrowth activity induced by NGF, an activity to inhibit the cell proliferation activity induced by NGF and the like.

The aptamer of the present invention binds to NGF in a physiological buffer (e.g., solution A: see Example 1). The aptamer of the present invention binds to, for example, NGF at an intensity detectable by the following test.

For the measurement, BIAcore2000 manufactured by BIAcore is used. An aptamer is immobilized on a sensorchip. The amount to be immobilized is set to 1000 RU. A physiological buffer containing 0.3M NaCl (solution A: see Example 1) is used to prepare NGF solution (0.5 µM). This NGF solution (20 µL) is injected and the binding of NGF to the aptamer is detected. Using RNA containing a random nucleotide consisting of 40 nucleotides as a negative control, when NGF significantly strongly binds to the aptamer as compared to the control RNA, the aptamer is evaluated to have bindability to NGF.

In the present Description, the "NGF receptor" means a cell surface protein to which NGF binds. As the NGF receptor, TrkA and p75 are known. The NGF receptor referred to in the present invention may be a protein containing a natural amino acid sequence or a variant thereof. Here, the "variant thereof" means a protein or peptide wherein several amino acids of an amino acid sequence of "NGF receptor" have been substituted, or a partial amino acid sequence thereof, which has a binding activity to NGF and inhibits the binding of NGF and an NGF receptor.

The aptamer of the present invention binds to NGF and inhibits the binding of NGF and an NGF receptor. Whether or not the aptamer inhibits the binding of NGF to an NGF receptor, for example, can be evaluated by the following test.

For the measurement, BIAcore2000 manufactured by BIAcore is used. On a CM5 sensorchip is immobilized a fusion protein of NGF receptor and Fc (e.g., TrkA-Fc (175-TK, R&D systems) or p75-Fc (R&D systems)). The amount to be immobilized is 500 to 700 RU. NGF (0.1 µM) and an aptamer (0.2 µM) are mixed in a physiological buffer (solution A: see Example 1), and a mixture to be a sample is prepared over 30 min. This mixture is injected into BIAcore2000, and the binding of NGF to an NGF receptor is detected.

In one embodiment, the aptamer of the present invention can inhibit both the binding of NGF and TrkA, and that of NGF and p75.

The aptamer of the present invention is an aptamer that inhibits neurite outgrowth activity of NGF and/or cell proliferation activity of NGF. Whether the aptamer of the present invention can inhibit neurite outgrowth activity of NGF can be evaluated by, for example, the test described in Example 3. In addition, whether the aptamer of the present invention can inhibit cell proliferation activity of NGF can be evaluated by, for example, the test described in Example B.

The aptamer of the present invention is characterized by the concentration necessary for inhibiting the neurite outgrowth activity of NGF by 50% ($IC_{50}$ or 50% inhibitory concentration), which is not more than 1 nM. Since conventionally-known NGF aptamers have an $IC_{50}$ value of about several nM for the neurite outgrowth activity of NGF, the aptamer of the present invention shows more superior property as regards the neurite outgrowth inhibitory activity.

In a preferable embodiment, the aptamer of the present invention also shows an $IC_{50}$ value of not more than 1 nM for the cell proliferation activity of NGF.

On the other hand, whether the aptamer of the present invention has an activity to inhibit the cell proliferation activity of neurotrophin other than NGF, specifically, brain-derived neurotrophic factor (BDNF), neurotrophin-3 (NT-3) and neurotrophin 4/5 (NT-4/5) varies depending on the aptamer. Here, the terms BDNF, NT-3 and NT-4/5 respectively mean BDNF, NT-3 and NT-4/5 of all mammals species including human.

The level of the inhibitory activity against cell proliferation of other neurotrophins (BDNF, NT-3, NT-4/5) can be evaluated by the test described in Example 16. The cell proliferation inhibitory activity of the aptamer of the present invention as described in Example 16 and Table 2 is shown by an $IC_{50}$ value of not more than 0.1 nM for NGF, and not less than 1000 nM for BDNF, which means that the aptamer of the present invention does not inhibit the cell proliferation activity of BDNF. However, it is 0.97 nM to not less than 10 nM for NT-3; and not more than 3 nM to not less than 30 nM for NT-4. Therefore, inhibition of the cell proliferation activity of NT-3 and NT-4 varies depending on the aptamers.

The aptamer of the present invention may be one wherein a sugar residue (e.g., ribose) of each nucleotide has been modified to increase the NGF-binding activity, NGF-NGF receptor binding inhibitory activity, NGF neurite outgrowth inhibitory activity, NGF cell proliferation inhibitory activity, stability, drug deliverability, and stability in blood of the aptamer and the like. Examples of the modification in a sugar residue include replacement of oxygen atom at the 2'-position, 3'-position and/or 4'-position of the sugar residue with another atom, and the like. As the kind of the modification, fluorination, O-alkylation (e.g., O-methylation, O-ethylation), O-arylation, S-alkylation (e.g., S-methylation, S-ethylation), S-arylation, and amination (e.g., —$NH_2$) can be mentioned. In addition, examples thereof include 4'-SRNA wherein the 4'-position oxygen is replaced with sulfur, LNA (Locked Nucleic Acid) wherein the 2'-position and the 4'-position are crosslinked via methylene, 3'-N-phosphoramidate nucleic acid wherein the 3'-position hydroxyl group is replaced with an amino group and the like. Such alterations in the sugar residue can be performed by a method known per se (see, for example, Sproat et al., (1991) Nucl. Acid. Res. 19, 733-738; Cotton et al., (1991) Nucl. Acid. Res. 19, 2629-2635; Hobbs et al., (1973) Biochemistry 12, 5138-5145).

The aptamer of the present invention may also have a nucleic acid base (e.g., purine or pyrimidine) altered (e.g., chemical substitution) to increase the NGF-binding activity, NGF-NGF receptor binding inhibitory activity, NGF neurite outgrowth inhibitory activity, NGF cell proliferation inhibitory activity, stability, drug deliverability, and stability in blood of the aptamer and the like. As examples of such alterations, pyrimidine alteration at 5-position, purine alteration at 6- and/or 8-position(s) (O-methyl modification and the like), alteration with an extracyclic amine, substitution with 4-thiouridine, substitution with 5-bromo or 5-iodo-uracil, modification of 5-amino acid type and modification of 5-tryptophan side chain can be mentioned. The phosphate group contained in the aptamer of the present invention may be altered to confer resistance to nuclease and hydrolysis. For example, the phosphate region of the aptamer may be replaced with P(O)S (thioate), P(S)S (dithioate), P(O)$NR_2$ (amidate), P(O)R, P(O)OR', CO or $CH_2$ (formacetal), P(O)$BH_3$ (boranophosphate) or 3'-amine (—NH—$CH_2$—$CH_2$—) [wherein each unit of R or R' is independently H or a substituted or unsubstituted alkyl (e.g., methyl, ethyl)].

The linking group is, for example, —O—, —N— or —S—, and nucleotides can bind to an adjoining nucleotide via these linking groups.

The alterations may also include alterations such as capping at 3' and 5'.

An alteration can further be performed by adding to an end a polyethyleneglycol (hereinafter, sometimes to be described as "PEG"), amino acid, peptide, inverted dT, myristoyl, lithocolic-oleyl, docosanyl, lauroyl, stearoyl, palmitoyl, oleoyl, linoleoyl, other lipids, steroids, cholesterol, caffeine, vitamins, pigments, fluorescent substances, anticancer agent, toxin, enzymes, radioactive substance, biotin and the like. For such alterations, see, for example, U.S. Pat. Nos. 5,660,985 and 5,756,703.

Particularly, when alteration is performed by terminal addition of PEG, the molecular weight of PEG is not particularly limited, and is preferably 1000-100000, more preferably 30000-90000. PEG may be linear or branched into two or more chains (multi-arm PEG).

Such PEG is not particularly limited, and those of ordinary skill in the art can appropriately select and use commercially available or known PEG (e.g., http://www.peg-drug.com/peg_product/branched.html). Specific preferable examples of the PEG to be applied to the aptamer of the present invention include 2-branched GS type PEG having a molecular weight of 40000 (SUNBRIGHT GL2-400GS2 manufactured by NOF CORPORATION), 2-branched TS type PEG having a molecular weight of 40000 (SUNBRIGHT GL2-400TS manufactured by NOF CORPORATION), 4-branched TS type PEG having a molecular weight of 40000 (SUNBRIGHT GL4-400TS manufactured by NOF CORPORATION), 2-branched TS type PEG having a molecular weight of 80000 (SUNBRIGHT GL2-800TS manufactured by NOF CORPORATION), 4-branched TS type PEG having a molecular weight of 80000 (SUNBRIGHT GL4-800TS manufactured by NOF CORPORATION) and the like.

In this case, in the aptamer of the present invention, PEG may be directly added to the terminus. It is more preferable that a linker having a group bindable to PEG and the like be added to the terminus thereof, and PEG be added to the aptamer of the present invention via the linker.

The linker for PEG and the aptamer of the present invention is not particularly limited, and carbon chain number, functional group and the like can be appropriately selected according to the binding site, the kind of PEG and the like. Examples of such linker include a linker having an amino group. Specifically, when added to the 5' end, ssH Linker (SAFC) or DMS (O)MT-AMINO-MODIFIER (GLEN RESEARCH) can be mentioned, and when added to the 3' end, TFA Amino C-6 lcaa CPG (ChemGenes) and the like can be mentioned. When this linker is selected, for example, an active group of N-hydroxysuccinimide is added to PEG, and reacted with an amino group on the linker side, whereby the aptamer of the present invention can be bound to PEG via the linker.

As PEG and linker, commercially available products can be preferably used. The reaction conditions and the like relating to the binding of PEG, a linker and the aptamer of the present invention can be appropriately determined by those of ordinary skill in the art.

The aptamer of the present invention can be chemically synthesized as disclosed herein and by a method known per se in the art. An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to the positive charge of lysine and arginine present on the surface of protein. For this reason, nucleic acid bases not involved in the direct binding to the target substance can be substituted. In particular, because the section of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

An aptamer can be prepared by utilizing the SELEX method or an improved version thereof (e.g., Ellington et al., (1990) Nature, 346, 818-822; Tuerk et al., (1990) Science, 249, 505-510). In the SELEX method, by increasing the number of rounds or using a competing substance, an aptamer exhibiting a stronger binding potential for the target molecule is concentrated and selected. Hence, by adjusting the number of rounds of SELEX and/or changing the competitive condition, aptamers with different binding forces, aptamers with different binding modes, and aptamers with the same binding force or binding mode but different base sequences can be obtained in some cases. The SELEX method comprises a process of amplification by PCR; by causing a mutation by using manganese ions and the like in the process, it is possible to perform SELEX with higher diversity.

The aptamers obtained by SELEX are nucleic acids that exhibit high affinity for the target substance, but this does not mean binding to an active site of the target substance. Therefore, the aptamers obtained by SELEX do not necessarily act on the function of the target substance. NGF is a basic protein, and is thought to be likely to allow nucleic acids to bind thereto nonspecifically. An aptamer that does not bind to an active site does not influence the activity of the target substance.

Based on an active aptamer thus selected, SELEX can be performed based on the sequence of the obtained aptamer to acquire an aptamer possessing higher activity. Specifically, after preparing a template wherein an aptamer with a determined sequence is partially randomized or a template doped with about 10 to 30% of random sequences, SELEX is performed again.

An aptamer obtained by SELEX has a length of about 80 nucleotides, and this is difficult to prepare as a medicament as it is. Hence, it is necessary to repeat try-and-error efforts to shorten the aptamer to a length of about 60 nucleotides or less enabling easy chemical synthesis, more preferably about 50 nucleotides or less, most preferably 45 nucleotides or less. Depending on the primer design for an aptamer obtained by SELEX, the ease of the subsequent minimization operation changes. Unless the primer is designed successfully, subsequent development will be impossible even if an aptamer with activity is selected by SELEX.

Aptamers are altered easily since they permit chemical synthesis. For aptamers, by predicting the secondary structure using the MFOLD program, or by predicting the steric structure by X-ray analysis or NMR analysis, it is possible to predict to some extent which nucleotide can be substituted or deleted, and where to insert a new nucleotide. A predicted aptamer with the new sequence can easily be chemically synthesized, and it can be determined whether or not the aptamer retains the activity using an existing assay system.

If a region important to the binding of the obtained aptamer with the target substance is identified by repeated try-and-error efforts as described above, the activity remains unchanged in many cases even when a new sequence is added to both ends of the sequence. Such length of the new sequence is not particularly limited.

Modifications, like sequences, afford a wide range of design or alterations.

As stated above, aptamers permit a wide range of design or alterations. The present invention also provides a production method of aptamer that enables a wide range of design or alteration of an aptamer comprising a specified sequence (e.g., a sequence corresponding to a portion selected from among stem section, internal loop section, hairpin loop section and single-strand section: hereinafter, abbreviated as fixed sequence as required).

For example, the production method of such aptamer includes production of an aptamer comprising a fixed sequence by using a single kind of nucleic acid molecule consisting of a nucleotide sequence shown by:

| Primer sequence (i) | -(N) a-fixed sequence-(N) b- | Primer sequence (ii) |

[wherein (N)a represents a nucleotide chain consisting of "a" units of N; (N)b represents a nucleotide chain consisting of "b" units of N; each of the units of N, whether identical or different, is a nucleotide selected from the group consisting of A, G, C, U and T (preferably, A, G, C and U). Each of "a" and "b", whether identical or different, can be any numbers, and can be, for example, 1 to about 100, preferably 1 to about 50, more preferably 1 to about 30, still more preferably 1 to about 20 or 1 to about 10], or plural kinds of nucleic acid molecules (e.g., library of nucleic acid molecule different in the number of a, b etc.) and primer pairs corresponding to the primer sequences (i) and (ii), respectively.

The aptamer of the present invention is preferably an aptamer that binds to NGF, characteristically contains the sequence shown by SEQ ID NO: 82, and has a nucleotide length of not more than 50.

The sequence shown by SEQ ID NO: 82 is a region important for the aptamer of the present invention to function as the aptamer of the present invention such as binding to NGF and inhibiting the activity of NGF, particularly neurite outgrowth activity, cell proliferation activity and the like. Even when a new sequence is added to both ends of the sequence, the function of the aptamer of the present invention is not impaired. The sequence may be subject to modification of the aforementioned sugar residue, alteration of nucleic acid base and phosphate group, and the like.

Thus, preferable specific examples of the aptamer of the present invention include
aptamers comprising the sequence shown by SEQ ID NO: 82, having a nucleotide length of not more than 50, and binding to NGF, which are
(i) an aptamer comprising at least one kind of nucleotide wherein the hydroxyl group is replaced by a hydrogen atom, a fluorine atom, a —O-alkyl group, a —O-acyl group or an amino group at the 2'-position of ribose;
(ii) an aptamer wherein PEG, amino acid, peptide, inverted dT, myristoyl, lithocolic-oleyl, docosanyl, lauroyl, stearoyl, palmitoyl, oleoyl, linoleoyl, other lipid, steroid, cholesterol, caffeine, vitamin, dye, a fluorescent substance, an anti-cancer agent, a toxin, an enzyme, a radioactive substance or biotin is added to the terminus;
(iii) an aptamer that satisfies the requirements of (i) and (ii); and the like.

The present invention also provides a complex comprising the aptamer of the present invention and a functional substance bound thereto. The bond between the aptamer and the functional substance in the complex of the present invention can be a covalent bond or a non-covalent bond. The complex of the present invention can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. As examples of the functional substance, proteins, peptides, amino acids, lipids, sugars, monosaccharides, polynucleotides, and nucleotides can be mentioned. As examples of the functional substance, affinity substances (e.g., biotin, streptavidin, polynucleotides possessing affinity for target complementary sequence, antibodies, glutathione Sepharose, histidine), substances for labeling (e.g., fluorescent substances, luminescent substances, radioisotopes), enzymes (e.g., horseradish peroxidase, alkaline phosphatase), drug delivery vehicles (e.g., liposome, microspheres, peptides, polyethyleneglycols), drugs (e.g., those used in missile therapy such as calicheamycin and duocarmycin; nitrogen mustard analogues such as cyclophosphamide, melphalan, ifosfamide or trofosfamide; ethylenimines such as thiotepa; nitrosoureas such as carmustine; alkylating agents such as temozolomide or dacarbazine; folate-like metabolic antagonists such as methotrexate or raltitrexed; purine analogues such as thioguanine, cladribine or fludarabine; pyrimidine analogues such as fluorouracil, tegafur or gemcitabine; vinca alkaloids such as vinblastine, vincristine or vinorelbine and analogues thereof; podophyllotoxin derivatives such as etoposide, taxans, docetaxel or paclitaxel; anthracyclines such as doxorubicin, epirubicin, idarubicin and mitoxantrone, and analogues thereof; other cytotoxic antibiotics such as bleomycin and mitomycin; platinum compounds such as cisplatin, carboplatin and oxaliplatin; pentostatin, miltefosine, estramustine, topotecan, irinotecan and bicalutamide), and toxins (e.g., ricin toxin, liatoxin and Vero toxin) can be mentioned. These functional molecules are finally removed in some cases. Furthermore, the molecules may be peptides that can be recognized and cleaved by enzymes such as thrombin, matrix metalloproteinase (MMP), and Factor X, and may be polynucleotides that can be cleaved by nucleases or restriction endonuclease.

The aptamer or the complex of the present invention can be used as, for example, a medicament or a diagnostic agent, a test drug, a reagent, an additive for drinking water and food, an enhancer and a mitigator.

The aptamer and complex of the present invention can have an activity to inhibit the function of NGF by binding to NGF and inhibiting the binding of NGF and an NGF receptor. As mentioned above, NGF is deeply involved in the pain and inflammation. Therefore, the aptamer and complex of the present invention are useful as medicaments for the prophylaxis or treatment of diseases accompanying pain or inflammation (anti-pain agent, anti-inflammatory agent etc.).

Here, examples of the pain include nociceptive pain (muscular pain, back pain, upper limb pain, whiplash injury, arthralgia, osteoarthritis, gout, rheumatoid arthritis, headache, migraine headache, catatonic headache, cluster headache, secondary headache, orofacial pain, toothache, causalgia after tooth extraction, phantom tooth pain, organ pain, cardiac pain, abdominal pain, mittelschmerz, dysmenorrhea, labor pain, nephralgia, ureteralgia, ostalgia and the like), inflammatory pain, neuropathic pain (diabetic neuropathy, toxic neuropathy, postoperative pain, phantom limb pain, stump pain, reflex sympathetic dystrophy, causalgia, postherpetic pain, trigeminal neuralgia, central pain), carcinomatous pain (pain due to cancer infiltration into visceral organ, pain caused by blood vessel obstruction due to blood vessel infiltration of cancer tissue, pain of bone metastasis, pain associated with intracerebral metastasis, pain caused by peripheral nerve infiltration of cancer tissue), fibromyalgia pain and the like.

While the disease associated with inflammation here is not particularly limited, systemic lupus erythematosus, multiple sclerosis, psoriasis, osteoarthritis, rheumatoid arthritis, interstitial cystitis, asthma and the like can be mentioned.

While the above-mentioned cancer is not particularly limited, esophagus cancer, thyroid cancer, urinary bladder cancer, colorectal cancer, gastric cancer, pancreatic cancer, thoracic cancer, liver cancer, lung cancer, non-small cell lung cancer, breast cancer, neuroblastoma, glioblastoma, uterine cancer, cervical cancer, ovarian cancer, Wilms' tumor, prostate cancer and the like can be mentioned.

When NGF binds to a receptor thereof, TrkA, it activates tyrosine phosphorylation of TrkA and Ras-MAPK, PLC-γ, PI3K and the like at the downstream of TrkA, and exhibits physiological actions such as survival and differentiation of nerve cells. On the other hand, it induces cell death in the signal pathway via p75 receptor. Therefore, the aptamer and complex of the present invention can be used as medicaments, diagnostic agents, test drugs, or reagents for diseases relating to activation of these signal transduction pathways. Examples of the diseases relating to the activation of these signal transduction pathways include the above-mentioned algia, inflammatory disease and cancers.

When the aptamer and complex of the present invention are used as medicaments, diagnostic agents, test drugs, reagents and the like, the subject of administration thereof is not particularly limited and, for example, primates (e.g., human, monkey), rodents (e.g., mouse, rat, guinea pig), and companion animals, domestic animals and working animals (e.g., dog, cat, horse, bovine, goat, sheep, swine) can be mentioned.

The aptamer and complex of the present invention are capable of binding specifically to NGF. Therefore, the aptamer and complex of the present invention are useful as probes for NGF detection. The probes are useful in in vivo imaging of NGF, measurements of blood concentrations, tissue staining, ELISA and the like. The probes are also useful as diagnostic agents, test drugs, reagents and the like for diseases involving NGF (diseases accompanied by pain or inflammation, and the like).

Based on their specific binding to NGF, the aptamer and complex of the present invention can be used as ligands for separation and purification of NGF.

In addition, the aptamer and complex of the present invention can be used as test drugs for examining the mental condition of romance and the like, or medicaments, regulators, enhancers or mitigators for controlling the mental condition.

The aptamer and complex of the present invention can be used as drug delivery vehicles.

The medicament of the present invention can be one formulated with a pharmaceutically acceptable carrier. As examples of the pharmaceutically acceptable carrier, excipients such as sucrose, starch, mannit, sorbit, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizinammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not limitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The medicament of the present invention can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide and the like) and the like are used. The medicament may be a rapid-release preparation or sustained-release preparation. Examples of sustained-release bases include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. Sustained-release preparations are also suitable preparations. The sustained-release preparations include sustained release from carriers or containers embedded in the body, such as artificial bones, biodegradable or non-degradable sponges, bags, drug pumps, osmotic pressure pumps and the like. Devices for continuous or intermittent, systemic or topical delivery from outside the body are also included in the scope of sustained-release preparations. Biodegradable bases include liposome, cationic liposome, poly(lactic-co-glycolic) acid (PLGA), atherocollagen, gelatin, hydroxyapatite, polysaccharide sizofiran. In addition to liquid injections and sustained release preparation, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

Here, as examples of the surfactant, oleic acid, lecithin, diethylene glycol dioleate, tetrahydrofurfuryl oleate, ethyl oleate, isopropyl myristate, glyceryl trioleate, glyceryl monolaurate, glyceryl monooleate, glyceryl monostearate, glyceryl monolysinoate, cetyl alcohol, stearyl alcohol, polyethyleneglycol 400, cetylpyridinium chloride, sorbitan trioleate (trade name, Span 85), sorbitan monoleate (trade name, Span 80), sorbitan monolaurate (trade name, Span 20), polyoxyethylene hardened castor oil (trade name, HCO-60), polyoxyethylene (20) sorbitan monolaurate (trade name, Tween 20), polyoxyethylene (20) sorbitan monooleate (trade name, Tween 80), lecithin of natural resource origin (trade name, EPICLON), oleylpolyoxyethylene (2) ether (trade name, Brij 92), stearyl polyoxyethylene (2) ether (trade name, Brij 72), lauryl polyoxyethylene (4) ether (trade name, Brij 30), oleylpolyoxyethylene (2) ether (trade name, Genapol 0-020), block copolymer of oxyethylene and oxypropylene (trade name, Synperonic) and the like can be mentioned. As examples of the oil, corn oil, olive oil, cottonseed oil, sunflower oil and the like can be mentioned. In the case of an ointment, an appropriate pharmaceutically acceptable base (yellow petrolatum, white petrolatum, paraffin, plastibase, silicone, white ointment, beeswax, lard, vegetable oils, hydrophilic ointment, hydrophilic petrolatum, purified lanolin, hydrolyzed lanolin, water-absorbing ointment, hydrophilic plastibase, macrogol ointment and the like) is blended with an active ingredient, and used as a preparation.

An inhalant can be produced according to a conventional method. Specifically, an inhalant can be produced by powdering or liquefying the above-described aptamer and complex of the present invention, blending it in an inhalation propellant and/or carrier, and filling them in an appropriate inhalation vessel. When the above-described aptamer and complex of the present invention is a powder, an ordinary mechanical powder inhalator can be used; in the case of a liquid, an inhalator such as a nebulizer can be used. Here, as the propellant, conventionally known one can be widely used; chlorofluorocarbon-series compounds such as chlorofluorocarbon-11, chlorofluorocarbon-12, chlorofluorocarbon-21, chlorofluorocarbon-22, chlorofluorocarbon-113, chlorofluorocarbon-114, chlorofluorocarbon-123, chlorofluorocarbon-142c, chlorofluorocarbon-134a, chlorofluorocarbon-227, chlorofluorocarbon-C318, and 1,1,1,2-tetrafluoroethane, hydrocarbons such as propane, isobutane, and n-butane, ethers such as diethyl ether, compressed gases such as nitrogen gas and carbon dioxide gas and the like can be mentioned.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The present invention also provides a solid phase carrier having the aptamer and the complex of the present invention immobilized thereon. As examples of the solid phase carrier, a substrate, a resin, a plate (e.g., multiwell plate), a filter, a cartridge, a column, and a porous material can be mentioned. The substrate can be one used in DNA chips, protein chips and the like; for example, nickel-PTFE (polytetrafluoroethylene) substrates, glass substrates, apatite substrates, silicone substrates, alumina substrates and the like, and substrates prepared by coating these substrates with a polymer and the like can be mentioned. As examples of the resin, agarose particles, silica particles, a copolymer of acrylamide and N,N'-methylenebisacrylamide, polystyrene-crosslinked divinylbenzene particles, particles of dextran crosslinked with epichlorohydrin, cellulose fiber, crosslinked polymers of aryldextran and N,N'-methylenebisacrylamide, monodispersed synthetic polymers, monodispersed hydrophilic polymers, Sepharose, Toyopearl and the like can be mentioned, and also resins prepared by binding various functional groups to these resins were included. The solid phase carrier of the present invention can be useful in, for example, purifying, detecting and quantifying NGF.

The aptamer and the complex of the present invention can be immobilized onto a solid phase carrier by a method known per se. For example, a method that introduces an affinity substance (e.g., those described above) or a predetermined functional group into the aptamer or the complex of the present invention, and then immobilizes the aptamer and complex onto a solid phase carrier via the affinity substance or predetermined functional group can be mentioned. The present invention also provides such methods. The predetermined functional group can be a functional group that can be subjected to a coupling reaction; for example, an amino group, a thiol group, a hydroxyl group, and a carboxyl group can be mentioned. The present invention also provides an aptamer having such a functional group introduced thereto.

The present invention also provides a method of purifying and concentrating NGF. In particular, the present invention makes it possible to separate NGF from the proteins of other family proteins. The method of purification and concentration of the present invention can comprise adsorbing NGF to the solid phase carrier of the present invention, and eluting the adsorbed NGF with an eluent. Adsorption of NGF to the solid phase carrier of the present invention can be achieved by a method known per se. For example, a NGF-containing sample (e.g., bacterial or cell culture or culture supernatant, blood) is introduced into the solid phase carrier of the present invention or a composition containing the same. NGF can be eluted using an eluent such as a neutral solution. There is no limitation on the neutral eluent, which can have a pH of, for example, about 6 to about 9, preferably about 6.5 to about 8.5, and more preferably about 7 to about 8. The neutral solution can also comprise, for example, urea, a chelating agent (e.g., EDTA), a potassium salt (e.g., KCl), a magnesium salt (e.g., $MgCl_2$), a surfactant (e.g., Tween 20, Triton, NP40), and glycerin. The method of purification and concentration of the present invention can further comprise washing the solid phase carrier using a washing solution after NGF adsorption. Examples of the washing solution include those containing urea, a chelating agent (e.g., EDTA), Tris, an acid, an alkali, Transfer RNA, DNA, surfactants such as Tween 20, salts such as NaCl and the like. The method of purification and concentration of the present invention can still further comprise heating the solid phase carrier. This step enables the regeneration and sterilization of the solid phase carrier.

The present invention also provides a method of detecting and quantifying NGF. In particular, the present invention makes it possible to detect and quantify NGF separately from the proteins of other family proteins. The method of detection and quantitation of the present invention can comprise measuring NGF by utilizing the aptamer of the present invention (e.g., by the use of the complex and solid phase carrier of the present invention). The method of detecting and quantifying NGF can be performed in the same manner as an immunological method, except that the aptamer of the present invention is used in place of an antibody. Therefore, by using the aptamer of the present invention as a probe in place of an antibody, in the same manner as such methods as enzymeimmunoassay (EIA) (e.g., direct competitive ELISA, indirect competitive ELISA, sandwich ELISA), radioimmunoassay (RIA), fluorescent immunoassay (FIA), Western blot technique, immunohistochemical staining method, and cell sorting method, detection and quantitation can be performed. The aptamer of the present invention can also be used as a molecular probe for PET and the like. These methods can be useful in, for example, measuring NGF contents in living organisms or biological samples, and in diagnosing a disease associated with NGF.

The disclosures in all publications mentioned herein, including patents and patent application specifications, are incorporated by reference herein in the present invention to the extent that all of them have been given expressly.

The present invention is hereinafter described in more detail by means of the following Examples, which, however, never limit the scope of the invention.

EXAMPLES

Example 1

Production of NGF Aptamer—1

RNA aptamers that bind specifically to NGF were prepared using the SELEX method. The SELEX was performed by referring the method of Ellington et al. (Ellington and Szostak, Nature 346, 818-822, 1990) and the method of Tuerk et al. (Tuerk and Gold, Science 249, 505-510, 1990). Human NGF (manufactured by R&D Systems) was used as a target substance.

The RNA used in the first round (40N) was obtained by transcribing a chemically synthesized DNA using the DuraScribe™ T7 Transcription Kit (manufactured by Epicentre). Of the NTPs contained in the kit, 2'-OH ATP was replaced by 2'-deoxyadenosine 5'-triphosphate (2'-H ATP or dATP, manufactured by GE Healthcare) and other substrates contained in the kit were used. The RNA obtained by this method has a fluorinated 2'-position of the ribose of the pyrimidine nucleotide, and G (purine nucleotide) is of RNA type, and A is of DNA type. The DNA of 83 nucleotides shown below, having a primer sequence at each end of a 40-nucleotide random sequence was used as DNA template. The DNA template and the primers were prepared by chemical synthesis.

```
DNA template 1:
                                        (SEQ ID NO: 118)
5'-gaggatccatgtatgcgcacata-40n-cttctggtcgaagttctcc
c-3' primer Fwd1:
                                        (SEQ ID NO: 119)
5'-cggaattctaatacgactcactatagggagaacttcgaccagaag-
3' primer Rev1:
                                        (SEQ ID NO: 120)
5'-gaggatccatgtatgcgcacata-3'
```

In the above-mentioned sequence, n represents any one of a, g, c and t. The primer Fwd1 comprises a promoter sequence of T7 RNA polymerase. The variation of the RNA pool used in the first round was theoretically $10^{14}$.

After 10 rounds of SELEX, the PCR product was cloned into a pGEM-T Easy vector (manufactured by Promega), which was used to transform *Escherichia coli* strain DH5α (manufactured by Toyobo). The plasmid was extracted from a single colony and the base sequences were determined by DNA sequencer (ABI PRISM3100, manufactured by ABI). 48 clones were examined, and 45 sequences could be sequenced. Among them were 7 kinds of the same 2 sequences, and the remaining 31 sequences were single sequences. 3 rounds of SELEX were further added, and the sequence was examined. As a result, further convergence was observed.

The sequences showing convergence in 10 and 13 rounds and several single sequences were evaluated for the binding activity to NGF by a surface plasmon resonance method. As the measuring apparatus, BIAcore2000 manufactured by BIAcore was used and, as the sensor chip, CM5 that reacts with an amino group was used. Human NGF was dissolved in immobilization solution (10 mM sodium acetate, pH 6) at 25-40 μg/ml. For the reaction of an amino group on the protein side and a carboxyl group on the chip side, ethyl-3-carbodiimide hydrochloride and N-hydroxysuccinimide were used. After the reaction, blocking by ethanolamine-HCl was performed. The immobilized amount of NGF was set to 3,000-4,000 RU. An aptamer for analyte was prepared to 0.15 μM-0.5 μM. As a running buffer, solution A was used. Here, solution A is a mixed solution of 145 mM sodium chloride, 5.4 mM potassium chloride, 1.8 mM calcium chloride, 0.8 mM magnesium chloride, 20 mM Tris (pH 7.6), 0.05% Tween 20. As a regeneration solution, a mixed solution of 1M NaCl and 50 mM NaOH was used. NGF was immobilized on FC2, and the results of FC1 were subtracted to give a final sensorgram.

The binding activity of 34 sequences was measured to find that all RNAs more significantly bind to NGF than 40N of the control. Here, 40N refers to the RNA pool used for the first round, comprising a 40-nucleotide random sequence. From the above, it was shown that these RNAs are aptamers that bind to NGF.

Example 2

Aptamer Inhibiting Binding of NGF and NGF Receptor

Whether the aptamers obtained in Example 1 inhibit the binding of NGF and an NGF receptor (TrkA and p75) was determined using the surface plasmon resonance method.

As directed in BIAcore's protocol, Protein A (21181, PIERCE) was immobilized on a CM5 sensor chip. About 700 to 1200 RU of human TrkA fused with the Fc portion of IgG (175-TK, R&D systems) or human P75 (367-NR, R&D systems) was immobilized thereon. As the analyte, a mixture of NGF (0.1 μM) and each aptamer (0.3 μM) was injected after being allowed to stand for 30 minutes. If the aptamer inhibits the binding of NGF and TrkA or p75, the signal on the sensorgram is expected to not rise; if the aptamer does not inhibit the binding, a triple complex will be formed and the signal is expected to rise. When NGF binds stronger to a receptor than an aptamer, the aptamer may be removed and NGF may bind to the receptor. Before starting the inhibition experiment, binding of TrkA or p75 and NGF was confirmed.

The inhibitory activity of 34 sequences was measured to find that all aptamers inhibit the binding of NGF and TrkA or p75. Particularly, the aptamers shown by SEQ ID NOs: 1, 2, 3, 4, 5, 7 showed a strong inhibitory activity. From the above, it was shown that these RNAs are aptamers that inhibit the binding of NGF and NGF receptor.

Example 3

Neurite Outgrowth Inhibitory Activity of Aptamer

The neurite outgrowth inhibitory activity of the aptamer obtained in Example 1 was evaluated by using Neuroscreen-1 cell, which is a subclone of PC-12 cells.

The cells (2500 cells per well) were cultured for one day in an RPMI-1640 medium containing 2.5% horse serum and 1.25% fetal bovine serum in a 96 well flat-bottom plate coated with collagen type IV. A mixed solution of human NGF (final concentration 0.38 nM or 1.14 nM) and an aptamer (final concentration 500-0.01 nM), which had been prereacted in a serum-free RPMI-1640 medium at room temperature or 37° C. for 30 min to 1 hr, was added. Two days later, the cytoplasm and nuclei were stained using Cellomics Neurite Outgrowth Kit (manufactured by Thermo Scientific), and neurite length per cell was measured by Cellomics ArrayScan VTI (manufactured by Thermo Scientific). With the neurite length per cell obtained by the addition of NGF alone as inhibitory activity 0%, and that of the cell obtained by NGF free culture for 2 days as inhibitory activity 100%, the inhibitory activity of the aptamer was calculated from the neurite length per cell obtained by culturing with the addition of NGF and the aptamer in mixture.

The inhibitory activity of the 34 kinds of aptamers obtained in Example 1 was measured to find that the aptamers shown by SEQ ID NOs: 1-8 strongly inhibit neurite outgrowth when 10 nM thereof is added. Other aptamers did not show remarkable inhibition at 10 nM.

The nucleotide sequences actually obtained which correspond to each SEQ ID NO are shown below. The upper-case letters show RNA, lower-case letters show DNA, the parentheses in the nucleotides show the modification at the 2'-position and F is a fluorine atom (hereinafter the same).

SEQ ID NO: 1:
GGGaGaaC(F)U(F)U(F)C(F)GaC(F)C(F)aGaaGU(F)U(F)GaC
(F)GaC(F)C(F)aaC(F)U(F)C(F)GU(F)C(F)U(F)C(F)U(F)U
(F)aU(F)GGaU(F)U(F)U(F)aC(F)GU(F)GaaC(F)C(F)C(F)GU
(F)aU(F)GU(F)GC(F)GC(F)aU(F)aC(F)aU(F)GGaU(F)C(F)C
(F)U(F)C(F)

SEQ ID NO: 2:
GGGaGaaC(F)U(F)U(F)C(F)GaC(F)C(F)aGaaGU(F)C(F)C(F)
aaaC(F)GGGaC(F)U(F)U(F)U(F)aU(F)aC(F)C(F)U(F)C(F)U
(F)GaGU(F)C(F)GC(F)C(F)U(F)aC(F)GC(F)C(F)U(F)C(F)C(F)U
(F)aU(F)GU(F)GC(F)GC(F)aU(F)aC(F)aU(F)GGaU(F)C(F)C
(F)U(F)C(F)

SEQ ID NO: 3:
GGGaGaaC(F)U(F)U(F)C(F)GaC(F)C(F)aGaaGU(F)U(F)GGC
(F)aC(F)aU(F)C(F)C(F)U(F)GC(F)U(F)GC(F)GU(F)aGU(F)
U(F)U(F)C(F)C(F)GU(F)C(F)U(F)C(F)C(F)GU(F)GGC(F)U
(F)GU(F)U(F)aU(F)GU(F)GC(F)GC(F)aU(F)aC(F)aU(F)GG
aU(F)C(F)C(F)U(F)C(F)

SEQ ID NO: 4:
GGGaGaaC(F)U(F)U(F)C(F)GaC(F)C(F)aGaaGU(F)aC(F)GU
(F)U(F)aGU(F)aC(F)GU(F)U(F)U(F)GC(F)aU(F)aU(F)GU
(F)aC(F)aaC(F)C(F)U(F)U(F)GC(F)aU(F)aC(F)GaU(F)aC
(F)GU(F)aGaU(F)U(F)aU(F)GU(F)GC(F)GC(F)aU(F)aC(F)
aU(F)GGaU(F)C(F)C(F)U(F)C(F)

SEQ ID NO: 5:
GGGaGaaC(F)U(F)U(F)C(F)GaC(F)C(F)aGaaGU(F)U(F)aGa
aGaGGaC(F)U(F)aGU(F)U(F)GC(F)U(F)aaU(F)aC(F)C(F)C
(F)U(F)GGU(F)U(F)C(F)GU(F)C(F)GC(F)U(F)aU(F)aU(F)
GU(F)GC(F)GC(F)aU(F)aC(F)aU(F)GGaU(F)C(F)C(F)U(F)
C(F)

SEQ ID NO: 6:
GGGaGaaC(F)U(F)U(F)C(F)GaC(F)C(F)aGaaGU(F)GC(F)aaU
(F)aC(F)U(F)U(F)U(F)C(F)GC(F)GGC(F)aU(F)aU(F)GU(F)
GC(F)aaaC(F)C(F)U(F)U(F)GC(F)C(F)aC(F)GaC(F)U(F)aU
(F)GU(F)GC(F)GC(F)aU(F)aC(F)aU(F)GGaU(F)C(F)C(F)U
(F)C(F)

SEQ ID NO: 7:
GGGaGaaC(F)U(F)U(F)C(F)GaC(F)C(F)aGaaGaC(F)GC(F)aC
(F)C(F)U(F)C(F)U(F)U(F)aU(F)C(F)aC(F)aC(F)aU(F)GC
(F)GU(F)C(F)aGC(F)C(F)U(F)U(F)GU(F)GaU(F)aC(F)U(F)
aU(F)GU(F)GC(F)GC(F)aU(F)aC(F)aU(F)GGaU(F)C(F)C(F)
U(F)C(F)

SEQ ID NO: 8:
GGGaGaaC(F)U(F)U(F)C(F)GaC(F)C(F)aGaaGaU(F)C(F)C
(F)aC(F)U(F)GGU(F)aC(F)U(F)aC(F)GU(F)GaC(F)C(F)C
(F)C(F)GC(F)aU(F)aGGC(F)aaU(F)C(F)C(F)U(F)GC(F)U
(F)U(F)aU(F)GU(F)GC(F)GC(F)aU(F)aC(F)aU(F)GGaU(F)
C(F)C(F)U(F)C(F)

Example 4

Shortening of Aptamers

The aptamers shown by SEQ ID NOs: 3 and 6 were subjected to shortening. Using MFOLD program (Zuker, Nucleic Acids Res. 31, 3406-3415, 2003), the secondary structure of RNA was predicted and the chain was shortened while referring to the structure thereof. The shortened form was obtained by chemically synthesizing the DNA of the object sequence and transcribing same using DuraScribe T7 Transcription Kit (manufactured by Epicentre). The transcription product was treated with DNase, the protein was removed by a phenol-chloroform treatment, and RNA was collected by ethanol precipitation. The purity of the recovered RNA was confirmed by polyacrylamide electrophoresis, and the quantity was confirmed by an absorbance measurement method. The actually produced sequences in a shortened form are as described below.

SEQ ID NO: 9: 73-nucleotide RNA which is an
altered form of aptamer shown by SEQ ID NO: 3
GGGaGaaC(F)U(F)U(F)C(F)GaC(F)C(F)aGaaGU(F)U(F)GGC
(F)aC(F)aU(F)C(F)C(F)U(F)GC(F)U(F)GC(F)GU(F)aGU(F)
U(F)U(F)C(F)C(F)GU(F)C(F)U(F)C(F)C(F)GU(F)GGC(F)U
(F)GU(F)U(F)aU(F)GU(F)GC(F)GC(F)aU(F)aC(F)

SEQ ID NO: 10: 68-nucleotide RNA which is an
altered form of aptamer shown by SEQ ID NO: 3
GGGaGaaC(F)U(F)U(F)C(F)GaC(F)C(F)aGaaGU(F)U(F)GGC
(F)aC(F)aU(F)C(F)C(F)U(F)GC(F)U(F)GC(F)GU(F)aGU(F)
U(F)U(F)C(F)C(F)GU(F)C(F)U(F)C(F)C(F)GU(F)GGC(F)U
(F)GU(F)U(F)aU(F)GU(F)GC(F)G SEQ ID NO: 11: 46-nucleotide RNA which is an
altered form of aptamer shown by SEQ ID NO: 3
GGGC(F)aC(F)aU(F)C(F)C(F)U(F)GC(F)U(F)GC(F)GU(F)aG
U(F)U(F)U(F)C(F)C(F)GU(F)C(F)U(F)C(F)C(F)GU(F)GGC
(F)U(F)GU(F)U(F)aU(F)GU(F)GC(F)

SEQ ID NO: 12: 40-nucleotide RNA which is an
altered form of aptamer shown by SEQ ID NO: 3
GGGU(F)C(F)C(F)U(F)GC(F)U(F)GC(F)GU(F)aGU(F)U(F)U
(F)C(F)C(F)GU(F)C(F)U(F)C(F)C(F)GU(F)GGC(F)U(F)GU
(F)U(F)aC(F)C(F)C(F)

SEQ ID NO: 13: 42-nucleotide RNA which is an
altered form of aptamer shown by SEQ ID NO: 3
GGGGU(F)C(F)C(F)U(F)GC(F)U(F)GC(F)GU(F)aGU(F)U(F)
U(F)C(F)C(F)GU(F)C(F)U(F)C(F)C(F)GU(F)GGC(F)U(F)G
U(F)U(F)aC(F)C(F)C(F)

SEQ ID NO: 121: RNA which is an altered form of
aptamer shownby SEQ ID NO: 11 wherein 1 base pair
is removed from stem 2
GGGC(F)aC(F)aU(F)C(F)C(F)U(F)GC(F)GC(F)GU(F)aGU(F)
U(F)U(F)C(F)C(F)GU(F)C(F)U(F)C(F)C(F)GU(F)GC(F)U
(F)GU(F)U(F)aU(F)GU(F)GC(F)

SEQ ID NO: 122: RNA which is an altered form of
aptamer shownby SEQ ID NO: 11 wherein 1 base pair
is removed from stem 2
GGGC(F)aC(F)aU(F)C(F)C(F)U(F)GC(F)U(F)GC(F)GaGU(F)
U(F)U(F)C(F)C(F)GU(F)C(F)U(F)C(F)C(F)GU(F)GGC(F)U(F)GU
(F)U(F)aU(F)GU(F)GC(F)

SEQ ID NO: 123: RNA which is an altered form of
aptamer shown by SEQ ID NO: 11 wherein 1 base pair
is removed from stem 2
GGGC(F)aC(F)aU(F)C(F)C(F)U(F)GU(F)GC(F)GU(F)aGU(F)
U(F)U(F)C(F)C(F)GU(F)C(F)U(F)C(F)C(F)GU(F)GC(F)U
(F)GU(F)U(F)aU(F)GU(F)GC(F)

SEQ ID NO: 124: RNA which is an altered form of
aptamer shown by SEQ ID NO: 11 wherein 1 base pair
is removed from stem 2
GGGC(F)aC(F)aU(F)C(F)C(F)U(F)GC(F)U(F)GGU(F)aGU(F)
U(F)U(F)C(F)C(F)GU(F)C(F)U(F)C(F)C(F)U(F)GGC(F)U
(F)GU(F)U(F)aU(F)GU(F)GC(F)

SEQ ID NO: 125: RNA which is an altered form of
aptamer shown by SEQ ID NO: 11 wherein 1 base pair
is removed from stem 2
GGGC(F)aC(F)aU(F)C(F)C(F)U(F)GC(F)U(F)GC(F)U(F)aGU
(F)U(F)C(F)C(F)GU(F)C(F)U(F)C(F)GU(F)GGC(F)U
(F)GU(F)U(F)aU(F)GU(F)GC(F)

SEQ ID NO: 126: RNA which is an altered form of
aptamer shown by SEQ ID NO: 11 wherein 1 base pair
is removed from stem 2
GGGC(F)aC(F)aU(F)C(F)C(F)U(F)GC(F)U(F)GC(F)GU(F)GU
(F)U(F)U(F)C(F)C(F)GU(F)C(F)C(F)C(F)GU(F)GGC(F)U
(F)GU(F)U(F)aU(F)GU(F)GC(F)

SEQ ID NO: 127: RNA which is an altered form of
aptamer shown by SEQ ID NO: 13 wherein 1 base pair
is removed from stem 2
GGGGU(F)C(F)C(F)U(F)C(F)U(F)GC(F)GU(F)aGU(F)U(F)U
(F)C(F)C(F)GU(F)C(F)U(F)C(F)C(F)GU(F)GGU(F)GU(F)U
(F)aC(F)C(F)C(F)C(F)

SEQ ID NO: 128: RNA which is an altered form of
aptamer shown by SEQ ID NO: 13 wherein 1 base pair
is removed from stem 2
GGGGU(F)C(F)C(F)U(F)GC(F)U(F)GC(F)GU(F)aU(F)U(F)U
(F)C(F)C(F)GU(F)U(F)C(F)C(F)GU(F)GGC(F)U(F)GU(F)U
(F)aC(F)C(F)C(F)C(F)

SEQ ID NO: 129: RNA which is an altered form of
aptamer shown by SEQ ID NO: 13 wherein 1 base pair
is removed from stem 1
GGGGC(F)C(F)U(F)GC(F)U(F)GC(F)GU(F)aGU(F)U(F)U(F)C
(F)C(F)GU(F)C(F)U(F)C(F)C(F)GU(F)GGC(F)U(F)GU(F)U
(F)C(F)C(F)C(F)C(F)

SEQ ID NO: 130: RNA which is an altered form of
aptamer shown by SEQ ID NO: 11 wherein one U is
removed from loop 2
GGGC(F)aC(F)aU(F)C(F)C(F)U(F)GC(F)U(F)GC(F)GU(F)aG
U(F)U(F)C(F)C(F)GU(F)C(F)U(F)C(F)C(F)GU(F)GGC(F)U
(F)GU(F)U(F)aU(F)GU(F)GC(F)

SEQ ID NO: 131: RNA which is an altered form of
aptamer shown by SEQ ID NO: 11 wherein two C's
are removed from loop 2
GGGC(F)aC(F)aU(F)C(F)C(F)U(F)GC(F)U(F)GC(F)0(F)GC(F)G0(F)a
GU(F)U(F)U(F)GU(F)C(F)U(F)C(F)C(F)GU(F)GGC(F)U(F)
GU(F)U(F)aU(F)GU(F)GC(F)

SEQ ID NO: 132: RNA which is an altered form of
aptamer shown by SEQ ID NO: 11 wherein one G is
removed from loop 2
GGGC(F)aC(F)aU(F)C(F)C(F)U(F)GC(F)U(F)GC(F)GU(F)aG
U(F)U(F)U(F)C(F)C(F)U(F)C(F)U(F)C(F)C(F)GU(F)GGC
(F)U(F)GU(F)U(F)aU(F)GU(F)GC(F)

SEQ ID NO: 133: RNA which is an altered form of
aptamer shown by SEQ ID NO: 13 wherein one U is
removed from loop 2
GGGGU(F)C(F)C(F)U(F)GC(F)U(F)GC(F)GU(F)aGU(F)U(F)
U(F)C(F)C(F)GC(F)U(F)C(F)C(F)GU(F)GGC(F)U(F)GU(F)
U(F)aC(F)C(F)C(F)C(F)

SEQ ID NO: 134: RNA which is an altered form of
aptamer shown by SEQ ID NO: 11 wherein one U is
removed from internal loop 1
GGGC(F)aC(F)aU(F)C(F)C(F)U(F)GC(F)U(F)GC(F)GU(F)a
GU(F)U(F)U(F)C(F)C(F)GU(F)C(F)U(F)C(F)C(F)GU(F)GG
C(F)U(F)GU(F)aU(F)GU(F)GC(F)

SEQ ID NO: 135: RNA which is an altered form of
aptamer shown by SEQ ID NO: 13 wherein one C is
removed from internal loop 1
GGGGU(F)C(F)U(F)GC(F)U(F)GC(F)GU(F)aGU(F)U(F)U(F)
C(F)C(F)GU(F)C(F)U(F)C(F)C(F)GU(F)GGC(F)U(F)GU(F)
U(F)aC(F)C(F)C(F)C(F)

SEQ ID NO: 136: RNA which is an altered form of
aptamer shown by SEQ ID NO: 13 wherein one U is
removed from internal loop 1
GGGGU(F)C(F)C(F)GC(F)U(F)GC(F)GU(F)aGU(F)U(F)U(F)
C(F)C(F)GU(F)C(F)U(F)C(F)C(F)GU(F)GGC(F)U(F)GU(F)
U(F)aC(F)C(F)C(F)C(F)

SEQ ID NO: 137: RNA which is an altered form of
aptamer shown by SEQ ID NO: 13 wherein one C and
one U are removed from internal loop 1
GGGGU(F)C(F)U(F)GC(F)U(F)GC(F)GU(F)aGU(F)U(F)U(F)
C(F)C(F)GU(F)C(F)U(F)C(F)C(F)GU(F)GGC(F)U(F)GU(F)
aC(F)C(F)C(F)C(F)

SEQ ID NO: 138: RNA which is an altered form of
aptamer shown by SEQ ID NO: 13 wherein one C and
one G are removed from internal loop 1
GGGGU(F)C(F)U(F)GC(F)U(F)GC(F)GU(F)aGU(F)U(F)U(F)
C(F)C(F)GU(F)C(F)U(F)C(F)C(F)GU(F)GGC(F)U(F)U(F)U
(F)aC(F)C(F)C(F)C(F)

SEQ ID NO: 139: RNA which is an altered form of
aptamer shown by SEQ ID NO: 13 wherein two U's
are removed from internal loop 1
GGGGU(F)C(F)C(F)GC(F)U(F)GC(F)GU(F)aGU(F)U(F)U(F)C
(F)GU(F)C(F)U(F)C(F)C(F)GU(F)GGC(F)GU(F)U(F)aC
(F)C(F)C(F)C(F)

SEQ ID NO: 140: RNA which is an altered form of
aptamer shown by SEQ ID NO: 13 wherein one U and
one G are removed from internal loop 1
GGGGU(F)C(F)C(F)GC(F)U(F)GC(F)GU(F)aGU(F)U(F)U(F)
C(F)C(F)GU(F)C(F)U(F)C(F)C(F)GU(F)GGC(F)U(F)U(F)U
(F)aC(F)C(F)C(F)C(F)

SEQ ID NO: 141: RNA which is an altered form of
aptamer shown by SEQ ID NO: 13 wherein two U's
are removed from internal loop 1
GGGGU(F)C(F)C(F)GC(F)U(F)GC(F)GU(F)aGU(F)U(F)U(F)
C(F)C(F)GU(F)C(F)U(F)C(F)C(F)GU(F)GGC(F)U(F)GU(F)
aC(F)C(F)C(F)C(F)

SEQ ID NO: 14: 78-nucleotide aptamer which is an
altered form of aptamer shown by SEQ ID NO: 6
GGGaGaaC(F)U(F)U(F)C(F)GaC(F)C(F)aGaaGU(F)GC(F)aaU
(F)aC(F)U(F)U(F)U(F)C(F)GC(F)GGC(F)aU(F)aU(F)GU(F)
GC(F)aaaC(F)C(F)U(F)U(F)U(F)GC(F)C(F)aC(F)GaC(F)U(F)aU
(F)GU(F)GC(F)GC(F)aU(F)aC(F)aU(F)GGa SEQ ID NO: 15: 73-nucleotide aptamer which is an
altered form of aptamer shown by SEQ ID NO: 6
GGGaGaaC(F)U(F)U(F)C(F)GaC(F)C(F)aGaaGU(F)GC(F)aaU
(F)aC(F)U(F)U(F)U(F)C(F)GC(F)GGC(F)aU(F)aU(F)GU(F)
GC(F)aaaC(F)C(F)U(F)U(F)GC(F)C(F)aC(F)GaC(F)U(F)aU
(F)GU(F)GC(F)GC(F)aU(F)aC(F)

SEQ ID NO: 16: 63-nucleotide aptamer which is an
altered form of aptamer shown by SEQ ID NO: 6
C(F)GaC(F)C(F)aGaaGU(F)GC(F)aaU(F)aC(F)U(F)U(F)U
(F)C(F)GC(F)GGC(F)aU(F)aU(F)GU(F)GC(F)aaaC(F)C(F)
U(F)U(F)GC(F)C(F)aC(F)GaC(F)U(F)aU(F)GU(F)GC(F)GC
(F)aU(F)aC(F)

-continued

SEQ ID NO: 17: 58-nucleotide aptamer which is an
altered form of aptamer shown by SEQ ID NO: 6
aGaaGU(F)GC(F)aaU(F)aC(F)U(F)U(F)U(F)C(F)GC(F)GGC
(F)aU(F)aU(F)GU(F)GC(F)aaaC(F)C(F)U(F)U(F)GC(F)C
(F)aC(F)GaC(F)U(F)aU(F)GU(F)GC(F)GC(F)aU(F)aC(F)

SEQ ID NO: 18: 48-nucleotide aptamer which is an
altered form of aptamer shown by SEQ ID NO: 6
U(F)GC(F)aaU(F)aC(F)U(F)U(F)U(F)C(F)GC(F)GGC(F)aU
(F)aU(F)GU(F)GC(F)aaaC(F)C(F)U(F)U(F)GC(F)C(F)aC
(F)GaC(F)U(F)aU(F)GU(F)GC(F)G SEQ ID NO: 19: 46-nucleotide aptamer which is an
altered form of aptamer shown by SEQ ID NO: 6
GC(F)aaU(F)aC(F)U(F)U(F)U(F)C(F)GC(F)GGC(F)aU(F)aU
(F)GU(F)GC(F)aaaC(F)C(F)U(F)U(F)GC(F)C(F)aC(F)GaC
(F)U(F)aU(F)GU(F)GC(F)

SEQ ID NO: 20: 50-nucleotide aptamer which is an
altered form of aptamer shown by SEQ ID NO: 6
GU(F)GC(F)aaU(F)aC(F)U(F)U(F)U(F)C(F)GC(F)GGC(F)aU
(F)aU(F)GU(F)GC(F)aaaC(F)C(F)U(F)U(F)GC(F)C(F)aC
(F)GaC(F)U(F)aU(F)GU(F)GC(F)GC(F)

SEQ ID NO: 21: 48-nucleotide aptamer which is an
altered form of aptamer shown by SEQ ID NO: 6
GGGaaU(F)aC(F)U(F)U(F)U(F)C(F)GC(F)GGC(F)aU(F)aU
(F)GU(F)GC(F)aaaC(F)C(F)U(F)U(F)GC(F)C(F)aC(F)GaC
(F)U(F)aU(F)GU(F)C(F)C(F)C(F)

The binding activity of these aptamers to NGF was evaluated by the surface plasmon resonance method in the same manner as in Example 1. As a result, RNAs shown by SEQ ID NOs: 9-21 were found to bind more significantly to NGF than 40N of is the control. On the other hand, the binding amount of RNAs shown by SEQ ID NOs: 121-141 markedly decreased as compared to the aptamer shown by SEQ ID NO: 11 or 13.

The inhibition of the binding of NGF to receptors thereof (TrkA and p75) was evaluated by the surface plasmon resonance method in the same manner as in Example 2 to find that the aptamers shown by SEQ ID NOs: 9-16 have a high inhibitory activity.

The neurite outgrowth inhibitory activity was examined by a method similar to Example 3 to find that the aptamers shown by SEQ ID NOs: 9-21 show a high inhibitory activity at a concentration of 10 nM. On the other hand, the aptamers shown by SEQ ID NOs: 127, 128, 131, 133, 135, 141 did not show a remarkable inhibitory activity at 10 nM.

Example 5

Figure 2:
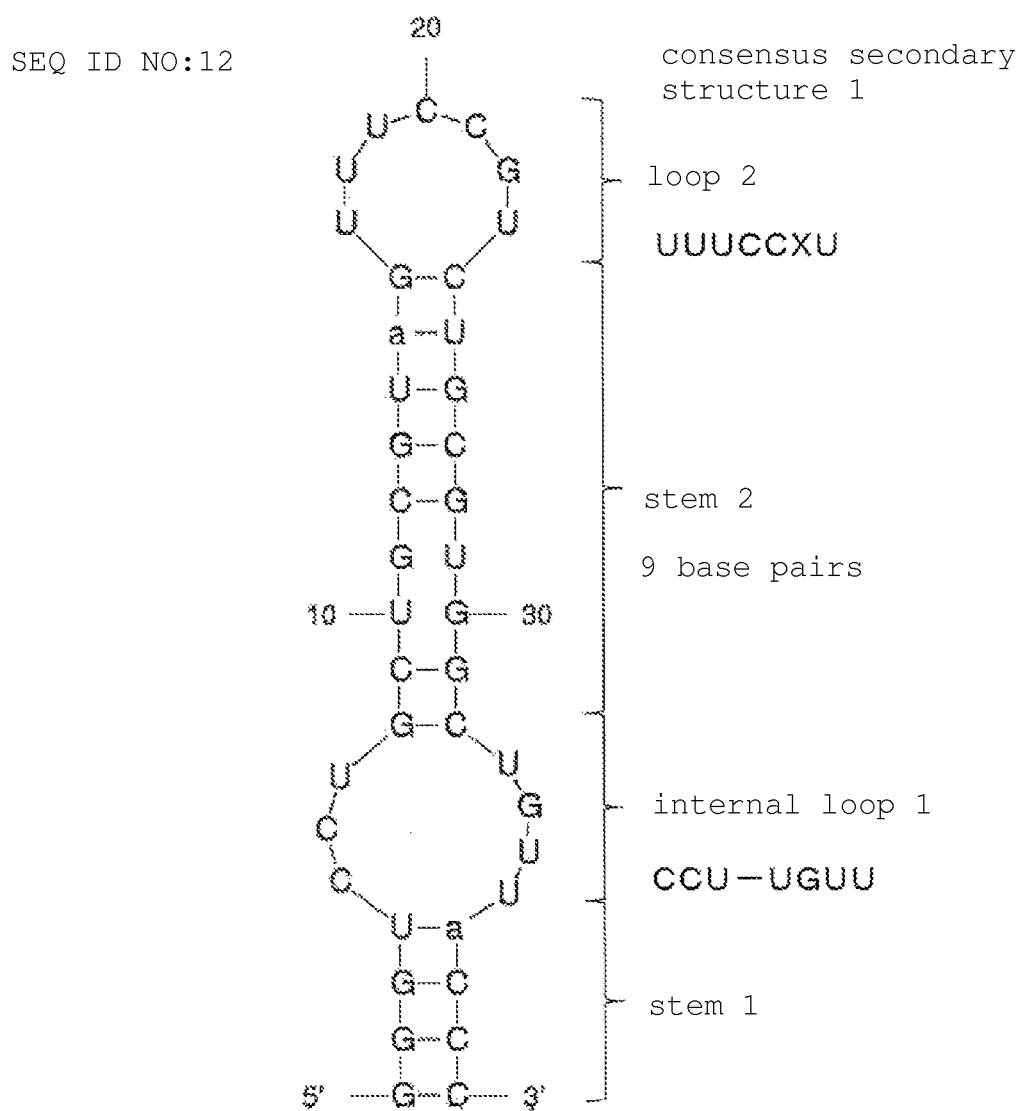
FIG. 2 is a schematic diagram of consensus secondary structure 1 represented by the nucleotide sequence of the NGF aptamer shown by SEQ ID NO: 12.
Figure 3:
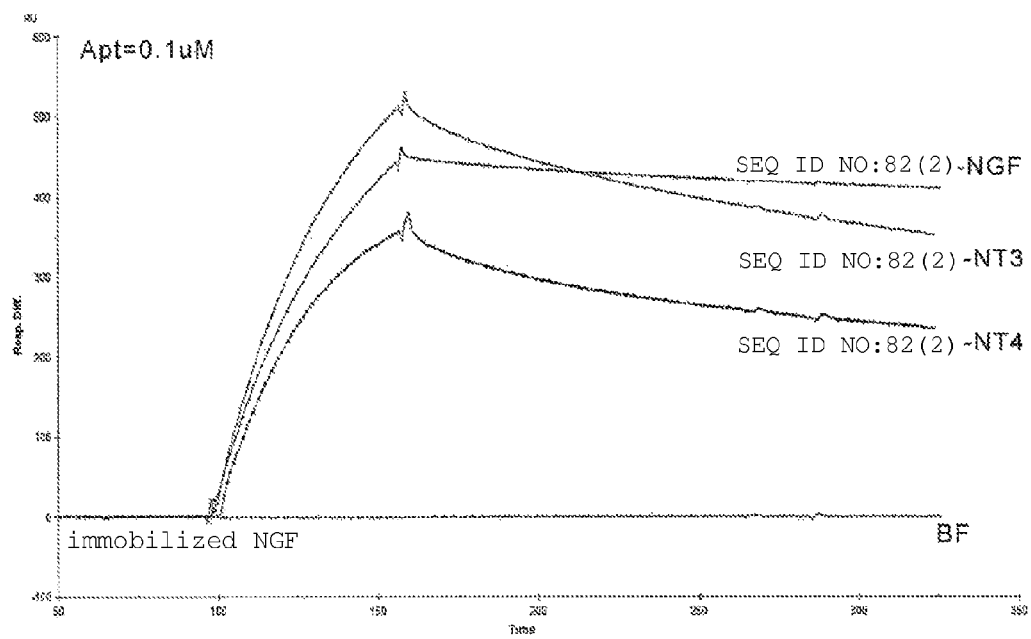
FIG. 3 is a sensorgram showing that the NGF aptamer shown by SEQ ID NO: 82(2) (modified form) binds to NGF, NT-3 and NT-4, wherein RU on the vertical axis shows a relative unit, Resp.Diff. shows response differences, and the horizontal axis shows time (seconds) (Time(s)). These notations on the vertical axis and the horizontal axis are the same in the following FIGS. 4-5.
Figure 4:
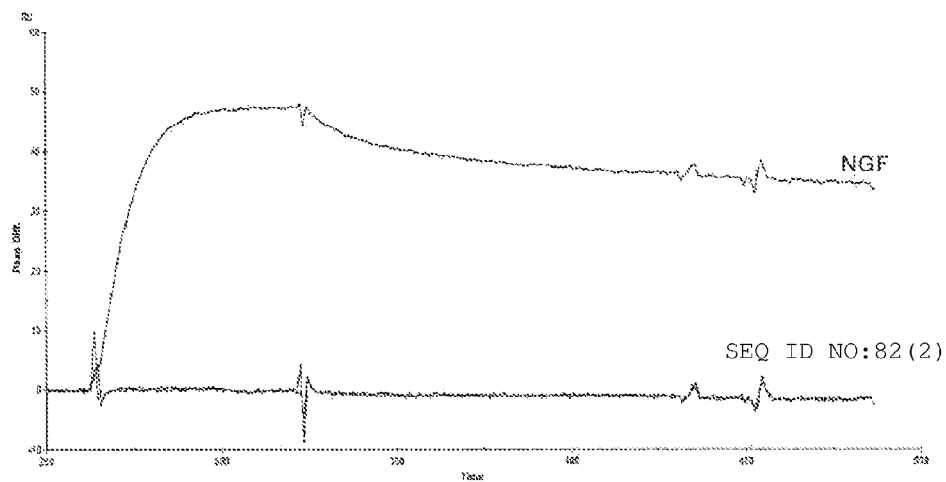
FIG. 4 is a sensorgram showing that the NGF aptamer shown by SEQ ID NO: 82(2) (modified form) inhibits binding of NGF and NGF receptor TrkA.
Figure 5:
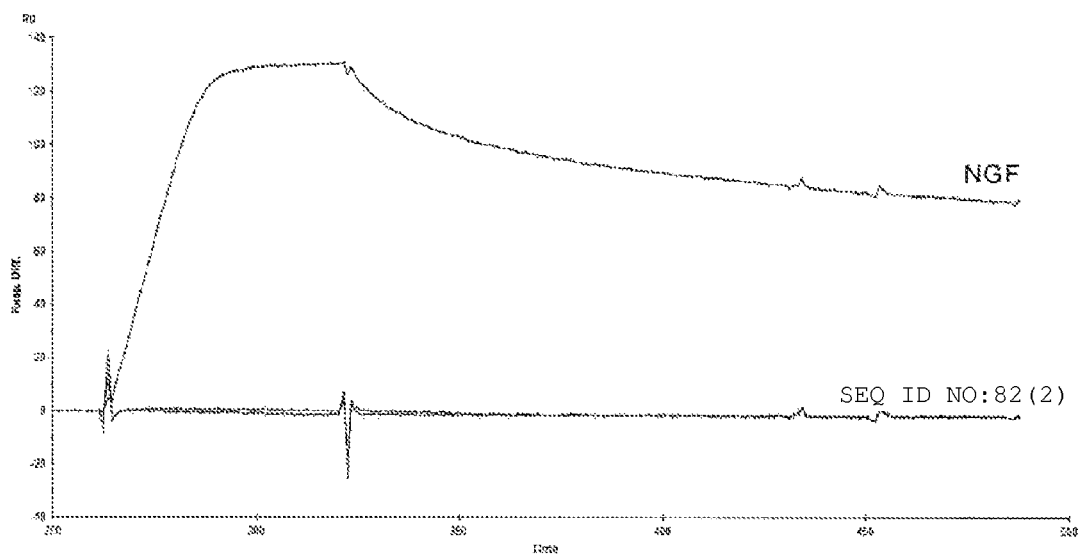
FIG. 5 is a sensorgram showing that the NGF aptamer shown by SEQ ID NO: 82(2) (modified form) inhibits binding of NGF and NGF receptor p75.

Prediction of Secondary Structure of Aptamer Shown by SEQ ID NO: 3 and Shortened Form Thereof The secondary structure of RNAs shown by SEQ ID NOs: 3, 9-13 and SEQ ID NOs: 121-141 was predicted using MFOLD program. All aptamers having activity contained the secondary structure of the aptamer shown by SEQ ID NO: 12 (FIG. 1). The secondary structure was characterized by 4 structures of stem 1, internal loop 1, stem 2 and loop 2, from the 5' end (FIG. 2). Stem 1 consists of 4 base pairs, internal loop 1 consists of 3 nucleotides and 4 nucleotides, stem 2 consists of 9 base pairs, and loop 2 consists of 7 nucleotides.

All activities of the RNAs shown by SEQ ID NOs: 121-128 wherein 1 base pair is removed from stem 2 markedly decreased. Therefore, it was suggested that stem 2 requires 9 base pairs.

The aptamers shown by SEQ ID NOs: 12 and 13 are altered forms of the aptamer shown by SEQ ID NO: 11, wherein stem 1 is substituted by G-C pair. The aptamers shown by SEQ ID NOs: 12 and 13 showed a neurite outgrowth inhibitory activity equivalent to that of SEQ ID NO: 11. Therefore, it was suggested that the activity is not markedly influenced by the base pair as long as stem 1 is a stem structure. On the other hand, the activity of RNA shown by SEQ ID NO: 129, which is an aptamer shown by SEQ ID NO: 13 wherein U-a base pair is removed from stem 1, markedly decreased. Therefore, it was found that the 4th base pair of stem 1 needs to be U-a.

RNAs shown by SEQ ID NOs: 130-133 wherein one nucleotide is removed from loop 2 all showed markedly decreased activity. Therefore, it was suggested that loop 2 needs to consist of 7 nucleotides.

RNAs shown by SEQ ID NOs: 134-141 wherein 1 or 2 nucleotides of internal loop 1 were removed all showed markedly decreased activity. Therefore, it was suggested that internal loop 1 needs to consist of total 7 nucleotides.

The structure specified in FIG. 2 is hereinafter to be referred to as the consensus secondary structure 1.

Example 6

Production of NGF Aptamer—2

Using a primer different from that in Example 1, SELEX was performed, and whether an aptamer having a consensus secondary structure 1 can be obtained was studied. The DNA template and the primer sequences used are shown below.

DNA template 2:
(SEQ ID NO: 142)
5'-ccagttgttggtgacaatgcnnnnnnnnnnnnnnnnnnnnnnnnnnn
nnnnnnnnnnnnnngcagctccacaggcttccc primer Fwd2:
(SEQ ID NO: 143)
5'-taatacgactcactatagggaagcctgtggagctgc primer Rev2:
(SEQ ID NO: 144)
5'-gcattgtcaccaacaactgg In the above-mentioned sequences, n represents any one of a, g, c and t. The primer Fwd2 comprises a promoter sequence of T7 RNA polymerase. The variation of the RNA pool used in the first round was theoretically $10^{14}$.

SELEX was performed in the same manner as in Example 1. After 10 rounds of SELEX, 48 clones were examined and 46 sequences could be sequenced. Among them were 1 sequence wherein 5 clones are the same, 4 sequences wherein 3 clones are the same, and 3 sequences wherein 2 clones are the same, and a total of 8 sequences showed convergence. The remaining 23 sequences were single sequences.

8 sequences showing convergence were selected, and the binding activity to NGF was evaluated by the surface plasmon resonance method. The measurement method was similar to Example 1. As a result, all sequences bound to NGF only slightly.

The secondary structure of all sequences including single sequences was predicted using an MFOLD program to find no sequence containing consensus secondary structure 1.

Example 7

Production of NGF Aptamer—3

SELEX was performed using an RNA pool containing a sequence shown by SEQ ID NO: 12 doped with 15% random sequence and added with primer sequences, similar to those in Example 1, to the both ends thereof. SELEX was performed almost in the same manner as in Example 1. The sequences of the template are shown below.

template 3:
(SEQ ID NO: 145)
5'-gaggatccatgtatgcgcacata-

<u>acagccacggagacggaaactacgcagcaggatgtgccaa</u>-cttctgg tcgaagttctccc-3'

In the sequence, the underlined base sequence is as described below.
<u>a</u>: a(85%), g(5%), c(5%), t(5%)
<u>g</u>: a(5%), g(85%), c(5%), t(5%)
<u>c</u>: a(5%), g(5%), c(85%), t(5%)
<u>t</u>: a(5%), g(5%), c(5%), t(85%)

After the completion of 4 rounds, the sequence of 48 clones was confirmed to find that about half was a sequence containing SEQ ID NO: 12 and the rest was a sequence with mutations at several sites. To remove the same sequence as SEQ ID NO: 12, antisense oligo of SEQ ID NO: 12 was added to the RNA pool, and SELEX was performed for 3 more rounds. The sequence of antisense oligo is as described below. 5'-agacggaaactacgcagcagga-3'-(SEQ ID NO: 146)

The antisense oligo was added in a 10-fold amount relative to the RNA pool. The sequence of the obtained RNA was confirmed to find that about half was a sequence shown by SEQ ID NO: 12 with mutations at several sites and the rest was a sequence completely different from the sequence shown by SEQ ID NO: 12.

A total of 16 sequences shown by SEQ ID NOs: 22-37 were selected from 4 and 7 rounds, and the binding activity to NGF and the inhibitory activity against the binding of NGF and NGF receptor were examined. The measurement was as shown in Examples 1 and 2 and the surface plasmon resonance method was used. As a result of the measurement, it was found that all sequences more significantly bind to NGF than 40N of the control, and inhibit the binding of NGF and NGF receptor. In addition, the neurite outgrowth inhibitory activity was measured by a method similar to that in Example 3. As a result, all sequences showed a high inhibitory activity at a concentration of 10 nM. The nucleotide sequences actually obtained, which correspond to each SEQ ID NO, are shown below.

```
SEQ ID NO: 22:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GU(F)aGU(F)U(F)U(F)C(F)C(F)GU(F)C(F)U
(F)U(F)C(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 23:
GGGaGaaC(F)U(F)U(F)C(F)GaC(F)C(F)aGaaGU(F)GGC(F)aC(F)aU(F)C(F)C
(F)U(F)GC(F)U(F)GC(F)GU(F)aGU(F)U(F)U(F)C(F)C(F)GU(F)C(F)U(F)GC
(F)GU(F)GGC(F)U(F)GU(F)U(F)aU(F)GU(F)GC(F)GC(F)aU(F)aC(F)aU(F)G
GaU(F)C(F)C(F)U(F)C(F)

SEQ ID NO: 24:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GaaGU(F)U(F)U(F)C(F)C(F)GU(F)C(F)U(F)C
(F)C(F)GU(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 25:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GC(F)aGU(F)U(F)U(F)C(F)C(F)GU(F)C(F)U
(F)aC(F)GU(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 26:
GGGaGaaC(F)U(F)U(F)C(F)GaC(F)C(F)aGaaGU(F)GGC(F)aC(F)aU(F)C(F)C
(F)U(F)GC(F)U(F)GC(F)GU(F)aGU(F)U(F)U(F)C(F)C(F)GU(F)C(F)U(F)U
(F)C(F)GC(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 27:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GC(F)aGU(F)U(F)U(F)C(F)C(F)GU(F)C(F)U
(F)GC(F)GU(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 28:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GU(F)aGU(F)U(F)U(F)C(F)C(F)aU(F)C(F)U
(F)GC(F)GU(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 29:
GGGaGaaC(F)U(F)U(F)C(F)GaC(F)C(F)aGaaGU(F)U(F)C(F)aC(F)aU(F)C(F)
C(F)U(F)GC(F)U(F)GC(F)GaaGU(F)U(F)U(F)C(F)C(F)U(F)U(F)C(F)U(F)
U(F)C(F)GU(F)GGC(F)U(F)GU(F)U(F)aU(F)GU(F)GC(F)GC(F)aU(F)aC(F)a
U(F)GGaU(F)C(F)C(F)U(F)C(F)
```

-continued

SEQ ID NO: 30:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GaaGGU(F)U(F)C(F)C(F)GU(F)C(F)U(F)U(F)
C(F)GU(F)GGC(F)U(F)GU(F)aC(F)U(F)aU(F)GU(F)GC(F)GC(F)aU(F)aC(F)
aU(F)GGaU(F)C(F)C(F)U(F)C(F)

SEQ ID NO: 31:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GC(F)aGU(F)U(F)U(F)C(F)C(F)C(F)U(F)C(F)
U(F)GC(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 32:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GGaGU(F)U(F)U(F)C(F)C(F)U(F)U(F)C(F)U
(F)U(F)C(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 33:
GGGaGaaC(F)U(F)U(F)C(F)GaC(F)C(F)aGaaGU(F)U(F)GGC(F)aC(F)aU(F)C
(F)C(F)U(F)GC(F)C(F)GC(F)GU(F)aGU(F)U(F)U(F)C(F)aaU(F)C(F)U(F)U
(F)GGU(F)GGC(F)GU(F)GU(F)aU(F)GU(F)GC(F)GC(F)aU(F)aC(F)aU(F)GGa
U(F)C(F)C(F)U(F)C(F)

SEQ ID NO: 34:
GGGaGaaC(F)U(F)U(F)C(F)GaC(F)C(F)aGaaGU(F)U(F)GGC(F)aC(F)aU(F)C
(F)C(F)U(F)GC(F)C(F)GC(F)GU(F)aGU(F)U(F)U(F)C(F)C(F)GU(F)C(F)U
(F)GC(F)GU(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 35:
GGGaGaaC(F)U(F)U(F)C(F)GaC(F)C(F)aGaaGU(F)U(F)GGC(F)aC(F)aU(F)C
(F)C(F)U(F)GU(F)U(F)GC(F)GU(F)aGU(F)U(F)U(F)C(F)C(F)U(F)U(F)C(F)
U(F)aC(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 36:
GGGaGaaC(F)U(F)U(F)C(F)GaC(F)C(F)aGaaGGU(F)aC(F)GU(F)U(F)aGU(F)
aC(F)GU(F)U(F)U(F)GC(F)aU(F)aU(F)GU(F)aC(F)aaC(F)C(F)U(F)U(F)GC
(F)aU(F)aC(F)GaU(F)aC(F)GU(F)aGGU(F)U(F)aU(F)GU(F)GC(F)GC(F)aU
(F)aC(F)aU(F)GGaU(F)C(F)C(F)U(F)C(F)

SEQ ID NO: 37:
GGGaGaaC(F)U(F)U(F)C(F)GaC(F)C(F)aGaaGU(F)U(F)GGC(F)aC(F)aU(F)C
(F)C(F)U(F)GC(F)U(F)aC(F)GU(F)aGU(F)U(F)U(F)C(F)C(F)U(F)U(F)C(F)
U(F)U(F)C(F)GU(F)GGC(F)U(F)GU(F)U(F)aU(F)GU(F)GC(F)GC(F)aU(F)a
C(F)aU(F)GGaU(F)C(F)C(F)U(F)C(F)

The secondary structure of the aptamers shown by SEQ ID NOs: 22-37 was predicted using the MFOLD program to find that all aptamers other than the aptamers shown by SEQ ID NOs: 30, 33, 36 contain consensus secondary structure 1. The 5' side of all the sequences of the internal loops 1 was CCU and the 3' side was UGUU (FIG. 2). In addition, loop 2 contained a consensus sequence shown by 5'-UUUCCXU-3'. Here, X is any of A, G, C and U. All the final base pair of stem 1 was U-a. The 1st, 5th, 6th, 8th and 9th base pairs of stem 2 were G-C, C-G, G-C, a-U and G-C, respectively. The 2nd-4th and 7th contained some different base pairs.

Example 8

Cell Proliferation Inhibitory Activity of Aptamer (TF-1 Assay)

The inhibitory activities of the aptamers shown by SEQ NOs. 22 to 37 were evaluated by a proliferation inhibition assay using TF-1 cells.

Two NGF receptor (human TrkA and human p75) genes were introduced into TF-1 cells (ATCC Number: CRL-2003), which is a human erythroleukemic cell line, by using a retrovirus vector to give cells that highly express two receptors simultaneously and stably. The cells were suspended in an RPMI-1640 medium containing 20% fetal bovine serum, and seeded in a white 96 well flat-bottom plate at 1000 cells (50 μL) per well. Thereto was added a mixed solution 50 μL of human NGF (final concentration 0.076 nM) and the aptamer (final concentration 30-0.01 nM), which had been pre-reacted at room temperature for 30 min in a serum-free RPMI-1640 medium, 3 days later, 100 μL of CellTiter-Glo reagent for CeliTiter-Glo Luminescent Cell Viability Assay (manufactured by Promega) was added to each well, chemiluminescence was measured by a microplate reader and the growth of TF-1 cells by NGF stimulation was evaluated. With the amount of luminescence per well obtained by the addition of NGF alone and culture of the cells for 3 days as inhibitory activity 0%, and that of the well obtained by NGF free culture for 3 days as inhibitory activity 100%, the inhibitory activity of the aptamer was calculated from the amount of luminescence per well obtained by culturing with the addition of NGF and the aptamer in mixture. As a result, it was found that all these aptamers show a high inhibitory activity at a concentration of 10 nM.

The inhibitory activity of the aptamers shown by SEQ ID NO: 62 and 68 described in WO 2010/035725A1 was examined for comparison. As a result, $IC_{50}$ was 6.1 and 7.5 nM, respectively.

Example 9

Shortening of Aptamer—2

The aptamers shown by SEQ ID NOs: 23, 25, 26, 27, 28, 29, 31, 32, 34 and 35 that showed a high inhibitory activity were subjected to shortening by reference to the consensus secondary structure 1. The binding activity to NGF was measured by the surface plasmon resonance method in the same manner as in Example 1 to find that all shortened forms strongly bound to NGF. In addition, the neurite outgrowth inhibitory activity and TF-1 cell proliferation inhibitory activity were measured by a method similar to that in Examples 3 and B to find a strong inhibitory activity at a concentration of 10 nM. The nucleotide sequences actually obtained are shown below.

```
SEQ ID NO: 38: (shortened form of SEQ ID NO: 26)
GGGU(F)C(F)C(F)U(F)GC(F)U(F)GC(F)GU(F)aGU(F)U(F)U(F)C(F)C(F)GU
(F)C(F)U(F)U(F)C(F)GC(F)GGC(F)U(F)GU(F)U(F)aC(F)C(F)C(F)

SEQ ID NO: 39: (shortened form of SEQ ID NO: 27)
GGGU(F)C(F)C(F)U(F)GC(F)U(F)GC(F)GC(F)aGU(F)U(F)U(F)C(F)C(F)GU
(F)C(F)U(F)GC(F)GU(F)GGC(F)U(F)GU(F)U(F)aC(F)C(F)C(F)

SEQ ID NO: 40: (shortened form of SEQ ID NO: 28)
GGGU(F)C(F)C(F)U(F)GC(F)U(F)GC(F)GU(F)aGU(F)U(F)U(F)C(F)C(F)aU
(F)C(F)U(F)GC(F)GU(F)GGC(F)U(F)GU(F)U(F)aC(F)C(F)C(F)

SEQ ID NO: 41:
GGGU(F)C(F)C(F)U(F)GC(F)U(F)GC(F)GaaGU(F)U(F)U(F)C(F)C(F)U(F)U
(F)C(F)U(F)U(F)C(F)GU(F)GGC(F)U(F)GU(F)U(F)aC(F)C(F)C(F)

SEQ ID NO: 42:
GGGU(F)C(F)C(F)U(F)GC(F)U(F)GC(F)GC(F)aGU(F)U(F)U(F)C(F)C(F)C(F)
U(F)C(F)U(F)GC(F)GU(F)GGC(F)U(F)GU(F)U(F)aC(F)C(F)C(F)

SEQ ID NO: 43:
GGGU(F)C(F)C(F)U(F)GC(F)U(F)GC(F)GGaGU(F)U(F)U(F)C(F)C(F)U(F)U
(F)C(F)U(F)U(F)C(F)GU(F)GGC(F)U(F)GU(F)U(F)aC(F)C(F)C(F)

SEQ ID NO: 44:
GGGU(F)C(F)C(F)U(F)GC(F)C(F)GC(F)GU(F)aGU(F)U(F)U(F)C(F)C(F)GU
(F)C(F)U(F)GC(F)GU(F)GGC(F)U(F)GU(F)U(F)aC(F)C(F)C(F)

SEQ ID NO: 45:
GGGU(F)C(F)C(F)U(F)GU(F)U(F)GC(F)GU(F)aGU(F)U(F)U(F)C(F)C(F)U(F)
U(F)C(F)U(F)aC(F)GU(F)GGC(F)U(F)GU(F)U(F)aC(F)C(F)C(F)

SEQ ID NO: 46: (shortened form of SEQ ID NO: 25)
GGGU(F)C(F)C(F)U(F)GC(F)U(F)GC(F)GC(F)aGU(F)U(F)U(F)C(F)C(F)GU
(F)C(F)U(F)aC(F)GU(F)GGC(F)U(F)GU(F)U(F)aC(F)C(F)C(F)

SEQ ID NO: 47: (shortened form of SEQ ID NO: 26)
GGGU(F)C(F)C(F)U(F)GC(F)U(F)GC(F)GU(F)aGU(F)U(F)U(F)C(F)C(F)GU
(F)C(F)U(F)U(F)C(F)GC(F)GGC(F)U(F)GU(F)U(F)aC(F)C(F)C(F)
```

The secondary structure of these aptamers was predicted using the MFOLD program to find that all of them had a structure shown by the consensus secondary structure 1.

Example 10

Production of NGF Aptamer—4

SELEX was performed using an RNA pool containing a sequence shown by SEQ ID NO: 12 doped with 21% random sequence and added with primer sequences, similar to those in Example 1, to the both ends thereof. SELEX was performed in the same manner as in Example 1. The sequence of the template is shown below.

```
template 3:                                    (SEQ ID NO: 145)
5'-gaggatccatgtatgcgcacata-
acagccacggagacggaaactacgcagcaggatgtgccaa-cttctgg
tcgaagttctccc-3'
```

In the sequence, the underlined base sequence is as described below.

a: a(79%), g(7%), c(7%), t(7%)
g: a(7%), g(79%), c(7%), t(7%)
c: a(7%), g(7%), c(79%), t(7%)
t: a(7%), g(7%), c(7%), t(79%)

After the completion of 4 rounds, the sequences of 48 clones were confirmed, but sequence convergence was not seen. Thus, 3 more rounds were performed. At 5, 6, 7 rounds, the sequences of 48 clones were confirmed to find sequence convergence as the rounds proceeded. At 7th round, almost all sequences showed convergence.

A total of 14 sequences were selected from the 5, 6, 7 rounds, the binding activity to NGF was measured by the surface plasmon resonance method. The measurement method is as shown in Example 1. As a result of the measurement, all sequences significantly bound to NGF than 40N of the control. The nucleotide sequences actually obtained are shown below.

SEQ ID NO: 48:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)GGaGU(F)U(F)U(F)C(F)C(F)GU(F)C(F)U(F)C
(F)GGU(F)GGC(F)U(F)GU(F)U(F)aU(F)GU(F)GC(F)GC(F)aU(F)aC(F)aU(F)
GGaU(F)C(F)C(F)U(F)C(F)

SEQ ID NO: 49:
GGGaGaaC(F)U(F)U(F)C(F)GaC(F)C(F)aGaaGU(F)U(F)U(F)GC(F)aC(F)aU
(F)C(F)C(F)U(F)GC(F)U(F)GC(F)GU(F)aGU(F)U(F)U(F)C(F)C(F)GU(F)C(F)
U(F)aC(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 50:
GGGaGaaC(F)U(F)U(F)C(F)GaC(F)C(F)aGaaGC(F)U(F)GGC(F)aC(F)aU(F)C
(F)C(F)U(F)GU(F)U(F)GC(F)GU(F)aGU(F)U(F)U(F)C(F)C(F)GU(F)C(F)U
(F)aC(F)GU(F)GaC(F)U(F)GU(F)U(F)aU(F)GU(F)GC(F)GC(F)aU(F)aC(F)aU
(F)GGaU(F)C(F)C(F)U(F)C(F)

SEQ ID NO: 51:
GGGaGaaC(F)U(F)U(F)C(F)GaC(F)C(F)aGaaGU(F)U(F)GGC(F)aC(F)aC(F)C
(F)C(F)U(F)GC(F)U(F)aC(F)GGaGU(F)U(F)U(F)C(F)C(F)GU(F)C(F)U(F)C
(F)GGU(F)GGC(F)U(F)GU(F)U(F)aU(F)GU(F)GC(F)GC(F)aU(F)aC(F)aU(F)
GGaU(F)C(F)C(F)U(F)C(F)

SEQ ID NO: 52:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)aU(F)aGU(F)U(F)U(F)C(F)C(F)GU(F)C(F)U
(F)U(F)U(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 53:
GGGaGaaC(F)U(F)U(F)C(F)GaC(F)C(F)aGaaGU(F)U(F)U(F)GC(F)aC(F)aU
(F)C(F)C(F)U(F)GC(F)U(F)GC(F)GC(F)aGU(F)U(F)U(F)C(F)C(F)GU(F)C(F)
U(F)aC(F)GU(F)GGC(F)U(F)GU(F)U(F)aU(F)GU(F)GC(F)GC(F)aU(F)aC(F)
aU(F)GGaU(F)C(F)C(F)U(F)C(F)

SEQ ID NO: 54:
GGGaGaaC(F)U(F)U(F)C(F)GaC(F)C(F)aGaaGU(F)U(F)GGC(F)aC(F)aU(F)C
(F)C(F)U(F)GaU(F)GC(F)GU(F)aGU(F)U(F)U(F)C(F)C(F)GU(F)C(F)U(F)G
C(F)GU(F)GU(F)C(F)U(F)GU(F)U(F)aU(F)GU(F)GC(F)GC(F)aU(F)aC(F)aU
(F)GGaU(F)C(F)C(F)U(F)C(F)

SEQ ID NO: 55:
GGGaGaaC(F)U(F)U(F)C(F)GaC(F)C(F)aGaaGU(F)U(F)GGC(F)aC(F)aU(F)C
(F)C(F)U(F)GU(F)U(F)GC(F)GU(F)aGU(F)U(F)U(F)C(F)C(F)GU(F)C(F)U
(F)GC(F)GU(F)GGC(F)U(F)GU(F)U(F)aU(F)GU(F)GC(F)GC(F)aU(F)aC(F)aU
(F)GGaU(F)C(F)C(F)U(F)C(F)

SEQ ID NO: 56:
GGGaGaaC(F)U(F)U(F)C(F)GaC(F)C(F)aGaaGU(F)U(F)GC(F)aC(F)aU(F)C
(F)C(F)U(F)GC(F)U(F)GU(F)GU(F)aGU(F)U(F)U(F)C(F)C(F)GU(F)C(F)U(F)
GC(F)aU(F)GGU(F)U(F)GU(F)U(F)aU(F)GU(F)GC(F)GC(F)aU(F)aC(F)aU
(F)GGaU(F)C(F)C(F)U(F)C(F)

SEQ ID NO: 57:
GGGaGaaC(F)U(F)U(F)C(F)GaC(F)C(F)aGaaGU(F)aGGC(F)aC(F)GU(F)C(F)
C(F)U(F)GC(F)U(F)GC(F)aU(F)aGU(F)U(F)U(F)C(F)C(F)GU(F)C(F)U(F)G
U(F)GU(F)GGC(F)U(F)GU(F)U(F)aU(F)GU(F)GC(F)GC(F)aU(F)aC(F)aU(F)
GGaU(F)C(F)C(F)U(F)C(F)

SEQ ID NO: 58:
GGGaGaaC(F)U(F)U(F)C(F)GaC(F)C(F)aGaaGU(F)U(F)GaC(F)aC(F)aU(F)C
(F)C(F)U(F)GC(F)U(F)GC(F)GU(F)aGU(F)U(F)U(F)C(F)C(F)GU(F)C(F)U
(F)GC(F)GU(F)GGU(F)U(F)GU(F)U(F)aU(F)GU(F)GC(F)GC(F)aU(F)aC(F)aU
(F)GGaU(F)C(F)C(F)U(F)C(F)

SEQ ID NO: 59:
GGGaGaaC(F)U(F)U(F)C(F)GaC(F)C(F)aGaaGU(F)U(F)U(F)GC(F)aC(F)aU
(F)C(F)C(F)U(F)GC(F)U(F)GC(F)GU(F)aGU(F)U(F)U(F)C(F)C(F)U(F)U(F)
C(F)U(F)GC(F)GU(F)GGU(F)U(F)GU(F)U(F)aU(F)GU(F)GC(F)GC(F)aU(F)a
C(F)aU(F)GGaU(F)C(F)C(F)U(F)C(F)

SEQ ID NO: 60:
GGGaGaaC(F)U(F)U(F)C(F)GaC(F)C(F)aGaaGU(F)U(F)GGC(F)aC(F)aU(F)C
(F)C(F)U(F)GC(F)U(F)GC(F)aGaGU(F)U(F)U(F)C(F)C(F)GU(F)C(F)U(F)C
(F)GGU(F)GGC(F)U(F)GU(F)U(F)aU(F)GU(F)GC(F)GC(F)aU(F)aC(F)aU(F)
GGaU(F)C(F)C(F)U(F)C(F)

SEQ ID NO: 61:
GGGaGaaC(F)U(F)U(F)C(F)GaC(F)C(F)aGaaGU(F)U(F)aGC(F)aC(F)aU(F)C
(F)C(F)U(F)GC(F)U(F)GC(F)GU(F)aGU(F)U(F)U(F)C(F)C(F)GU(F)C(F)U (F)U(F)C(F)GC(F)GGU(F)U(F)GU(F)U(F)aU(F)GU(F)GC(F)GC(F)aU(F)aC(F)
aU(F)GGaU(F)C(F)C(F)U(F)C(F)

The secondary structure of these aptamers was predicted using the MFOLD program to find that all of them had a structure shown by the consensus secondary structure 1. The 5' side of all the sequences of the internal loops 1 was CCU and the 3' side was UGUU. In addition, loop 2 contained a consensus sequence shown by 5'-UUUCCXU-3'. Here, X is either G or U. The 1st, 3rd, 8th and 9th base pairs of stem 2 were G-C, U-G, a-U and G-C, respectively. The 2nd and 4th-7th contained some different base pairs.

In the same manner as in Example 4, these aptamers were subjected to shortening. As a result, in all aptamers, the chain could be shortened to a structure similar to the consensus secondary structure 1 while maintaining the binding activity.

In the same manner as in Examples 3 and 8, the neurite outgrowth inhibitory activity and TF-1 cell proliferation inhibitory activity were evaluated. As a result, these aptamers all showed a high inhibitory activity at a concentration of 10 nM. The nucleotide sequences actually obtained are shown below.

```
SEQ ID NO: 62:
GGGU(F)C(F)C(F)U(F)GC(F)U(F)GC(F)GGaGU(F)U(F)U(F)C(F)C(F)GU(F)C
(F)U(F)C(F)GGU(F)GGC(F)U(F)GU(F)U(F)aC(F)C(F)C(F)

SEQ ID NO: 63:
GGGU(F)C(F)C(F)U(F)GC(F)U(F)GC(F)GU(F)aGU(F)U(F)U(F)C(F)C(F)GU
(F)C(F)U(F)aC(F)GU(F)GGC(F)U(F)GU(F)U(F)aC(F)C(F)C(F)

SEQ ID NO: 64:
GGGU(F)C(F)C(F)U(F)GU(F)U(F)GC(F)GU(F)aGU(F)U(F)U(F)C(F)C(F)GU
(F)C(F)U(F)aC(F)GU(F)GaC(F)U(F)GU(F)U(F)aC(F)C(F)C(F)

SEQ ID NO: 65:
GGGU(F)C(F)C(F)U(F)GC(F)U(F)aC(F)GGaGU(F)U(F)U(F)C(F)C(F)GU(F)C
(F)U(F)C(F)GGU(F)GGC(F)U(F)GU(F)U(F)aC(F)C(F)C(F)

SEQ ID NO: 66:
GGGU(F)C(F)C(F)U(F)GC(F)U(F)GC(F)aU(F)aGU(F)U(F)U(F)C(F)C(F)GU
(F)C(F)U(F)U(F)U(F)GU(F)GGC(F)U(F)GU(F)U(F)aC(F)C(F)C(F)

SEQ ID NO: 67:
GGGU(F)C(F)C(F)U(F)GC(F)U(F)GC(F)GC(F)aGU(F)U(F)U(F)C(F)C(F)GU
(F)C(F)U(F)aC(F)GU(F)GGC(F)U(F)GU(F)U(F)aC(F)C(F)C(F)

SEQ ID NO: 68:
GGGU(F)C(F)C(F)U(F)GaU(F)GC(F)GU(F)aGU(F)U(F)U(F)C(F)C(F)GU(F)C
(F)U(F)GC(F)GU(F)GU(F)C(F)U(F)GU(F)U(F)aC(F)C(F)C(F)

SEQ ID NO: 69:
GGGU(F)C(F)C(F)U(F)GU(F)U(F)GC(F)GU(F)aGU(F)U(F)U(F)C(F)C(F)GU
(F)C(F)U(F)GC(F)GU(F)GGC(F)U(F)GU(F)U(F)aC(F)C(F)C(F)

SEQ ID NO: 70:
GGGU(F)C(F)C(F)U(F)GC(F)U(F)GU(F)GU(F)aGU(F)U(F)U(F)C(F)C(F)GU
(F)C(F)U(F)GC(F)aU(F)GGU(F)U(F)GU(F)U(F)aC(F)C(F)C(F)

SEQ ID NO: 71:
GGGU(F)C(F)C(F)U(F)GC(F)U(F)GC(F)aU(F)aGU(F)U(F)U(F)C(F)C(F)GU
(F)C(F)U(F)GU(F)GU(F)GGC(F)U(F)GU(F)U(F)aC(F)C(F)C(F)

SEQ ID NO: 72:
GGGU(F)C(F)C(F)U(F)GC(F)U(F)GC(F)GU(F)aGU(F)U(F)U(F)C(F)C(F)GU
(F)C(F)U(F)GC(F)GU(F)GGU(F)U(F)GU(F)U(F)aC(F)C(F)C(F)

SEQ ID NO: 73:
GGGU(F)C(F)C(F)U(F)GC(F)U(F)GC(F)GU(F)aGU(F)U(F)U(F)C(F)C(F)U(F)
U(F)C(F)U(F)GC(F)GU(F)GGU(F)U(F)GU(F)U(F)aC(F)C(F)C(F)

SEQ ID NO: 74:
GGGU(F)C(F)C(F)U(F)GC(F)U(F)GC(F)aGaGU(F)U(F)U(F)C(F)C(F)GU(F)C
(F)U(F)C(F)GGU(F)GGC(F)U(F)GU(F)U(F)aC(F)C(F)C(F)

SEQ ID NO: 75:
GGGU(F)C(F)C(F)U(F)GC(F)U(F)GC(F)GU(F)aGU(F)U(F)U(F)C(F)C(F)GU
(F)C(F)U(F)U(F)C(F)GC(F)GGU(F)U(F)GU(F)U(F)aC(F)C(F)C(F)
```

Example 11

Production of NGF Aptamer—5

Using the following template wherein stem 2 in the consensus secondary structure 1 is randomized, SELEX was performed in the same manner as in Example 1.

```
template 4:
                                        (SEQ ID NO: 147)
5'-
gaggatccatgtatgcgcacataacagnnnnnnnngacggaaacnnnnnn
ncaggatgtgccaacttctggtcgaagttctccc-3'
```

After the completion of 7 rounds, the sequences of 48 clones were confirmed, but sequence convergence was not seen. Thus, 3 more rounds were performed. After the completion of 10 m rounds, the sequences of 48 clones were confirmed to find convergence in about half the sequences. The remaining half sequences were single sequences. 17 sequences were selected therefrom, and the binding activity to NGF was measured by the surface plasmon resonance method. The measurement method is as shown in Example 1. As a result of the measurement, it was found that all sequences more significantly bind to NGF than 40N of the control.

In the same manner as in Example 4, the above-mentioned aptamers were subjected to shortening. As a result, in all aptamers, the chain could be shortened to a structure similar to the consensus secondary structure 1 while maintaining the binding activity. The nucleotide sequences actually obtained are shown below.

```
SEQ ID NO: 76:
GGGU(F)C(F)C(F)U(F)GaU(F)U(F)aaGaGU(F)U(F)U(F)C(F)C(F)GU(F)C(F)
U(F)C(F)GU(F)aaU(F)C(F)U(F)GU(F)U(F)aC(F)C(F)C(F)

SEQ ID NO: 77:
GGGU(F)C(F)C(F)U(F)GaC(F)U(F)aaGaGU(F)U(F)U(F)C(F)C(F)GU(F)C(F)
U(F)C(F)GU(F)aGU(F)C(F)U(F)GU(F)U(F)aC(F)C(F)C(F)

SEQ ID NO: 78:
GGGU(F)C(F)C(F)U(F)GGC(F)C(F)aaGaGU(F)U(F)U(F)C(F)C(F)GU(F)C(F)
U(F)C(F)GU(F)GGU(F)C(F)U(F)GU(F)U(F)aC(F)C(F)C(F)

SEQ ID NO: 79:
GGGU(F)C(F)C(F)U(F)GGU(F)U(F)aaGaGU(F)U(F)U(F)C(F)C(F)GU(F)C(F)
U(F)C(F)GU(F)aaC(F)C(F)U(F)GU(F)U(F)aC(F)C(F)C(F)

SEQ ID NO: 80:
GGGU(F)C(F)C(F)U(F)GGC(F)U(F)aaGaGU(F)U(F)U(F)C(F)C(F)GU(F)C(F)
U(F)C(F)GU(F)aGU(F)C(F)U(F)GU(F)U(F)aC(F)C(F)C(F)

SEQ ID NO: 81:
GGGU(F)C(F)C(F)U(F)GGU(F)GaU(F)aaGU(F)U(F)U(F)C(F)C(F)GU(F)C(F)
U(F)U(F)aU(F)C(F)aC(F)C(F)U(F)GU(F)U(F)aC(F)C(F)C(F)

SEQ ID NO: 82:
GGGU(F)C(F)C(F)U(F)GGaU(F)aaGaGU(F)U(F)U(F)C(F)C(F)GU(F)C(F)U(F)
C(F)GU(F)aU(F)C(F)C(F)U(F)GU(F)U(F)aC(F)C(F)C(F)

SEQ ID NO: 83:
GGGU(F)C(F)C(F)U(F)GU(F)aC(F)aaGaGU(F)U(F)U(F)C(F)C(F)GU(F)C(F)
U(F)C(F)GU(F)GU(F)aC(F)U(F)GU(F)U(F)aC(F)C(F)C(F)

SEQ ID NO: 84:
GGGU(F)C(F)C(F)U(F)GU(F)C(F)GC(F)U(F)aaGU(F)U(F)U(F)C(F)C(F)GU
(F)C(F)U(F)U(F)U(F)GC(F)GGC(F)U(F)GU(F)U(F)aC(F)C(F)C(F)

SEQ ID NO: 85:
GGGU(F)C(F)C(F)U(F)GaGU(F)aaGaGU(F)U(F)U(F)C(F)C(F)GU(F)C(F)U(F)
C(F)aU(F)aC(F)U(F)C(F)U(F)GU(F)U(F)aC(F)C(F)C(F)

SEQ ID NO: 86:
GGGU(F)C(F)C(F)U(F)GC(F)U(F)GC(F)GU(F)aGU(F)U(F)U(F)C(F)C(F)U(F)
U(F)C(F)U(F)GC(F)GU(F)GGU(F)U(F)GU(F)U(F)aC(F)C(F)C(F)

SEQ ID NO: 87:
GGGU(F)C(F)C(F)U(F)GC(F)U(F)C(F)aaGaGU(F)U(F)U(F)C(F)C(F)GU(F)C
(F)U(F)C(F)GU(F)GGGC(F)U(F)GU(F)U(F)aC(F)C(F)C(F)

SEQ ID NO: 88:
GGGU(F)C(F)C(F)U(F)GU(F)U(F)C(F)aaGaGU(F)U(F)U(F)C(F)C(F)GU(F)C
(F)U(F)C(F)GU(F)GaaC(F)U(F)GU(F)U(F)aC(F)C(F)C(F)

SEQ ID NO: 89:
GGGU(F)C(F)C(F)U(F)GU(F)GGaaGaGU(F)U(F)U(F)C(F)C(F)GU(F)C(F)U(F)
C(F)GU(F)C(F)C(F)aC(F)U(F)GU(F)U(F)aC(F)C(F)C(F)
```

-continued

SEQ ID NO: 90:
GGGU(F)C(F)C(F)U(F)GC(F)GU(F)aaGaGU(F)U(F)U(F)C(F)C(F)GU(F)C(F)
U(F)C(F)GU(F)aU(F)GC(F)U(F)GU(F)U(F)aC(F)C(F)C(F)

SEQ ID NO: 91:
GGGU(F)C(F)C(F)U(F)GC(F)C(F)U(F)aaGaGU(F)U(F)U(F)C(F)C(F)GU(F)C
(F)U(F)C(F)GU(F)aGGC(F)U(F)GU(F)U(F)aC(F)C(F)C(F)

SEQ ID NO: 92:
GGGU(F)C(F)C(F)U(F)GaC(F)C(F)aaGaGU(F)U(F)U(F)C(F)C(F)GU(F)C(F)
U(F)C(F)GU(F)GGU(F)C(F)U(F)GU(F)aC(F)C(F)C(F)

With the neurite length per cell obtained by the addition of NGF alone as inhibitory activity 0%, and that of the cell obtained by NGF free culture for 2 days as inhibitory activity 100%, the neurite outgrowth inhibitory activities of these aptamers were calculated from the neurite length per cell obtained by culturing with the addition of NGF and the aptamer in mixture. The 50% inhibitory concentration ($IC_{50}$) was determined from the concentrations at two, above and below points sandwiching the 50% inhibitory activity. The experiment results are shown in Table 1. In Table 1, the $IC_{50}$ value indicated as "<X" means that the inhibitory activity was not less than 50% when the indicated concentration X was minimum measured concentration. All tested aptamers showed a strong inhibitory activity. The $IC_{50}$ values thereof are partly shown in Table 1.

As regards the TF-1 cell proliferation inhibitory activity, using the amount of luminescence per well obtained by the addition of NGF alone and culture of the cells for 3 days as inhibitory activity 0%, and that of the well obtained by NGF free culture for 3 days as inhibitory activity 100%, the inhibitory activity of the aptamer was calculated from the amount of luminescence per well obtained by culturing with the addition of NGF and the aptamer in mixture. The 50% inhibitory concentration ($IC_{50}$) was determined from the concentrations at two, above and below points sandwiching the 50% inhibitory activity. The results are shown in Table 1. $IC_{50}$ value indicated as "<X" means that the inhibitory activity was not less than 50% when the indicated concentration X was minimum measured concentration. As a result of the experiment, the $IC_{50}$ value of the aptamers other than SEQ ID NOs: 81, 84, 86, 89 was found to be not more than 1 nM.

The 5' side of all sequences of the internal loops 1 in these aptamers was CCU and the 3' side was UGUU. In addition, loop 2 contained a consensus sequence shown by 5'-UUUC-CXU-3'. Here, X is either G or U. The final base pair of stem 1 was always U-a. The 1st, 8th and 9th base pairs of stem 2 were G-C, a-U and G-C, respectively. The 2nd-7th contained some different base pairs.

Example 12

Production of NGF Aptamer—6

To produce an aptamer that inhibits NGF but does not inhibit NT-3 and NT-4, new SELEX was performed. As a first pool, RNA pools used first in Examples 9 and 10 were mixed at 1:1 and used. The RNA pool before selection was mixed with NT-3 (manufactured by R&D Systems, 294 pmol), NT-4 (manufactured by R&D Systems, 179 pmol) and BDNF (manufactured by R&D Systems, 148 pmol), and the mixture was added to beads with NGF (380 pmol) immobilized thereon.

After the completion of 4 rounds, the sequences of 48 clones were confirmed to find no sequence convergence. Some single sequences had the same sequences as SEQ ID NOs: 27, 28, 34, 64, 72. Novel 14 sequences were selected and the secondary structure was predicted using the MFOLD program to find that all contained the consensus secondary structure 1. Thus, these aptamers were subjected to shortening to 40 mer in the same manner as with the consensus secondary structure 1. The binding activity of these shortened forms to NGF and NT-3 was measured by the surface plasmon resonance method. For the measurement method, BIAcore2000 manufactured by BIAcore was used and CM5 reactive with amino group was used as a sensorchip, as shown in Example 1. The protein was immobilized in the same manner as in Example 1 by using ethyl-3-carbodiimide hydrochloride and N-hydroxysuccinimide. Human NGF or NT-3 was dissolved in an immobilization solution (10 mM sodium acetate, pH 6) and used at 25-40 µg/ml. After protein immobilization, blocking with ethanolamine-HCl was performed. The amount of immobilized NGF and NT-3 was 3,000-4,000 RU and 3,000-5,000 RU, respectively. The aptamer for an analyte was prepared to 0.15 µM-0.5 µM. The running buffer and regeneration solution were the same as those in Example 1. NT-3 was immobilized on FC2, and NGF on FC3, and the final sensorgram was obtained by subtracting the results of FC1. Consequently, 7 sequences were found to strongly bind to NGF. On the other hand, almost no sequences bound to NT-3.

In the same manner as in Example 3, the neurite outgrowth inhibitory activity was measured to find that the aptamer shown by SEQ ID NO: 93-98 showed a strong inhibitory activity at 10 nM. The nucleotide sequences actually obtained, which correspond to each SEQ ID NO, are shown below.

SEQ ID NO: 93:
GGGU(F)C(F)C(F)U(F)GC(F)C(F)GC(F)GU(F)aGU(F)U(F)
U(F)C(F)C(F)GU(F)C(F)U(F)U(F)C(F)GC(F)GGU(F)U(F)
GU(F)U(F)aC(F)C(F)C(F)

SEQ ID NO: 94:
GGGU(F)C(F)C(F)U(F)GC(F)U(F)GC(F)GU(F)aGU(F)U(F)
U(F)C(F)C(F)GU(F)C(F)U(F)GC(F)GGaGC(F)U(F)GU(F)U
(F)aC(F)C(F)C(F)

SEQ ID NO: 95:
GGGU(F)C(F)C(F)U(F)GC(F)U(F)GC(F)GU(F)aGU(F)U(F)
U(F)C(F)C(F)aU(F)C(F)U(F)U(F)C(F)GU(F)GGC(F)U(F)
GU(F)U(F)aC(F)C(F)C(F)

SEQ ID NO: 96:
GGGU(F)C(F)C(F)U(F)GC(F)U(F)GC(F)GU(F)aGU(F)U(F)
U(F)C(F)C(F)GU(F)C(F)U(F)aU(F)GU(F)GGC(F)U(F)GU
(F)U(F)aC(F)C(F)C(F)

SEQ ID NO: 97:
GGGU(F)C(F)C(F)U(F)GC(F)U(F)aC(F)GU(F)aGU(F)U(F)
U(F)C(F)C(F)GU(F)C(F)U(F)GC(F)GU(F)GGC(F)U(F)GU
(F)U(F)aC(F)C(F)C(F)

-continued

SEQ ID NO: 98:
GGGU(F)C(F)C(F)U(F)GC(F)U(F)aC(F)GU(F)aGU(F)U(F)
U(F)C(F)C(F)GU(F)C(F)U(F)aC(F)GU(F)GGC(F)U(F)GU
(F)U(F)aC(F)C(F)C(F)

The 5' side of all sequences of the internal loops 1 in these aptamers was CCU and the 3' side was UGUU. In addition, loop 2 contained a consensus sequence shown by 5'-UUUC-CXU-3'. Here, X is either G or a. The final base pair of stem 1 was always U-a. The 2nd, 5th, 8th and 9th base pairs of stem 2 were C-G, C-G, a-U and G-C, respectively. There were some different base pairs in the others.

SELEX was performed up to 7 rounds and the sequences of 48 clones were confirmed to find that most sequences converge one kind of sequence. 13 single sequences were selected from the rest, and the binding activity to NGF and NT-3 was examined by the surface plasmon resonance method and in the same manner as above. Consequently, 7 sequences were found to strongly bind to NGF. On the other hand, almost no sequences bound to NT-3.

The secondary structure of these aptamers was predicted using the MFOLD program to find that all did not have the consensus secondary structure 1. In the same manner as in Example 3, the neurite outgrowth inhibitory activity was measured to find that the aptamers shown by SEQ ID NOs: 99 and 100 showed a strong inhibitory activity at 10 nM. On the other hand, the TF-1 cell proliferation inhibitory activity was measured in the same manner as in Example 8 to find no inhibitory activity. The nucleotide sequences actually obtained, which correspond to each SEQ ID NO, are shown below.

SEQ ID NO: 99:
GGGaGaaC(F)U(F)U(F)C(F)GaC(F)C(F)aGaaGU(F)C(F)C
(F)aaaC(F)GGGaC(F)U(F)U(F)U(F)aU(F)aC(F)C(F)U(F)C
(F)U(F)GaGU(F)C(F)GC(F)C(F)U(F)U(F)U(F)GC(F)U(F)C
(F)C(F)U(F)aU(F)GU(F)GC(F)GC(F)aU(F)aC(F)aU(F)GG
aU(F)C(F)C(F)U(F)C(F)

SEQ ID NO: 100:
GGGaGaaC(F)U(F)U(F)C(F)GaC(F)C(F)aGaaGaC(F)C(F)
aaaC(F)GGaC(F)U(F)U(F)U(F)aU(F)aC(F)C(F)U(F)C(F)U
(F)GaGU(F)C(F)GC(F)C(F)U(F)aU(F)GC(F)U(F)C(F)C(F)
U(F)aU(F)GU(F)GC(F)GC(F)aU(F)aC(F)aU(F)GGaU(F)C
(F)C(F)U(F)C(F)

Example 13

Production of NGF Aptamer—7

New SELEX was performed in the same manner as in Example 12 to produce an aptamer that inhibits NGF but does not inhibit NT-3 and NT-4. The template and primer first used for RNA pool are as described below.

template 5:
(SEQ ID NO: 148)
5'-
gaggatccatgtatgcgcacatnnnnggatacgagnnnnnnnctctta
tccnnnatgtgccaacttctggtcgaagttctccc-3'

In the sequence, the underlined base sequence is as described below.
a: a(70%), g(10%), c(10%), t(10%)
g: a(10%), g(70%), c(10%), t(10%)
c: a(10%), g(10%), c(70%), t(10%)
t: a(10%), g(10%), c(10%), t(70%)

primer Fwd3:
(SEQ ID NO: 149)
5'-taatacgactcactatagggagaacttcgaccagaagttggcaca primer Rev3:
(SEQ ID NO: 150)
5'-gaggatccatgtatgcgcaca The template sequence was based on the sequence shown by SEQ ID NO: 82, stem 2 of the consensus secondary structure 1 was doped with 30% of random sequence, and internal loop 1 and loop 2 sections were completely randomized (n).

After the completion of 4 rounds, the sequences of 48 clones were confirmed to find that 21 clones were identical with the sequence shown by SEQ ID NO: 22. Of the remaining sequences, 2 clones were the same, and others were single sequences. 13 sequences were selected therefrom and the secondary structure was predicted using the MFOLD program to find they had the consensus secondary structure 1. Then, the aptamers were subjected to shortening to 40 mer in the same manner as with consensus secondary structure 1. The binding activity of the shortened aptamers was confirmed by the surface plasmon resonance method in the same manner as in Example 12. NT-4 was measured in the same manner as in NT-3. As a result, it was found that the shortened forms strongly bind to NGF. On the other hand, the binding to NT-3 and NT-4 was weak.

In the same manner as in Example 3, the neurite outgrowth inhibitory activity of these shortened forms was measured to find that the aptamers shown by SEQ ID NOs: 101 and 102 showed a strong inhibitory activity as evidenced by an $IC_{50}$ value of 1 nM or below (Table 1). On the other hand, the TF-1 cell proliferation inhibitory activity was measured in the same manner as in Example 8 to find that the $IC_{50}$ value of the same two aptamers was not less than 1 nM. The nucleotide sequences actually obtained, which correspond to each SEQ ID NO, are shown below.

SEQ ID NO: 101:
GGGU(F)C(F)C(F)U(F)GaC(F)GU(F)aU(F)aGU(F)U(F)
U(F)C(F)C(F)GU(F)C(F)U(F)GU(F)aU(F)GU(F)C(F)U
(F)GU(F)U(F)aC(F)C(F)C(F)

SEQ ID NO: 102:
GGGU(F)C(F)C(F)U(F)GaGC(F)aaGaGU(F)U(F)U(F)C
(F)C(F)GU(F)C(F)U(F)C(F)aU(F)GC(F)U(F)C(F)U(F)GU
(F)U(F)aC(F)C(F)C(F)

Example 14

Sequence Analysis Using High-Speed Sequencer

To obtain an aptamer having consensus secondary structure 1, which inhibits NGF but does not inhibit other neurotrophins, sequences were analyzed using high-speed sequencer GS FLX (manufactured by Roche). While sequence analysis of 48 clones was performed by Sanger sequencing in Example 1, use of a high-speed sequencer enables analyses of tens of thousands of sequences. The measurement and data analysis were performed in Operon, and sample preparation was performed according to the protocol of Operon. The measurement target DNA was an equimolar mixture of DNA pools after the completion of 7, 9 and 10 rounds obtained by SELEX in Example 8, 4 and 5 rounds obtained by SELEX in Example 12, and 3 and 4 rounds obtained by SELEX in Example 13.

The total number of the obtained sequences was 69249. Among them, 40077 sequences contained a completely identical FLX primer sequence or a FLX primer sequence wherein one base is substituted, and a partial sequence of N40 with a length of 40. The secondary structure of these sequences was predicted using the RNAfold program to find 22453 sequences containing the same structure as the consensus secondary structure 1. When compared to the sequences obtained in Examples 10, 12, 13 by Sanger sequencing, 99% were novel sequences. Among the novel sequences, 1615 kinds of sequences contained convergence, and 4168 sequences were single sequences. Novel 52 sequences that emerged highly frequently were selected therefrom, and subjected to shortening to 40 mer to afford the shape of consensus secondary structure 1. In addition, 10 single sequences obtained in Example 13 by Sanger sequencing were picked up again, and subjected to shortening to 40 mer in the same manner.

The shortened sequences were measured for the binding to NGF, NT-3, NT-4 by the surface plasmon resonance method. The measurement was performed in the same manner as in Example 13. As a result, all sequences bound to NGF, and particularly, the following 15 sequences showed strong binding. On the other hand, they were scarcely bound to NT-3 and NT-4.

Therefore, the neurite outgrowth inhibitory activity of the 15 sequences was measured by a method similar to that in Example 3. As a result, it was found that all aptamers had an $IC_{50}$ value of not more than 1 nM (Table 1). In addition, the TF-1 cell proliferation inhibitory activity was measured by a method similar to that in Example 8 to find that the aptamers shown by SEQ ID NOs: 111, 112, 114-117 had an $IC_{50}$ value of not more than 1 nM (Table 1).

The nucleotide sequences actually obtained, which correspond to each SEQ ID NO, are shown below. SEQ ID NO: 111 is the sequence obtained in Example 13 by Sanger sequencing.

```
SEQ ID NO: 103:
GGGU(F)C(F)C(F)U(F)GC(F)U(F)GC(F)GU(F)aGU(F)U(F)U(F)C(F)C(F)GU
(F)C(F)U(F)GC(F)GU(F)GGU(F)U(F)GU(F)U(F)aC(F)C(F)C(F)

SEQ ID NO: 104:
GGGU(F)C(F)C(F)U(F)GaU(F)GU(F)C(F)aaGU(F)U(F)U(F)C(F)C(F)GU(F)C
(F)U(F)U(F)GaU(F)GU(F)C(F)U(F)GU(F)U(F)aC(F)C(F)C(F)

SEQ ID NO: 105:
GGGU(F)C(F)C(F)U(F)GU(F)U(F)GC(F)U(F)aaGU(F)U(F)U(F)C(F)C(F)GU
(F)C(F)U(F)U(F)aGU(F)GaC(F)U(F)GU(F)U(F)aC(F)C(F)C(F)

SEQ ID NO: 106:
GGGU(F)C(F)C(F)U(F)GC(F)U(F)GC(F)GU(F)aGU(F)U(F)U(F)C(F)C(F)GU
(F)C(F)U(F)GC(F)GU(F)aGC(F)U(F)GU(F)U(F)aC(F)C(F)C(F)

SEQ ID NO: 107:
GGGU(F)C(F)C(F)U(F)GC(F)U(F)GC(F)GaaGU(F)U(F)U(F)C(F)C(F)GU(F)C
(F)U(F)U(F)C(F)GU(F)GGC(F)U(F)GU(F)U(F)aC(F)C(F)C(F)

SEQ ID NO: 108:
GGGU(F)C(F)C(F)U(F)GU(F)U(F)GC(F)GU(F)aGU(F)U(F)U(F)C(F)C(F)GU
(F)C(F)U(F)GC(F)GU(F)GaC(F)U(F)GU(F)U(F)aC(F)C(F)C(F)

SEQ ID NO: 109:
GGGU(F)C(F)C(F)U(F)GC(F)U(F)GC(F)GU(F)aGU(F)U(F)U(F)C(F)C(F)U(F)
U(F)C(F)U(F)GC(F)GU(F)GGC(F)U(F)GU(F)U(F)aC(F)C(F)C(F)

SEQ ID NO: 110:
GGGU(F)C(F)C(F)U(F)GC(F)C(F)GC(F)GU(F)aGU(F)U(F)U(F)C(F)C(F)GU
(F)C(F)U(F)GC(F)GU(F)GGC(F)U(F)GU(F)U(F)aC(F)C(F)C(F)

SEQ ID NO: 111:
GGGU(F)C(F)C(F)U(F)GU(F)C(F)U(F)aaGaGU(F)U(F)U(F)C(F)C(F)GU(F)C
(F)U(F)C(F)GU(F)aGaC(F)U(F)GU(F)U(F)aC(F)C(F)C(F)

SEQ ID NO: 112:
GGGU(F)C(F)C(F)U(F)GU(F)U(F)C(F)aaGaGU(F)U(F)U(F)C(F)C(F)GU(F)C
(F)U(F)C(F)GU(F)GGaC(F)U(F)GU(F)U(F)aC(F)C(F)C(F)

SEQ ID NO: 113:
GGGU(F)C(F)C(F)U(F)GC(F)U(F)GU(F)GU(F)aGU(F)U(F)U(F)C(F)C(F)GU
(F)C(F)U(F)GC(F)aU(F)GGU(F)U(F)GU(F)U(F)aC(F)C(F)C(F)

SEQ ID NO: 114:
GGGU(F)C(F)C(F)U(F)GaC(F)aaaGaGU(F)U(F)U(F)C(F)C(F)GU(F)C(F)U(F)
C(F)GU(F)U(F)GU(F)C(F)U(F)GU(F)U(F)aC(F)C(F)C(F)

SEQ ID NO: 115:
GGGU(F)C(F)C(F)U(F)GU(F)C(F)U(F)aaGaGU(F)U(F)U(F)C(F)C(F)GU(F)C
(F)U(F)C(F)GU(F)aGaC(F)U(F)GU(F)U(F)aC(F)C(F)C(F)

SEQ ID NO: 116:
GGGU(F)C(F)C(F)U(F)GU(F)C(F)U(F)aaGaGU(F)U(F)U(F)C(F)C(F)GU(F)C
(F)U(F)C(F)GU(F)GaaC(F)U(F)GU(F)U(F)aC(F)C(F)C(F)
```

```
SEQ ID NO: 117:
GGGU(F)C(F)C(F)U(F)GU(F)U(F)GaaGaGU(F)U(F)U(F)C(F)C(F)GU(F)C(F)
U(F)C(F)GU(F)C(F)aaC(F)U(F)GU(F)U(F)aC(F)C(F)C(F)
```

The 5' side of all the sequences of the internal loops 1 in these aptamers was CCU and the 3' side was UGUU. In addition, loop 2 contained a consensus sequence shown by 5'-UUUCCXU-3'. Here, X is either G or U. The final base pair of stem 1 was always U-a. The 8th and 9th base pairs of stem 2 were a-U and G-C, respectively. The 1st to 7th contained some different base pairs.

Example 15

Modification of Shortened Aptamers

To enhance the stability of the aptamer in blood, variants wherein the modification at the 2'-position of ribose has been replaced were prepared.

The sequences of the modified forms are shown below. The parentheses in the nucleotides show the 2'-position modification, F is fluorine atom, M is o-methyl group, and L is Locked Nucleic Acid (LNA). The upper-case letter shows RNA, the lower-case letter shows DNA, and idT means inverted dT. The linker used for the 5' end was ssH Linker (SAFC) or DMS (O)MT-AMINO-MODIFIER C6 (GLEN RESEARCH), and the linker used for the 3' end was TFA Amino C-6 lcaa CPG (ChemGenes). PEG40GS2 is 2-branched GS type having a molecular weight of 40000 (SUNBRIGHT GL2-400GS2 manufactured by NOF CORPORATION), PEG40TS2 is 2-branched TS type having a molecular weight of 40000 (SUNBRIGHT GL2-400TS manufactured by NOF CORPORATION), PEG40TS4 is 4-branched TS type having a molecular weight of 40000 (SUNBRIGHT GL4-400TS manufactured by NOF CORPORATION), PEG80TS2 is 2-branched TS type having a molecular weight of 80000 (SUNBRIGHT GL2-800TS manufactured by NOF CORPORATION), and PEG80TS4 is 4-branched TS type having a molecular weight of 80000 (SUNBRIGHT GL4-800TS manufactured by NOF CORPORATION).

```
SEQ ID NO: 38 (1):
idT-
G(M)G(M)G(M)U(F)C(F)C(F)U(F)GC(F)U(F)G(M)C(F)G(M)U(F)aG(M)U(F)U
(F)U(F)C(F)C(F)G(M)U(F)C(F)U(F)U(F)C(F)G(M)C(F)G(M)G(M)C(F)U(F)
GU(F)U(F)aC(F)C(F)C(F)-idT

SEQ ID NO: 151:
idT-
G(M)G(M)G(M)U(F)C(F)C(F)U(F)GC(F)U(F)G(M)C(F)G(M)U(F)aG(M)U(F)U
(F)U(F)C(F)C(F)G(M)U(F)C(F)U(F)GC(F)G(M)U(F)G(M)G(M)C(F)U(F)GU
(F)U(F)aC(F)C(F)C(F)-idT

SEQ ID NO: 152:
idT-
G(M)G(M)G(M)U(F)C(F)C(F)U(F)GC(F)U(F)G(M)C(F)G(M)U(F)aG(M)U(F)U
(F)U(F)C(F)C(F)G(M)U(F)C(F)U(F)G(M)C(F)G(M)U(F)G(M)G(M)C(F)U(F)
GU(F)U(F)aC(F)C(F)C(F)-idT

SEQ ID NO: 153:
PEG40GS2-
G(M)G(M)G(M)U(F)C(F)C(F)U(F)GC(F)U(F)G(M)C(F)G(M)U(F)aG(M)U(F)U
(F)U(F)C(F)C(F)G(M)U(F)C(F)U(F)G(M)C(F)G(M)U(F)G(M)G(M)C(F)U(F)
GU(F)U(F)aC(F)C(F)C(F)-idT

SEQ ID NO: 154:
idT-
G(M)G(M)G(M)U(F)C(F)C(F)U(F)GC(F)U(F)G(M)C(F)G(M)U(F)aG(M)U(F)U
(F)U(F)C(F)C(F)G(M)U(F)C(F)U(F)G(M)C(F)G(M)U(F)G(M)G(M)C(F)U(F)
GU(F)U(F)aC(F)C(F)C(F)-PEG40GS2

SEQ ID NO: 155:
idT-
G(M)G(M)G(M)U(F)C(F)C(F)U(F)GC(F)U(F)G(M)C(F)G(M)C(F)aG(M)U(F)U
(F)U(F)C(F)C(F)G(M)U(F)C(F)U(F)aC(F)G(M)U(F)G(M)G(M)C(F)U(F)GU
(F)U(F)aC(F)C(F)C(F)-idT

SEQ ID NO: 62(1):
idT-
G(M)G(M)G(M)U(F)C(F)C(F)U(F)GC(F)U(F)G(M)C(F)G(M)G(M)aG(M)U(F)U
(F)U(F)C(F)C(F)G(M)U(F)C(F)U(F)C(F)G(M)G(M)U(F)G(M)G(M)C(F)U(F)
GU(F)U(F)aC(F)C(F)C(F)-idT

SEQ ID NO: 66(1):
idT-
G(M)G(M)G(M)U(F)C(F)C(F)U(F)GC(F)U(F)G(M)C(F)aU(F)aG(M)U(F)U(F)
U(F)C(F)C(F)G(M)U(F)C(F)U(F)U(F)U(F)G(M)U(F)G(M)G(M)C(F)U(F)GU
(F)U(F)aC(F)C(F)C(F)-idT
```

-continued

SEQ ID NO: 68(1):
idT-
G(M)G(M)G(M)U(F)C(F)C(F)U(F)GaU(F)G(M)C(F)G(M)U(F)aG(M)U(F)U(F)
U(F)C(F)C(F)G(M)U(F)C(F)U(F)G(M)C(F)G(M)U(F)G(M)U(F)C(F)U(F)GU
(F)U(F)aC(F)C(F)C(F)-idT

SEQ ID NO: 71(1):
idT-
G(M)G(M)G(M)U(F)C(F)C(F)U(F)GC(F)U(F)G(M)C(F)aU(F)aG(M)U(F)U(F)
U(F)C(F)C(F)G(M)U(F)C(F)U(F)G(M)U(F)G(M)U(F)G(M)G(M)C(F)U(F)GU
(F)U(F)aC(F)C(F)C(F)-idT

SEQ ID NO: 74(1):
idT-
G(M)G(M)G(M)U(F)C(F)C(F)U(F)GC(F)U(F)G(M)C(F)aG(M)aG(M)U(F)U(F)
U(F)C(F)C(F)G(M)U(F)C(F)U(F)C(F)G(M)G(M)U(F)G(M)G(M)C(F)U(F)GU
(F)U(F)aC(F)C(F)C(F)-idT

SEQ ID NO: 76(1):
idT-
G(M)G(M)G(M)U(F)C(F)C(F)U(F)GaU(F)U(F)aaG(M)aG(M)U(F)U(F)U(F)C
(F)C(F)G(M)U(F)C(F)U(F)C(F)G(M)U(F)aaU(F)C(F)U(F)GU(F)U(F)aC(F)C
(F)C(F)-idT

SEQ ID NO: 77(1):
idT-
G(M)G(M)G(M)U(F)C(F)C(F)U(F)GaC(F)U(F)aaG(M)aG(M)U(F)U(F)U(F)C
(F)C(F)G(M)U(F)C(F)U(F)C(F)G(M)U(F)aG(M)U(F)C(F)U(F)GU(F)U(F)aC
(F)C(F)C(F)-idT

SEQ ID NO: 78(1):
idT-
G(M)G(M)G(M)U(F)C(F)C(F)U(F)GG(M)C(F)C(F)aaG(M)aG(M)U(F)U(F)U(F)
C(F)C(F)G(M)U(F)C(F)U(F)C(F)G(M)U(F)G(M)G(M)U(F)C(F)U(F)GU(F)U
(F)aC(F)C(F)C(F)-idT

SEQ ID NO: 78(2):
idT-
G(M)G(M)G(M)U(M)C(F)C(M)U(F)GG(M)C(F)C(F)aaG(M)aG(M)U(F)U(F)U(F)
C(F)C(M)G(M)U(M)C(F)U(F)C(M)G(M)U(M)G(M)G(M)U(M)C(M)U(F)GU(M)U
(F)aC(M)C(M)C(M)-idT

SEQ ID NO: 78(3):
idT-
G(M)G(M)G(M)U(M)C(F)C(M)U(F)GG(M)C(M)C(M)aaG(M)aG(M)U(F)U(F)U(F)
C(F)C(M)G(M)U(M)C(F)U(F)C(M)G(M)U(M)G(M)G(M)U(F)C(M)U(F)GU(M)U
(F)aC(M)C(M)C(M)-idT

SEQ ID NO: 76(4):
idT-
G(M)G(M)G(M)U(M)C(F)C(M)U(F)GG(M)C(M)C(M)aaG(M)aG(M)U(F)U(F)U(F)
C(F)C(M)G(M)U(M)C(F)U(F)C(M)G(M)U(M)G(M)G(M)U(M)C(M)U(F)GU(M)U
(F)aC(M)C(M)C(M)-idT

SEQ ID NO: 79(1):
idT-
G(M)G(M)G(M)U(F)C(F)C(F)U(F)GG(M)U(F)U(F)aaG(M)aG(M)U(F)U(F)U(F)
C(F)C(F)G(M)U(F)C(F)U(F)C(F)G(M)U(F)aaC(F)C(F)U(F)GU(F)U(F)aC
(F)C(F)C(F)-idT

SEQ ID NO: 80(1):
idT-
G(M)G(M)G(M)U(F)C(F)C(F)U(F)GG(M)C(F)U(F)aaG(M)aG(M)U(F)U(F)U(F)
C(F)C(F)G(M)U(F)C(F)U(F)C(F)G(M)U(F)aG(M)U(F)C(F)U(F)GU(F)U(F)
aC(F)C(F)C(F)-idT

SEQ ID NO: 82(1):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(F)C(F)C(F)-idT

SEQ ID NO: 82(2):
idT-
G(M)G(M)G(M)U(M)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(F)C(F)C(F)-idT

-continued

SEQ ID NO: 82(3):
idT-
G(M)G(M)G(M)U(F)C(F)C(M)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(F)C(F)C(F)-idT

SEQ ID NO: 82(4):
idT-
G(M)G(M)G(M)U(F)C(F)C(F)U(F)GG(M)aU(M)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(F)C(F)C(F)-idT

SEQ ID NO: 82(5):
idT-
G(M)G(M)G(M)U(F)C(F)C(F)U(F)GG(M)aU(F)aaG(M)aG(M)U(F)U(F)U(F)C
(M)C(F)G(M)U(F)C(F)U(F)C(F)G(M)U(F)aU(F)C(F)C(F)U(F)GU(F)U(F)aC
(F)C(F)C(F)-idT

SEQ ID NO: 82(6):
idT-
G(M)G(M)G(M)U(F)C(F)C(F)U(F)GG(M)aU(F)aaG(M)aG(M)U(F)U(F)U(F)C
(F)C(M)G(M)U(F)C(F)U(F)C(F)G(M)U(F)aU(F)C(F)C(F)U(F)GU(F)U(F)aC
(F)C(F)C(F)-idT

SEQ ID NO: 82(7):
idT-
G(M)G(M)G(M)U(F)C(F)C(F)U(F)GG(M)aU(F)aaG(M)aG(M)U(F)U(F)U(F)C
(F)C(F)G(M)U(M)C(F)U(F)C(F)G(M)U(F)aU(F)C(F)C(F)U(F)GU(F)U(F)aC
(F)C(F)C(F)-idT

SEQ ID NO: 82(8):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(M)C(F)G(M)U(F)aU(F)C(F)C(F)U(F)GU(F)U(F)aC
(F)C(F)C(F)-idT

SEQ ID NO: 82(9):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(M)G(M)U(F)aU(F)C(F)C(F)U(F)GU(F)U(F)aC
(F)C(F)C(F)-idT

SEQ ID NO: 82(10):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(M)aU(F)C(F)C(F)U(F)GU(F)U(F)aC
(F)C(F)C(F)-idT

SEQ ID NO: 82(11):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(M)C(F)C(F)U(F)GU(F)U(F)aC
(F)C(F)C(F)-idT

SEQ ID NO: 82(12):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(M)C(F)U(F)GU(F)U(F)aC
(F)C(F)C(F)-idT

SEQ ID NO: 82(13):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(M)U(F)GU(F)U(F)aC
(F)C(F)C(F)-idT

SEQ ID NO: 82(14):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(M)GU(F)U(F)aC
(F)C(F)C(F)-idT

SEQ ID NO: 82(15):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(M)U(F)aC
(F)C(F)C(F)-idT

SEQ ID NO: 82(16):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(M)C(F)C(F)-idT

SEQ ID NO: 82(17):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(F)C(M)C(F)-idT

SEQ ID NO: 82(18):
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)U(F)aC
(F)C(F)C(M)-idT

SEQ ID NO: 82(19):
idT-
G(M)G(M)G(M)U(M)C(F)C(M)U(F)GG(M)aU(M)aaG(M)aG(M)U(F)U(F)U(F)C
(M)C(F)G(M)U(F)C(F)U(F)C(M)G(M)U(M)aU(M)C(M)C(M)U(F)GU(M)U(F)aC
(M)C(M)C(M)-idT

SEQ ID NO: 82(20):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(F)aU(M)C(F)C(M)U(F)GU(M)U(F)aC
(M)C(M)C(M)-idT

SEQ ID NO: 82(21):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(F)G(M)U(M)aU(M)C(F)C(M)U(F)GU(M)U(F)aC
(M)C(M)C(M)-idT

SEQ ID NO: 82(22):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(F)C(M)U(F)GU(M)U(F)aC
(M)C(M)C(M)-idT

SEQ ID NO: 82(23):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(F)aU(M)C(M)C(M)U(F)GU(M)U(F)aC
(M)C(M)C(M)-idT

SEQ ID NO: 82(24):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(F)G(M)U(M)aU(M)C(M)C(M)U(F)GU(M)U(F)aC
(M)C(M)C(M)-idT

SEQ ID NO: 82(25):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(M)C(M)U(F)GU(M)U(F)aC
(M)C(M)C(M)-idT

SEQ ID NO: 82(26):
idT-
G(M)G(M)G(M)U(M)C(F)C(M)U(F)GG(M)aU(M)aaG(M)aG(M)U(F)U(F)U(F)C
(M)C(M)G(M)U(M)C(F)U(F)C(M)G(M)U(M)aU(M)C(M)C(M)U(F)GU(M)U(F)aC
(M)C(M)C(M)-idT

SEQ ID NO: 82(27):
idT-
G(M)G(M)G(M)U(F)cC(F)U(F)GG(M)aU(F)aaG(M)aG(M)U(F)U(F)U(F)C(F)C
(F)G(M)U(F)C(F)U(F)C(F)G(M)U(F)aU(F)C(F)C(F)U(F)GU(F)U(F)aC(F)C
(F)C(F)-idT

SEQ ID NO: 156:
idT-
G(M)G(M)G(M)U(F)C(F)C(F)U(F)GG(M)aU(F)aaG(M)aG(M)tU(F)U(F)C(F)C
(F)G(M)U(F)C(F)U(F)C(F)G(M)U(F)aU(F)C(F)C(F)U(F)GU(F)U(F)aC(F)C
(F)C(F)-idT

-continued

SEQ ID NO: 157:
idT-
G(M)G(M)G(M)U(F)C(F)C(F)U(F)GG(M)aU(F)aaG(M)aG(M)U(F)tU(F)C(F)C
(F)G(M)U(F)C(F)U(F)C(F)G(M)U(F)aU(F)C(F)C(F)U(F)GU(F)U(F)aC(F)C
(F)C(F)-idT

SEQ ID NO: 82(30):
idT-
G(M)G(M)G(M)U(F)C(F)C(F)U(F)GG(M)aU(F)aaG(M)aG(M)U(F)U(F)U(F)cC
(F)G(M)U(F)C(F)U(F)C(F)G(M)U(F)aU(F)C(F)C(F)U(F)GU(F)U(F)aC(F)C
(F)C(F)-idT

SEQ ID NO: 82(31):
idT-
G(M)G(M)G(M)U(F)C(F)C(F)U(F)GG(M)aU(F)aaG(M)aG(M)U(F)U(F)U(F)C
(F)C(F)G(M)U(F)cU(F)C(F)G(M)U(F)aU(F)C(F)C(F)U(F)GU(F)U(F)aC(F)C
(F)C(F)-idT

SEQ ID NO: 158:
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)tGU(F)U(F)aC(F)C
(F)C(F)-idT

SEQ ID NO: 159:
idT-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)C(F)U(F)GU(F)taC(F)C
(F)C(F)-idT

SEQ ID NO: 160:
idT-
G(M)G(M)G(M)U(M)C(F)C(M)U(F)GG(M)aU(M)aaG(M)aG(M)tU(F)U(F)C(F)C
(M)G(M)U(M)C(F)U(F)C(M)G(M)U(M)aU(M)C(M)C(M)U(F)GU(M)U(F)aC(M)C
(M)C(M)-idT

SEQ ID NO: 161:
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(M)C(M)tGU(M)U(F)aC(M)C
(M)C(M)-idT

SEQ ID NO: 162:
idT-
G(M)G(M)G(M)U(M)C(F)C(M)U(F)GG(M)aU(M)aaG(M)aG(M)tU(F)U(F)C(F)C
(M)G(M)U(M)C(F)U(F)C(M)G(M)U(M)aU(M)C(M)C(M)tGU(M)U(F)aC(M)C(M)
C(M)-idT

SEQ ID NO: 82(37):
idT-
G(M)G(M)G(M)U(M)C(F)C(M)uGG(M)aU(M)aaG(M)aG(M)U(F)U(F)U(F)C(F)C
(M)G(M)U(M)C(F)U(F)C(M)G(M)U(M)aU(M)C(M)C(M)U(F)GU(M)U(F)aC(M)C
(M)C(M)-idT

SEQ ID NO: 82(38):
idT-
G(M)G(M)G(M)U(M)C(F)C(M)U(F)GG(M)aU(M)aaG(M)aG(M)U(F)uU(F)C(F)C
(M)G(M)U(M)C(F)U(F)C(M)G(M)U(M)aU(M)C(M)C(M)U(F)GU(M)U(F)aC(M)C
(M)C(M)-idT

SEQ ID NO: 82(39):
idT-
G(M)G(M)G(M)U(M)C(F)C(M)U(F)GG(M)aU(M)aaG(M)aG(M)U(F)U(F)uC(F)C
(M)G(M)U(M)C(F)U(F)C(M)G(M)U(M)aU(M)C(M)C(M)U(F)GU(M)U(F)aC(M)C
(M)C(M)-idT

SEQ ID NO: 82(40):
idT-
G(M)G(M)G(M)U(M)C(F)C(M)U(F)GG(M)aU(M)aaG(M)aG(M)U(F)U(F)U(F)C
(F)C(M)G(M)U(M)C(F)uC(M)G(M)U(M)aU(M)C(M)C(M)U(F)GU(M)U(F)aC(M)C
(M)C(M)-idT

SEQ ID NO: 82(41):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(M)C(M)U(F)GU(M)uaC(M)C
(M)C(M)-idT

-continued

SEQ ID NO: 82(42):
idT-
G(M)G(M)G(M)U(M)C(F)C(M)U(F)GG(M)aU(M)aaG(M)A(M)G(M)U(F)U(F)
C(F)C(M)G(M)U(M)C(F)U(F)C(M)G(M)U(M)aU(M)C(M)C(M)U(F)GU(M)U(F)
aC(M)C(M)C(M)-idT

SEQ ID NO: 82(43):
idT-
G(M)G(M)G(M)U(M)C(F)C(M)U(F)GG(M)aU(M)aA(M)G(M)aG(M)U(F)U(F)
C(F)C(M)G(M)U(M)C(F)U(F)C(M)G(M)U(M)aU(M)C(M)C(M)U(F)GU(M)U(F)
aC(M)C(M)C(M)-idT

SEQ ID NO: 82(44):
idT-
G(M)G(M)G(M)U(M)C(F)C(M)U(F)GG(M)aU(M)A(M)aG(M)aG(M)U(F)U(F)
C(F)C(M)G(M)U(M)C(F)U(F)C(M)G(M)U(M)aU(M)C(M)C(M)U(F)GU(M)U(F)
aC(M)C(M)C(M)-idT

SEQ ID NO: 82(45):
idT-
G(M)G(M)G(M)U(M)C(F)C(M)U(F)GG(M)A(M)U(M)aaG(M)aG(M)U(F)U(F)
C(F)C(M)G(M)U(M)C(F)U(F)C(M)G(M)U(M)aU(M)C(M)C(M)U(F)GU(M)U(F)
aC(M)C(M)C(M)-idT

SEQ ID NO: 82(46):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)A(M)U(M)C(M)C(M)U(F)GU(M)U(F)
aC(M)C(M)C(M)-idT

SEQ ID NO: 82(47):
idT-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(M)C(M)U(F)GU(M)U(F)A(M)
C(M)C(M)C(M)-idT

SEQ ID NO: 82(48):
idT-
G(M)G(M)G(M)U(M)C(F)C(M)U(F)GG(M)A(M)U(M)aaG(M)A(M)G(M)U(F)U(F)
U(F)C(F)C(M)G(M)U(M)C(F)U(F)C(M)G(M)U(M)A(M)U(M)C(M)C(M)U(F)GU
(M)U(F)A(M)C(M)C(M)C(M)-idT

SEQ ID NO: 163:
idT-
G(M)G(M)G(M)U(M)C(F)C(M)U(F)GG(M)aU(M)aaG(M)aG(M)tU(F)U(F)C(F)C
(M)G(M)U(M)C(F)U(F)C(M)G(M)U(M)aU(M)C(M)C(M)tGU(M)uaC(M)C(M)C(M)-
idT

SEQ ID NO: 164:
idT-
G(M)G(M)G(M)U(M)C(F)C(M)uGG(M)aU(M)aaG(M)aG(M)tU(F)U(F)C(F)C(M)
G(M)U(M)C(F)U(F)C(M)G(M)U(M)aU(M)C(M)C(M)tGU(M)U(F)aC(M)C(M)C(M)-
idT

SEQ ID NO: 165:
idT-
G(M)G(M)G(M)U(M)C(F)C(M)U(F)GG(M)aU(M)aaG(M)aG(M)tU(F)U(F)C(F)C
(M)G(M)U(M)C(F)U(F)C(M)G(M)U(M)aU(M)C(M)C(M)tGU(M)uA(M)C(M)C(M)
C(M)-idT

SEQ ID NO: 166:
idT-
G(M)G(M)G(M)U(M)C(F)C(M)U(F)GG(M)A(M)U(M)aaG(M)A(M)G(M)tU(F)U(F)
C(F)C(M)G(M)U(M)C(F)U(F)C(M)G(M)U(M)A(M)U(M)C(M)C(M)tGU(M)uA(M)
C(M)C(M)C(M)-idT

SEQ ID NO: 167:
idT-
G(M)G(M)G(M)U(M)C(F)C(M)U(F)GG(M)A(M)U(M)aaG(M)A(M)G(M)tU(F)U(F)
C(F)C(M)G(M)U(M)C(F)U(F)C(M)G(M)U(M)A(M)U(M)C(M)C(M)tGU(M)U(F)
A(M)C(M)C(M)C(M)-idT

SEQ ID NO: 168:
idT-
G(M)G(M)G(M)U(M)C(F)C(M)U(F)uGG(M)A(M)U(M)aaG(M)A(M)G(M)tU(F)U(F)C
(F)C(M)G(M)U(M)C(F)U(F)C(M)G(M)U(M)A(M)U(M)C(M)C(M)tGU(M)uA(M)C
(M)C(M)C(M)-idT

-continued

SEQ ID NO: 82(55):
PEG80TS4-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(M)C(M)U(F)GU(M)U(F)aC
(M)C(M)C(M)-idT

SEQ ID NO: 82(56):
PEG40GS2-
G(M)G(M)G(M)U(F)C(F)C(F)U(F)GG(M)aU(F)aaG(M)aG(M)U(F)U(F)U(F)C
(F)C(F)G(M)U(F)C(F)U(F)C(F)G(M)U(F)aU(F)C(F)U(F)GU(F)U(F)aC
(F)C(F)C(F)-idT

SEQ ID NO: 82(57):
G(M)G(M)G(M)U(M)C(F)C(M)U(F)sGG(M)A(M)U(M)aaG(M)A(M)G(M)U(F)U(F)
U(F)C(F)C(M)G(M)U(M)C(F)U(F)C(M)G(M)U(M)A(M)U(M)C(M)C(M)U(F)GU
(M)U(F)A(M)C(M)C(M)C(M)-idT

SEQ ID NO: 82(58):
G(M)G(M)G(M)U(M)C(F)C(M)U(F)GsG(M)A(M)U(M)aaG(M)A(M)G(M)U(F)U(F)
U(F)C(F)C(M)G(M)U(M)C(F)U(F)C(M)G(M)U(M)A(M)U(M)C(M)C(M)U(F)GU
(M)U(F)A(M)C(M)C(M)C(M)-idT

SEQ ID NO: 82(59):
G(M)G(M)G(M)U(M)C(F)C(M)U(F)GG(M)A(M)U(M)saaG(M)A(M)G(M)U(F)U(F)
U(F)C(F)C(M)G(M)U(M)C(F)U(F)C(M)G(M)U(M)A(M)U(M)C(M)C(M)U(F)GU
(M)U(F)A(M)C(M)C(M)C(M)-idT SEQ ID NO: 82(60):
G(M)G(M)G(M)U(M)C(F)C(M)U(F)GG(M)A(M)U(M)asaG(M)A(M)G(M)U(F)U(F)
U(F)C(F)C(M)G(M)U(M)C(F)U(F)C(M)G(M)U(M)A(M)U(M)C(M)C(M)U(F)GU
(M)U(F)A(M)C(M)C(M)C(M)-idT SEQ ID NO: 82(61):
G(M)G(M)G(M)U(M)C(F)C(M)U(F)GG(M)A(M)U(M)aasG(M)A(M)G(M)U(F)U(F)
U(F)C(F)C(M)G(M)U(M)C(F)U(F)C(M)G(M)U(M)A(M)U(M)C(M)C(M)U(F)GU
(M)U(F)A(M)C(M)C(M)C(M)-idT SEQ ID NO: 82(62):
G(M)G(M)G(M)U(M)C(F)C(M)U(F)GG(M)A(M)U(M)aaG(M)A(M)G(M)U(F)U(F)
U(F)C(F)C(M)G(M)U(M)C(F)U(F)C(M)G(M)U(M)A(M)U(M)C(M)C(M)U(F)sGU
(M)U(F)A(M)C(M)C(M)C(M)-idT SEQ ID NO: 82(63):
G(M)G(M)G(M)U(M)C(F)C(M)U(F)GG(M)A(M)U(M)aaG(M)A(M)G(M)U(F)U(F)
U(F)C(F)C(M)G(M)U(M)C(F)U(F)C(M)G(M)U(M)A(M)U(M)C(M)C(M)U(F)GsU
(M)U(F)A(M)C(M)C(M)C(M)-idT SEQ ID NO: 82(64):
PEG40TS2-
G(M)G(M)G(M)U(M)C(F)C(M)U(F)GG(M)aU(M)aaG(M)aG(M)U(F)U(F)U(F)C
(F)C(M)G(M)U(M)C(F)U(F)C(M)G(M)U(M)aU(M)C(M)C(M)U(F)GU(M)U(F)aC
(M)C(M)C(M)-idT SEQ ID NO: 87(1):
idT-
G(M)G(M)G(M)U(F)C(F)C(F)U(F)GC(F)U(F)C(F)aaGaGU(F)U(F)U(F)C(F)C
(F)GU(F)C(F)U(F)C(F)GU(F)GGGC(F)U(F)GU(F)U(F)aC(M)C(M)C(M)-idT SEQ ID NO: 87(2):
idT-
G(M)G(M)G(M)U(M)C(F)C(M)U(F)GC(F)U(F)C(F)aaG(M)aG(M)U(F)U(F)U(F)
C(F)C(M)G(M)U(M)C(F)U(F)C(M)G(M)U(M)GGGC(M)U(F)GU(M)U(F)aC(M)C
(M)C(M)-idT SEQ ID NO: 87(3):
idT-
G(M)G(M)G(M)U(M)C(F)C(M)U(F)GC(F)U(F)C(F)aaG(M)aG(M)U(F)U(F)U(F)
C(F)C(M)G(M)U(M)C(F)U(F)C(M)G(M)U(M)G(M)G(M)G(M)C(M)U(F)GU(M)U
(F)aC(M)C(M)C(M)-idT SEQ ID NO: 87(4):
idT-
G(M)G(M)G(M)U(M)C(F)C(M)U(F)GC(F)U(M)C(M)aaG(M)aG(M)U(F)U(F)U(F)
C(F)C(M)G(M)U(M)C(F)U(F)C(M)G(M)U(M)G(M)G(M)G(M)C(M)U(F)GU(M)U
(F)aC(M)C(M)C(M)-idT SEQ ID NO: 87(5):
G(M)G(M)G(M)U(M)C(F)C(M)U(F)GC(M)U(M)C(M)aaG(M)A(M)G(M)U(F)U(F)
U(F)C(F)C(M)G(M)U(M)C(F)U(F)C(M)G(M)U(M)G(M)G(M)G(M)C(M)U(F)GU
(M)U(F)A(M)C(M)C(M)C(M)-idT -continued

```
SEQ ID NO: 88(1):
idT-
GGGU(F)C(F)C(F)U(F)GU(F)U(F)C(F)aaGaGU(F)U(F)U(F)C(F)C(F)GU(F)C
(F)U(F)C(F)GU(F)GaaC(F)U(F)GU(F)U(F)aC(M)C(M)C(M)-idT

SEQ ID NO: 88(2):
idT-
G(M)G(M)G(M)U(F)C(F)C(F)U(F)GU(F)U(F)C(F)aaGaGU(F)U(F)U(F)C(F)C
(F)GU(F)C(F)U(F)C(F)GU(F)GaaC(F)U(F)GU(F)U(F)aC(M)C(M)C(M)-idT

SEQ ID NO: 88(3):
idT-
G(M)G(M)G(M)U(M)C(F)C(M)U(F)GU(F)U(F)C(F)aaG(M)aG(M)U(F)U(F)U(F)
C(F)C(M)G(M)U(M)C(F)U(F)C(M)G(M)U(M)GaaC(M)U(F)GU(M)U(F)aC(M)C
(M)C(M)-idT

SEQ ID NO: 88(4):
idT-
G(M)G(M)G(M)U(M)C(F)C(M)U(F)GU(M)U(M)C(M)aaG(M)aG(M)U(F)U(F)U(F)
C(F)C(M)G(M)U(M)C(F)U(F)C(M)G(M)U(M)G(M)aaC(M)U(F)GU(M)U(F)aC
(M)C(M)C(M)-idT

SEQ ID NO: 89(1):
idT-
G(M)G(M)G(M)U(F)C(F)C(F)U(F)GU(F)GGaaGaGU(F)U(F)U(F)C(F)C(F)GU
(F)C(F)U(F)C(F)GU(F)C(F)C(F)aC(F)U(F)GU(F)U(F)aC(M)C(M)C(M)-idT

SEQ ID NO: 89(2):
idT-
G(M)G(M)G(M)U(F)C(F)C(M)U(F)GU(F)GGaaG(M)aG(M)U(F)U(F)U(F)C(F)C
(M)G(M)U(M)C(F)U(F)C(M)G(M)U(M)C(F)C(F)aC(M)U(F)GU(M)U(F)aC(M)C
(M)C(M)-idT
SEQ ID NO: 89(3):
idT-
G(M)G(M)G(M)U(F)C(F)C(M)U(F)GU(F)G(M)G(M)aaG(M)aG(M)U(F)U(F)U(F)
C(F)C(M)G(M)U(M)C(F)U(F)C(M)G(M)U(M)C(F)C(F)aC(M)U(F)GU(M)U(F)
aC(M)C(M)C(M)-idT

SEQ ID NO: 89(4):
idT-
G(M)G(M)G(M)U(F)C(F)C(M)U(F)GU(M)G(M)G(M)aaG(M)aG(M)U(F)U(F)U(F)
C(F)C(M)G(M)U(M)C(F)U(F)C(M)G(M)U(M)C(M)C(M)aC(M)U(F)GU(M)U(F)
aC(M)C(M)C(M)-idT

SEQ ID NO: 89(5):
G(M)G(M)G(M)U(M)C(F)C(M)U(F)GU(M)G(M)G(M)aaG(M)A(M)G(M)U(F)U(F)
U(F)C(F)C(M)G(M)U(M)C(F)U(F)C(M)G(M)U(M)C(M)C(M)A(M)C(M)U(F)GU
(M)U(F)A(M)C(M)C(M)C(M)-idT

SEQ ID NO: 111(1):
G(M)G(M)G(M)U(M)C(F)C(M)U(F)GU(M)C(M)U(M)aaG(M)A(M)G(M)U(F)U(F)
U(F)C(F)C(M)G(M)U(M)C(F)U(F)C(M)G(M)U(M)A(M)G(M)A(M)C(M)U(F)GU
(M)U(F)A(M)C(M)C(M)C(M)-idT
```

The binding activity of RNA shown by SEQ ID NO: 82(2) to NGF, NT-3, NT-4 was measured by the surface plasmon resonance method in the same manner as in Example 13. As a result, the RNA was found to have a binding activity to any protein (FIG. 3). In addition, whether the aptamer shown by SEQ ID NO: 82(2) inhibits the binding of NGF and its receptor (TrkA or p75) was examined in the same manner as in Example 2 by the surface plasmon resonance method. As a result, it was found that the aptamer strongly inhibits the binding of NGF and the both receptors (FIGS. 4 and 5).

The neurite outgrowth inhibitory activity of all of the above-mentioned modified forms was measured by a method similar to that in Example 3. As a result, the $IC_{50}$ value of all modified forms other than SEQ ID NO: 62(1) was not more than 1 nM (Table 1). Particularly, the $IC_{50}$ value of the aptamer shown by SEQ ID NO: 162 was 0.033 nM. Moreover, the TF-1 cell proliferation inhibitory activity was measured by a method similar to that in Example 8 to find that almost all aptamers had an $IC_{50}$ value of not more than 1 nM (Table 1). Particularly, the $IC_{50}$ value of the aptamer shown by SEQ ID NO: is 162 was 0.014 nM. The $IC_{50}$ value of the aptamer shown by SEQ ID NO: 62(1) was 0.49 nM.

From the above, it was shown that the aptamers can maintain the inhibitory activity even when the modification at the 2'-position of ribose is changed.

TABLE 1

| | base | neurite outgrowth inhibition $IC_{50}$ | cell proliferation inhibition $IC_{50}$ |
|---|---|---|---|
| SEQ ID NO: 76 | 40 | <0.3 | <0.3 |
| SEQ ID NO: 77 | 40 | <0.3 | <0.3 |
| SEQ ID NO: 78 | 40 | <0.3 | <0.3 |
| SEQ ID NO: 79 | 40 | <0.3 | <0.3 |
| SEQ ID NO: 80 | 40 | <0.3 | <0.3 |
| SEQ ID NO: 81 | 40 | 0.765 | 6.924 |
| SEQ ID NO: 82 | 40 | <0.3 | <0.3 |
| SEQ ID NO: 83 | 40 | <0.3 | <0.3 |
| SEQ ID NO: 84 | 40 | 0.793 | >10 |
| SEQ ID NO: 85 | 40 | <0.3 | 0.311 |

TABLE 1-continued

| base | neurite outgrowth inhibition IC$_{50}$ | cell proliferation inhibition IC$_{50}$ |
|---|---|---|
| SEQ ID NO: 86 | 40 | 0.834 | >10 |
| SEQ ID NO: 88 | 40 | 0.572 | 0.979 |
| SEQ ID NO: 89 | 40 | 0.959 | >1 |
| SEQ ID NO: 76(1) | 40 | 0.117 | 0.013 |
| SEQ ID NO: 77(1) | 40 | 0.126 | 0.013 |
| SEQ ID NO: 78(1) | 40 | 0.12 | 0.018 |
| SEQ ID NO: 79(1) | 40 | 0.289 | <0.03 |
| SEQ ID NO: 80(1) | 40 | 0.271 | 0.03 |
| SEQ ID NO: 82(1) | 40 | 0.7 | 0.012 |
| SEQ ID NO: 87(1) | 40 | 0.173 | <0.1 |
| SEQ ID NO: 87(2) | 40 | 0.107 | <0.1 |
| SEQ ID NO: 87(3) | 40 | 0.118 | <0.1 |
| SEQ ID NO: 87(4) | 40 | 0.113 | <0.1 |
| SEQ ID NO: 87(5) | 40 | 0.078 | 0.178 |
| SEQ ID NO: 88(1) | 40 | 0.241 | <0.1 |
| SEQ ID NO: 88(2) | 40 | 0.241 | <0.1 |
| SEQ ID NO: 88(3) | 40 | 0.106 | <0.1 |
| SEQ ID NO: 88(4) | 40 | 0.111 | <0.1 |
| SEQ ID NO: 89(1) | 40 | 0.246 | <0.1 |
| SEQ ID NO: 89(2) | 40 | 0.103 | <0.1 |
| SEQ ID NO: 89(3) | 40 | 0.122 | <0.1 |
| SEQ ID NO: 89(4) | 40 | <0.1 | <0.1 |
| SEQ ID NO: 89(5) | 40 | 0.079 | >0.3 |
| SEQ ID NO: 82(2) | 40 | 0.145 | 0.041 |
| SEQ ID NO: 82(3) | 40 | 0.255 | 0.051 |
| SEQ ID NO: 82(4) | 40 | 0.139 | 0.036 |
| SEQ ID NO: 82(5) | 40 | 0.269 | 0.075 |
| SEQ ID NO: 82(6) | 40 | 0.128 | 0.034 |
| SEQ ID NO: 82(7) | 40 | 0.143 | 0.030 |
| SEQ ID NO: 82(8) | 40 | 0.284 | 0.071 |
| SEQ ID NO: 82(9) | 40 | 0.252 | 0.035 |
| SEQ ID NO: 82(10) | 40 | 0.128 | 0.033 |
| SEQ ID NO: 82(11) | 40 | 0.253 | 0.046 |
| SEQ ID NO: 82(12) | 40 | 0.127 | 0.027 |
| SEQ ID NO: 82(13) | 40 | 0.146 | 0.034 |
| SEQ ID NO: 82(14) | 40 | 0.294 | >0.1 |
| SEQ ID NO: 82(15) | 40 | 0.127 | 0.043 |
| SEQ ID NO: 82(16) | 40 | 0.129 | 0.026 |
| SEQ ID NO: 82(17) | 40 | 0.127 | 0.025 |
| SEQ ID NO: 82(18) | 40 | 0.244 | 0.028 |
| SEQ ID NO: 82(19) | 40 | 0.291 | >0.1 |
| SEQ ID NO: 82(20) | 40 | 0.244 | 0.031 |
| SEQ ID NO: 82(21) | 40 | <0.1 | 0.085 |
| SEQ ID NO: 82(22) | 40 | <0.1 | 0.083 |
| SEQ ID NO: 82(23) | 40 | <0.1 | 0.084 |
| SEQ ID NO: 82(24) | 40 | <0.1 | 0.084 |
| SEQ ID NO: 82(25) | 40 | <0.1 | 0.085 |
| SEQ ID NO: 82(26) | 40 | 0.13 | 0.087 |
| SEQ ID NO: 82(27) | 40 | 0.25 | 0.093 |
| SEQ ID NO: 156 | 40 | <0.1 | 0.085 |
| SEQ ID NO: 157 | 40 | 0.299 | >0.1 |
| SEQ ID NO: 82(30) | 40 | 0.244 | >0.1 |
| SEQ ID NO: 82(31) | 40 | 0.276 | >0.1 |
| SEQ ID NO: 158 | 40 | 0.1 | <0.03 |
| SEQ ID NO: 159 | 40 | 0.264 | >0.1 |
| SEQ ID NO: 160 | 40 | 0.038 | 0.016 |
| SEQ ID NO: 161 | 40 | 0.036 | 0.015 |
| SEQ ID NO: 162 | 40 | 0.033 | 0.014 |
| SEQ ID NO: 82(37) | 40 | 0.098 | 0.097 |
| SEQ ID NO: 82(38) | 40 | 0.295 | >0.1 |
| SEQ ID NO: 82(39) | 40 | 0.256 | >0.1 |
| SEQ ID NO: 82(40) | 40 | 0.239 | 0.073 |
| SEQ ID NO: 82(41) | 40 | 0.084 | 0.042 |
| SEQ ID NO: 82(42) | 40 | 0.037 | 0.021 |
| SEQ ID NO: 82(43) | 40 | 0.088 | >0.1 |
| SEQ ID NO: 82(44) | 40 | 0.097 | >0.1 |
| SEQ ID NO: 82(45) | 40 | 0.037 | 0.024 |
| SEQ ID NO: 82(46) | 40 | 0.033 | 0.022 |
| SEQ ID NO: 82(47) | 40 | 0.046 | 0.022 |
| SEQ ID NO: 78(2) | 40 | 0.045 | 0.016 |
| SEQ ID NO: 78(3) | 40 | 0.045 | 0.015 |
| SEQ ID NO: 78(4) | 40 | 0.037 | 0.021 |
| SEQ ID NO: 82(48) | 40 | 0.252 | 0.056 |
| SEQ ID NO: 163 | 40 | 0.113 | 0.047 |
| SEQ ID NO: 164 | 40 | 0.132 | 0.048 |
| SEQ ID NO: 165 | 40 | 0.139 | 0.039 |
| SEQ ID NO: 166 | 40 | 0.113 | 0.037 |
| SEQ ID NO: 167 | 40 | 0.128 | 0.037 |
| SEQ ID NO: 168 | 40 | 0.261 | >0.1 |
| SEQ ID NO: 82(55) | 40 | 0.101 | 0.039 |
| SEQ ID NO: 82(56) | 40 | 0.067 | 0.023 |
| SEQ ID NO: 82(57) | 40 | 0.045 | >0.3 |
| SEQ ID NO: 82(58) | 40 | 0.072 | >0.3 |
| SEQ ID NO: 82(59) | 40 | 0.034 | >0.3 |
| SEQ ID NO: 82(60) | 40 | 0.034 | 0.081 |
| SEQ ID NO: 82(61) | 40 | 0.031 | >0.3 |
| SEQ ID NO: 82(62) | 40 | 0.039 | >0.3 |
| SEQ ID NO: 82(63) | 40 | 0.046 | 0.266 |
| SEQ ID NO: 82(64) | 40 | 0.107 | 0.036 |
| SEQ ID NO: 111(1) | 40 | 0.060 | >0.3 |
| SEQ ID NO: 101 | 40 | 0.994 | >1 |
| SEQ ID NO: 102 | 40 | 0.908 | >1 |
| SEQ ID NO: 103 | 40 | 0.766 | >1 |
| SEQ ID NO: 104 | 40 | 0.682 | >1 |
| SEQ ID NO: 105 | 40 | 0.444 | >1 |
| SEQ ID NO: 106 | 40 | 0.770 | >1 |
| SEQ ID NO: 107 | 40 | 0.967 | >1 |
| SEQ ID NO: 108 | 40 | 0.403 | >1 |
| SEQ ID NO: 109 | 40 | 0.687 | >1 |
| SEQ ID NO: 110 | 40 | 0.999 | >1 |
| SEQ ID NO: 111 | 40 | 0.252 | 0.363 |
| SEQ ID NO: 112 | 40 | 0.334 | 0.193 |
| SEQ ID NO: 113 | 40 | 0.960 | >1 |
| SEQ ID NO: 114 | 40 | 0.363 | 0.296 |
| SEQ ID NO: 115 | 40 | 0.298 | 0.183 |
| SEQ ID NO: 116 | 40 | 0.411 | 0.322 |
| SEQ ID NO: 117 | 40 | 0.394 | 0.455 |

Example 16

Confirmation of Cross-Reactivity with Other Neurotrophins by a TF-1 Cell Proliferation Inhibition Assay Using TF-1 cells, whether NGF aptamer inhibits BDNF, NT-3, NT-4 was examined. Human receptor genes (TrkB, TrkC, p75) for respective neurotrophic factors were introduced into TF-1 cells (ATCC Number: CRL-2003), which is a human erythroleukemic cell line, by using a retrovirus vector to give cells that highly express these receptors stably. TF-1 cells introduced with TrkB and p75 were used for the evaluation of inhibitory activity against BDNF, TF-1 cells introduced with TrkC and p75 were used for the evaluation against NT-3, and TF-1 cells introduced with TrkB alone were used for the evaluation against NT-4. These cells were suspended in an RPMI-1640 medium containing 20% fetal bovine serum, and seeded in a white 96 well flat-bottom plate at 1000 cells (50 μL) per well. Thereto was added a mixed solution 50 μL of human BDNF (final concentration 0.074 nM) or NT-3 (final concentration 0.074 nM) or NT-4 (final concentration 0.071 nM) and the aptamer (final concentration 1 μM-0.01 nM), which had been pre-reacted at room temperature for 30 min in a serum-free RPMI-1640 medium, 3 days later, 100 μL of CellTiter-Glo reagent for CellTiter-Glo Luminescent Cell Viability Assay (manufactured by Promega) was added to each well, chemiluminescence was measured by a microplate reader. With the amount of luminescence per well obtained by the addition of BDNF or NT-3 or NT-4 alone and culture of the cells for 3 days as inhibitory activity 0%, and that of the well obtained by culture for 3 days without addition of BDNF or NT-3 or NT-4 as inhibitory activity 100%, the inhibitory activity of the aptamer was calculated from the amount of luminescence per well obtained by culturing with the addition of BDNF or NT-3 or NT-4 and the aptamer in mixture. When the inhibitory activity was 0 or below, '0%' is indicated. The 50% inhibitory concentration ($IC_{50}$) was determined from the concentrations at two, above and below points sandwiching the 50% inhibitory activity. The experiment results are shown in Table 2. An $IC_{50}$ value indicated as ">X" means that the inhibitory activity was not more than 50% when the indicated concentration X was the maximum measured concentration. N.D. means not measured.

All the tested aptamers showed a strong inhibitory activity. The $IC_{50}$ values thereof are partly shown in Table 2. As the inhibitory activity of the aptamers of the present invention described in Table 2, the $IC_{50}$ value to NGF was not more than 0.1 nM, whereas that to BDNF was not less than 1000 nM. The $IC_{50}$ value to NT-3 varied from 0.97 nM to not less than 10 nM depending on the aptamer. The $IC_{50}$ value to NT-4 varied from not more than 3 nM to not less than 30 nM depending on the aptamer.

TABLE 2

Inhibitory activity of NGF aptamer against other neurotrophin

| aptamer | BDNF ($IC_{50}$) | NT3 ($IC_{50}$) | NT4 ($IC_{50}$) | NGF ($IC_{50}$) |
| --- | --- | --- | --- | --- |
| SEQ ID NO: 78(4) | N.D. | 3 | <100 | 0.021 |
| SEQ ID NO: 82(2) | N.D. | 40.60 | <3 | 0.041 |
| SEQ ID NO: 82(3) | N.D. | 42.05 | 9.36 | 0.051 |
| SEQ ID NO: 82(4) | N.D. | 30.39 | 3.37 | 0.036 |
| SEQ ID NO: 82(5) | N.D. | 51.23 | <3 | 0.075 |
| SEQ ID NO: 82(6) | N.D. | <30 | <3 | 0.034 |
| SEQ ID NO: 82(7) | N.D. | <30 | 3.74 | 0.030 |
| SEQ ID NO: 82(9) | N.D. | 34.80 | <3 | 0.035 |
| SEQ ID NO: 82(10) | N.D. | 35.32 | <3 | 0.034 |
| SEQ ID NO: 82(11) | N.D. | 38.07 | 3.42 | 0.046 |
| SEQ ID NO: 82(12) | N.D. | 34.72 | <3 | 0.027 |
| SEQ ID NO: 82(13) | N.D. | 48.79 | 3.06 | 0.034 |
| SEQ ID NO: 82(15) | >1000 | <30 | 8.35 | 0.043 |
| SEQ ID NO: 82(16) | >1000 | 34.35 | <3 | 0.026 |
| SEQ ID NO: 82(17) | >1000 | <30 | <3 | 0.025 |
| SEQ ID NO: 82(18) | >1000 | 38.70 | <3 | 0.028 |
| SEQ ID NO: 82(20) | >1000 | <30 | >30 | 0.031 |
| SEQ ID NO: 82(21) | >1000 | <30 | >30 | 0.085 |
| SEQ ID NO: 82(22) | >1000 | <30 | >30 | 0.083 |
| SEQ ID NO: 82(23) | >1000 | <30 | >30 | 0.084 |
| SEQ ID NO: 82(24) | >1000 | <30 | >30 | 0.084 |
| SEQ ID NO: 82(25) | >1000 | 2.15 | 40.40 | 0.085 |
| SEQ ID NO: 82(26) | >1000 | <30 | >30 | 0.087 |
| SEQ ID NO: 156 | >1000 | <30 | <3 | 0.085 |
| SEQ ID NO: 158 | >1000 | <30 | <3 | <0.03 |
| SEQ ID NO: 82(55) | >1000 | 0.97 | 14.34 | 0.039 |
| SEQ ID NO: 82(1) | N.D. | >10 | <100 | <0.1 |
| SEQ ID NO: 87(1) | N.D. | >10 | <100 | <0.1 |
| SEQ ID NO: 87(4) | N.D. | >10 | >300 | <0.1 |
| SEQ ID NO: 88(1) | N.D. | >10 | <100 | <0.1 |
| SEQ ID NO: 88(4) | N.D. | >10 | 300 | <0.1 |
| SEQ ID NO: 89(4) | N.D. | >10 | 271 | <0.1 |

N.D. means not measured.

Example 17

Analgesic Action by NGF Aptamer

To study the analgesic action of NGF aptamer on NGF-induced pain, a thermal hyperalgesia model induced by subcutaneous administration of NGF to rat hind paw was used. For the experiment, Jcl:SD rats (6-week-old) were used. As an index of thermal hyperalgesia, response latency of escape behavior to infrared irradiation from a plantar heat stimulation measuring apparatus (manufactured by Ugo Basile) to the planta was used. On the previous day of the test, acclimation to the evaluation system was performed. Before administration on the day of the test, escape response latency was measured, and animals that showed not less than 10 sec and less than 20 sec were used. Human β-NGF (R&D Systems, final concentration 50 μg/ml) and a test substance were mixed with vehicle (20 mM Tris-HCl (pH 7.6), 145 mM NaCl, 5.4 mM KCl, 0.8 mM $MgCl_2$, 1.8 mM $CaCl_2$, 0.1% BSA), incubated at room temperature for 30 min, and subcutaneously administered to the left hind sole at 10 μl. The escape response latency was measured 5 hr later. The aptamer represented by SEQ ID NO: 153 was administered at a final concentration of 50 mg/ml (molar ratio relative to NGF:1000-fold). As a control, vehicle or a mixture of vehicle and NGF was administered in the same manner. The results are shown in Table 3 (Mean±SEM, n=9).

At 5 hr after administration, the NGF group showed significantly low escape response latency as compared to the vehicle group (p<0.01). At 5 hr after the administration, the escape response latency of the aptamer administration group was high (p<0.01) as compared to the NGF alone administration group. From the above results, it was found that this aptamer can be used as a drug for NGF-induced pain.

TABLE 3

| treated group | escape response latency (sec) | |
| --- | --- | --- |
| | before treatment | 5 hr later |
| vehicle | 14.58 ± 1.14 | 11.68 ± 0.76 |
| NGF | 14.43 ± 1.07 | 7.37 ± 0.85 |
| NGF-50 mg/ml aptamer shown by SEQ ID No: 153 | 14.42 ± 0.48 | 10.57 ± 0.57 |

Example 18

Analgesic Action of NGF Aptamer on Postoperative Pain Model

To study the efficacy of NGF aptamer therapy, a postoperative pain model which was to have induced thermal hyperalgesia was used. For the experiment, Crl:CD(SD) rats (5-week-old) were used. The tip of a catheter was indwelled in the femoral vein, the other tip was exposed from the back of the rat. One week later, Quick connect infusion system (manufactured by Strategic applications incorporated) was set on the rat, thermal hyperalgesia was evaluated one week later. As an index of thermal hyperalgesia, response latency of escape behavior to infrared irradiation from a plantar heat stimulation measuring apparatus (manufactured by Ugo Basile) to the planta was used. Acclimation to the evaluation system was performed 3 days before the start of the test. On the day of the test, escape response latency was measured, and animals that showed not less than 10 sec and less than 20 sec were used. The NGF aptamer dissolved in saline intravenously administered with a syringe pump (manufactured by TERUMO CORPORATION) in a sustained manner. As the NGF aptamer, the aptamer shown by SEQ ID NO: 82(56) (administered at 21.2 mg/240 ml/kg/96 hr) and the aptamer shown by SEQ ID NO: 82(55) (administered at 10.08 mg/240 ml/kg/96 hr) were used. As a control, vehicle was administered in the same manner. At 1 hr from the start of the administration, the skin and fascia of the right hind sole were incised, the flexor was vertically bisected, and the skin was sutured. The escape response latency was measured after incision operation, and 1, 2, 3, 4 days thereafter. The results are shown in Table 4.

The vehicle group showed significantly low ($p<0.01$) escape response latency at 1, 2, 3, 4 days after administration-incision operation as compared to before administration-incision operation. At 1, 2, 3, 4 days after administration-incision operation, the escape response latency of any aptamer administration group was significantly high ($p<0.01$) as compared to the vehicle group. The results of the experiment are shown in Table 4 and Table 5 (Mean±SEM, n=8-9). This has revealed that an anti-NGF aptamer has an analgesic action on postoperative pain model.

TABLE 4

| after administration- | escape response latency (sec) | |
|---|---|---|
| incision operation | vehicle | SEQ ID NO: 82(56) |
| day 0 | 13.21 ± 0.51 | 13.08 ± 0.65 |
| day 1 | 4.97 ± 0.60 | 8.3 ± 0.84 |
| day 2 | 6.46 ± 0.71 | 8.34 ± 0.79 |
| day 3 | 6.78 ± 0.52 | 8.05 ± 0.97 |
| day 4 | 7.08 ± 1.32 | 12.1 ± 1.41 |

TABLE 5

| after administration- | escape response latency (sec) | |
|---|---|---|
| incision operation | vehicle | SEQ ID NO: 82(55) |
| day 0 | 13.61 ± 0.64 | 12.65 ± 0.46 |
| day 1 | 3.91 ± 0.35 | 9.57 ± 1.17 |
| day 2 | 5.65 ± 0.48 | 11.60 ± 1.34 |
| day 3 | 7.34 ± 0.53 | 13.74 ± 0.83 |
| day 4 | 8.24 ± 1.02 | 16.67 ± 0.79 |

INDUSTRIAL APPLICABILITY

The aptamer of the present invention can be useful as medicaments, diagnostic agents or reagents for diseases such as algia, inflammatory disease and the like. The aptamer and the complex of the present invention can also be useful for the purification and concentration of NGF, as well as detection and quantification of NGF.

This application is based on a patent application No. 2011-213585 filed in Japan (filing date: Sep. 28, 2011), the contents of which are incorporated in full herein.

The invention claimed is:

1. An aptamer binding to NGF and forming a secondary structure represented by the formula (I):

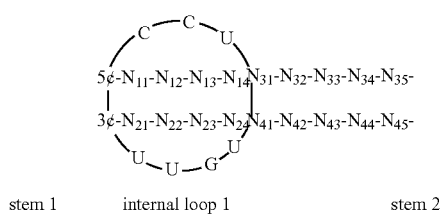

(I)

stem 1     internal loop 1     stem 2

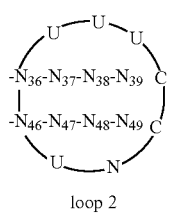

loop 2 wherein N is one nucleotide selected from the group consisting of A, G, C, U and T, $N_{11}$-$N_{13}$, $N_{21}$-$N_{23}$, $N_{32}$-$N_{38}$ and $N_{42}$-$N_{48}$ are the same or different and each is a bond or 1 or 2 nucleotides selected from the group consisting of A, G, C, U and T, $N_{14}$, $N_{24}$, $N_{31}$, $N_{41}$, $N_{39}$ and $N_{49}$ are the same or different and each is one nucleotide selected from the group consisting of A, G, C, U and T, $N_{14}$ and $N_{24}$, $N_{31}$ and $N_{41}$, and $N_{39}$ and $N_{49}$ each form a Watson-Crick base pair, $N_{11}$-$N_{12}$-$N_{13}$-$N_{14}$ and $N_{21}$-$N_{22}$-$N_{23}$-$N_{24}$ are nucleotide sequences forming a stem structure of stem 1 in combination, $N_{31}$-$N_{32}$-$N_{33}$-$N_{34}$-$N_{35}$-$N_{36}$-$N_{37}$-$N_{38}$-$N_{39}$ and $N_{41}$-$N_{42}$-$N_{43}$-$N_{44}$-$N_{45}$-$N_{46}$-$N_{47}$-$N_{48}$-$N_{49}$ are nucleotide sequences forming a stem structure of stem 2 in combination, and the final base pair of stem 1 is U-a.

2. The aptamer according to claim 1, wherein $N_{11}$-$N_{13}$, $N_{21}$-$N_{23}$, $N_{32}$-$N_{38}$ and $N_{42}$-$N_{48}$ are the same or different and each is one nucleotide selected from the group consisting of A, G, C, U and T.

3. The aptamer according to claim 1, wherein $N_{14}$ is U, $N_{24}$ is A, $N_{31}$ is G, $N_{41}$ is C, $N_{39}$ is G, and $N_{49}$ is C.

4. The aptamer according to claim 1, wherein not less than 4 Watson-Crick base pairs are formed between $N_{32}$-$N_{33}$-$N_{34}$-$N_{35}$-$N_{36}$-$N_{37}$-$N_{38}$ and $N_{42}$-$N_{43}$-$N_{44}$-$N_{45}$-$N_{46}$-$N_{47}$-$N_{48}$.

5. The aptamer according to claim 1, which is the following (a) or (b):

(a) a nucleic acid consisting of a nucleotide sequence selected from SEQ ID NO: 3, SEQ ID NOs: 9-13, SEQ ID NOs: 22-117 and SEQ ID NOs: 152-168 (wherein uracil may be thymine);

(b) a nucleic acid binding to NGF and consisting of the nucleotide sequence of the above-mentioned (a), wherein 1 to several nucleotides are substituted, deleted, inserted or added.

6. The aptamer according to claim 1, which has a base length of not more than 50.

7. The aptamer according to claim 1, wherein at least one nucleotide is modified.

8. The aptamer according to claim 7, which is modified with inverted dT or polyethylene glycol.

9. The aptamer according to claim 8, wherein the inverted dT or polyethylene glycol is bound to the 5' end or 3' end of the aptamer.

10. The aptamer according to claim 7, wherein the hydroxyl groups at the 2'-position of a ribose of respective pyrimidine nucleotides are the same or different and unreplaced or replaced by an atom or group selected from the group consisting of a hydrogen atom, a fluorine atom and a methoxy group.

11. The aptamer according to claim 7, wherein the hydroxyl groups at the 2'-position of a ribose of respective purine nucleotides are the same or different and unreplaced or replaced by an atom or group selected from the group consisting of a hydrogen atom, a fluorine atom and a methoxy group.

12. The aptamer according to claim 1, which inhibits neurite outgrowth activity and/or cell proliferation activity of NGF.

13. A pharmaceutical composition comprising the aptamer according to claim 1 and a pharmaceutically acceptable carrier.

14. A composition comprising the aptamer according to claim 1 suitable for use as an anti-pain agent.

15. A composition comprising the aptamer according to claim 1 suitable for use as an anti-inflammatory agent.

16. A method of treating a disease accompanying a pain or inflammation, comprising administering the aptamer according to claim 1 to a subject in need thereof.

17. The method of claim 16, wherein the disease accompanies pain selected from the group consisting of nociceptive pain, inflammatory pain, neuropathic pain, carcinomatous pain and fibromyalgia pain.

18. The method of claim 16, wherein the disease accompanies inflammation selected from the group consisting of systemic lupus erythematosus, multiple sclerosis, psoriasis, osteoarthritis, rheumatoid arthritis, interstitial cystitis and asthma.

19. A method of treating a disease accompanying a pain or inflammation, comprising administering the aptamer according to claim 5 to a subject in need thereof.

20. The method of claim 19, wherein the disease accompanies pain selected from the group consisting of nociceptive pain, inflammatory pain, neuropathic pain, carcinomatous pain and fibromyalgia pain.

21. The method of claim 19, wherein the disease accompanies inflammation selected from the group consisting of systemic lupus erythematosus, multiple sclerosis, psoriasis, osteoarthritis, rheumatoid arthritis, interstitial cystitis and asthma.

* * * * *